US006867041B2

(12) United States Patent
Berenson et al.

(10) Patent No.: US 6,867,041 B2
(45) Date of Patent: Mar. 15, 2005

(54) SIMULTANEOUS STIMULATION AND CONCENTRATION OF CELLS

(75) Inventors: Ronald Berenson, Mercer Island, WA (US); Che Law, Shoreline, WA (US); Mark Bonyhadi, Issaquah, WA (US); Narinder Saund, Seattle, WA (US); Stewart Craig, Issaquah, WA (US); Alan Hardwick, Seattle, WA (US); Dale Kalamasz, Redmond, WA (US); David McMillen, Seattle, WA (US)

(73) Assignee: XCYTE Therapies, Inc., Seattle, WA (US)

( * ) Notice: Subject to any disclaimer, the term of this patent is extended or adjusted under 35 U.S.C. 154(b) by 0 days.

(21) Appl. No.: 10/133,236

(22) Filed: Apr. 26, 2002

(65) Prior Publication Data

US 2003/0124122 A1 Jul. 3, 2003

Related U.S. Application Data

(63) Continuation-in-part of application No. 09/960,264, filed on Sep. 20, 2001, now Pat. No. 6,797,514, which is a continuation-in-part of application No. 09/794,230, filed on Feb. 26, 2001.
(60) Provisional application No. 60/184,788, filed on Feb. 24, 2000, and provisional application No. 60/249,902, filed on Nov. 17, 2000.

(51) Int. Cl.[7] .............................................. C12N 5/00

(52) U.S. Cl. ....................... 435/377; 435/325; 435/326; 435/375; 436/526

(58) Field of Search ................................ 435/325, 326, 435/377, 375; 436/526

(56) References Cited

U.S. PATENT DOCUMENTS

| | | | |
|---|---|---|---|
| 5,190,878 A | 3/1993 | Wilhelm ...................... 435/285 |
| 5,443,983 A | 8/1995 | Ochoa et al. ............ 435/240.2 |
| 5,470,730 A | 11/1995 | Greenberg et al. ....... 435/172.3 |
| 5,674,704 A | 10/1997 | Goodwin et al. ........... 435/69.1 |
| 5,735,279 A | 4/1998 | Klaveness et al. .......... 128/654 |
| 5,766,944 A | * 6/1998 | Ruiz |
| 5,804,442 A | 9/1998 | Romet-Lemonne et al. 435/374 |
| 5,837,477 A | 11/1998 | Germain et al. ........... 435/7.24 |
| 5,858,358 A | 1/1999 | June et al. ................ 424/130.1 |
| 5,888,807 A | 3/1999 | Palsson et al. ........... 435/293.2 |
| 5,942,607 A | 8/1999 | Freeman et al. ............ 536/23.5 |
| 5,962,319 A | 10/1999 | Ogawa et al. ............... 435/325 |
| 5,985,653 A | 11/1999 | Armstrong et al. ....... 435/303.1 |
| 6,096,532 A | 8/2000 | Armstrong et al. ....... 435/286.5 |
| 6,113,901 A | 9/2000 | Bluestone ................ 424/154.1 |
| 6,129,916 A | 10/2000 | Chang ..................... 424/179.1 |
| 6,143,297 A | 11/2000 | Bluestone ................ 424/184.1 |
| 6,197,298 B1 | 3/2001 | Chang ..................... 424/179.1 |
| 6,316,257 B1 | 11/2001 | Flyer et al. .............. 435/372.3 |
| 6,352,694 B1 | 3/2002 | June et al. ................ 424/93.71 |
| 6,355,779 B1 | 3/2002 | Goodwin et al. ...... 530/388.23 |
| 2001/0031253 A1 | 10/2001 | Gruenberg ................. 424/93.1 |
| 2002/0090362 A1 | 7/2002 | Strauss ..................... 424/93.21 |
| 2002/0182730 A1 | 12/2002 | Gruenberg .................. 435/375 |
| 2003/0039650 A1 | 2/2003 | Gruenberg ............... 424/144.1 |
| 2003/0134341 A1 | 7/2003 | Gruenberg ................. 435/7.21 |
| 2003/0134415 A1 | 7/2003 | Gruenberg ................. 435/372 |
| 2003/0170238 A1 | 9/2003 | Gruenberg ............... 424/144.1 |
| 2003/0175242 A1 | 9/2003 | Gruenberg ................. 424/93.2 |
| 2003/0175272 A1 | 9/2003 | Gruenberg ............... 424/144.1 |
| 2003/0194395 A1 | 10/2003 | Gruenberg et al. ........ 424/93.7 |

FOREIGN PATENT DOCUMENTS

| | | |
|---|---|---|
| EP | 633930 B1 | 4/2000 |
| WO | WO 97/01304 | 1/1997 |
| WO | WO 97/05233 | 2/1997 |
| WO | WO 97/05239 | 2/1997 |
| WO | WO 00/02520 | 1/2000 |
| WO | WO 03/024312 | 3/2003 |
| WO | WO 03/025158 | 3/2003 |
| WO | WO 03/034820 | 5/2003 |
| WO | WO 03/043643 | 5/2003 |
| WO | WO 03/077658 | 9/2003 |

OTHER PUBLICATIONS

Baroja, M.L. et al., "The Anti–T Cell Monoclonal Antibody 9.3 (Anti–CD28) Provides a Helper Signal and Bypasses the Need for Accessory Cells in T Cell Activation with Immobilized Anti–CD3 and Mitogens," *Cellular Immunology* 120: 205–217, 1989.

Bergstresser, P.R. et al., "T Cell–Mediated Terminal Maturation of Dendritic Cells," in *Dendritic Cell in Fundamental and Clinical Immunology*, Ricciardi–Castognoli (Ed.), Plenum Press, New York, 1997, pp. 65–69.

(List continued on next page.)

*Primary Examiner*—Leon B. Lankford, Jr.
(74) *Attorney, Agent, or Firm*—Seed IP Law Group PLLC

(57) ABSTRACT

The present invention relates generally to methods for stimulating cells, and more particularly, to a novel method to concentrate and/or stimulate cells that maximizes stimulation and/or proliferation of such cells. In the various embodiments, cells are stimulated and concentrated with a surface yielding enhanced proliferation, cell signal transduction, and/or cell surface moiety aggregation. In certain aspects methods for stimulating a population of cells such as T-cells, by simultaneous concentration and cell surface moiety ligation are provided by contacting the population of cells with a surface, that has attached thereto one or more agents that ligate a cell surface moiety and applying a force that predominantly drives cell concentration and cell surface moiety ligation, thereby inducing cell stimulation, cell surface moiety aggregation, and/or receptor signaling enhancement. Also provided are methods for producing phenotypically tailored cells, including T-cells for the use in diagnostics, drug discovery, and the treatment of a variety of indications, including cancer, viral infection, and immune related disorders. Compositions of cells having specific phenotypic properties produced by these processes are further provided.

21 Claims, 43 Drawing Sheets

OTHER PUBLICATIONS

Groh, V. et al., "Stimulation of T cell autoreactivity by anomalous expression of NKG2D and its MIC ligands in rheumatoid arthritis," *Proceedings of the National Academy of Sciences* 100(16): 9452–9457, Aug. 5, 2003.

Lanzavecchia, A., "The Role of Dendritic Cells in the Generation of Effector and Memory T Cell Responses," from *The Midwinter Conference of Immunologists*, Jan. 22–25, 2000, available at www.midwconfimmunol.org/Midwinter00/sessions/lanzavecchia.html.

Li, Q. et al., "Expanded Tumor–reactive $CD4^+$ T–Cell Responses to Human Cancers Induced by Secondary Anti–CD3/Anti–CD28 Activation," *Clinical Cancer Research* 5: 461–469, Feb. 1999.

Li, Q. et al., "Immunological Effects of BCG as an Adjuvant in Autologous Tumor Vaccines," *Clinical Immunology* 94(1): 64–72, Jan. 2000.

Zou, J.–P. et al., "Tumor–Bearing Mice Exhibit A Progressive Increase in Tumor Antigen–Presenting Cell Function and A Reciprocal Decrease in Tumor Antigen–Responsive $CD4^+$ T Cell Activity," *The Journal of Immunology* 148(2): 648–655, Jan. 15, 1992.

Bretscher, P., "The two–signal model of lymphocyte activation twenty–one years later," *Immunology Today* 13(2): 74–76, 1992.

Garland et al., "The use of Teflon cell culture bags to expand functionally active $CD8^+$ cytotoxic T lymphocytes," *Journal of Immunological Methods* 227: 53–63, 1999.

Haanen et al., "Selective Expansion of Cross–reactive $CD8^+$ Memory T Cells by Viral Variants," *J. Exp. Med.* 190(9): 1319–1328, Nov. 1, 1999.

Iezzi et al., "The Duration of Antigenic Stimulation Determines the Fate of Naive and Effector T Cells," *Immunity* 8: 89–95, Jan. 1998.

June et al., "The B7 and CD28 receptor families," *Immunology Today* 15(7): 321–331, 1994.

Kato et al., "Gene Transfer of CD40–Ligand Induces Autologous Immune Recognition of Chronic Lymphocytic Leukemia B Cells," *J. Clin. Invest.* 101(5): 1133–1141, Mar. 1998.

Krawczyk et al., "Cbl–b Is a Negative Regulator of Receptor Clustering and Raft Aggregation in T Cells," *Immunity* 13: 463–473, Oct. 2000.

Liebowitz et al., "Costimulatory approaches to adoptive immunotherapy," *Current Opinion in Oncology* 10: 533–541, 1998.

Ranheim and Kipps, "Activated T Cells Induce Expression of B7/BB1 on Normal or Leukemic B Cells through a CD40–dependent Signal," *J. Exp. Med.* 177: 925–935, Apr. 1993.

Ten Berge et al., "Selective Expansion of a Peripheral Blood $CD8^+$ Memory T Cell Subset Expressing Both Granzyme B and $_L$–Selectin During Primary Viral Infection in Renal Allograft Recipients," *Transplantation Proceedings* 30: 3975–3977, 1998.

Bonyhadi, M. et al., "Xcellearate: An Autologous T Cell Immunotherapy Approach for Treating B–Cell Lymphocytic Leukemia (B–CLL)," in *Proceedings of the $42^{nd}$ Annual Meeting of the American Society of Hematology*, San Francisco, Dec. 1–5, 2000, vol. 96, No. 11, part 1, ABSTRACT # 3616.

Creson, J. et al., "The Mode and Duration of Anti–CD28 Costimulation Determine Resistance to Infection by Macrophage–Tropic Strains of Human Immunodeficiency Virus Type 1 in Vitro," *Journal Of Virology*, 73(11):9337–9347, Nov. 1999.

Hami, L. et al., "Xcellerate™: A Platform Process for the GMP Manufacture of Activated T Cells for the Treatment of Patients with Cancer and Immune Dysfunction," in *Proceedings of the $42^{nd}$ Annual Meeting of the American Society of Hematology*, San Francisco, Dec. 1–5, 2000, vol. 96, No. 11, part 1, abstract # 3630.

Kalamasz, D. et al., "Storage Shipment of Freshly Harvested or Cryopreserved Xcellerate™ Activated T Cells for Clinical Applications," in *Proceedings of the $42^{nd}$ Annual Meeting of the American Society of Hematology*, San Francisco, Dec. 1–5, 2000, vol. 96, No. 11, part 2, abstract # 5113.

Larsson, S. et al., "Productive Cytomegalovirus (CMV) Infection Exclusively in CD13–Positive Peripheral Blood Mononuclear Cells from CMV–Infected Individuals," *Transplantation*, 65(3):411–415, Feb. 15, 1998.

Polanski, M. et al., "Xcellerate( : A Closed, Scalable Process for the GMP Manufacture of Stable Activated T Cells," in *Proceedings of the $15^{th}$ Annual Scientific Meeting of the Society for Biological Therapy*, Seattle, Oct. 26–29, 2000, and *Journal of Immunotherapy*, (23)5:599, Sep. 2000.

* cited by examiner

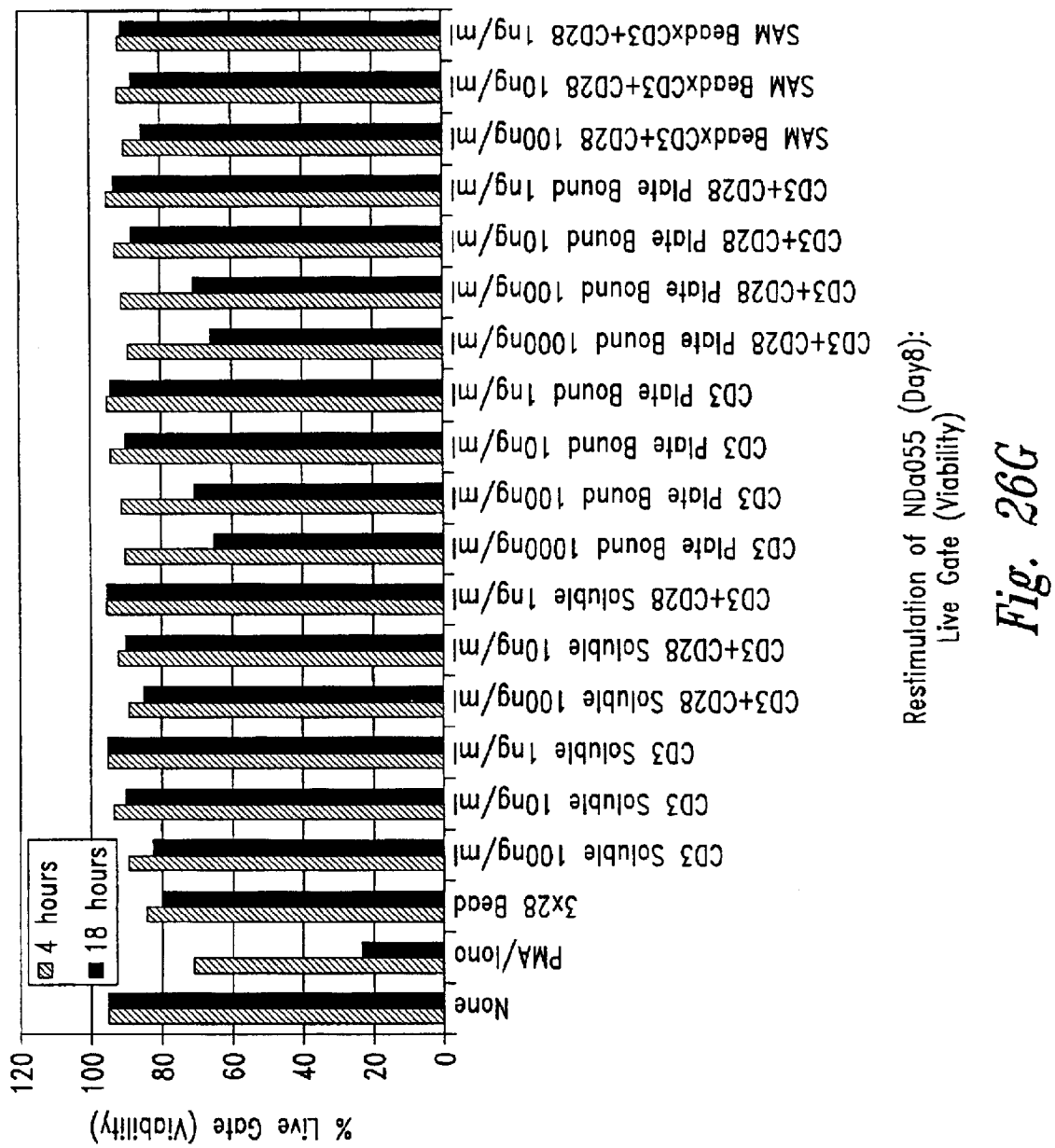

SIMULTANEOUS STIMULATION AND CONCENTRATION OF CELLS

TECHNICAL FIELD

The present invention relates generally to methods for stimulating cells, and more particularly, to methods to concentrate and/or stimulate cells that maximizes stimulation of such cells. The present invention also relates to compositions of cells, including stimulated T-cells having specific phenotypic characteristics.

BACKGROUND OF THE INVENTION

Many cells are activated or regulated via receptors embedded in lipid rafts found in cell surface membranes. See K. Simons and D. Toomre, *Nature Rev.* 1:31, 2000. Lipid rafts form concentrating platforms for individual receptors that are activated by ligand binding. Lipid rafts are involved in cellular signaling processes, including immunoglobulin E signaling during the allergic immune response, glial-cell-derived neurotrophic factor signaling important for the development and maintenance of the nervous system, Ras signaling, central to many signal transduction processes, and T-cell antigen receptor (TCR) signaling.

The T-cell antigen receptor (TCR) is a multisubunit immune recognition receptor that associates with the CD3 complex and binds to peptides presented by the major histocompatibility complex (MHC) class I and II proteins on the surface of antigen-presenting cells (APCs). Binding of TCR to the antigenic peptide on the APC is the central event in T-cell activation, which occurs at an immunological synapse at the point of contact between the T-cell and the APC. Moreover, data suggest that clustering of lipid rafts is essential to the formation of the immunological synapse. Krawczyk et al., *Immunity* 13(4):463–73, 2000.

To sustain T-cell activation, T lymphocytes typically require a second co-stimulatory signal. Co-stimulation is typically necessary for a T helper cell to produce sufficient cytokine levels that induce clonal expansion. Bretscher, *Immunol. Today* 13:74, 1992; June et al, *Immunol. Today* 15:321, 1994. The major co-stimulatory signal occurs when a member of the B7 family ligands (CD80 (B7.1) or CD86 (B7.2)) on an activated antigen-presenting cell (APC) binds to CD28 on a T-cell.

Methods of stimulating the expansion of certain subsets of T-cells have the potential to generate a variety of T-cell compositions useful in immunotherapy. Successful immunotherapy can be aided by increasing the reactivity and quantity of T-cells by efficient stimulation.

The various techniques available for expanding human T-cells have relied primarily on the use of accessory cells and/or exogenous growth factors, such as interleukin-2 (IL-2). IL-2 has been used together with an anti-CD3 antibody to stimulate T-cell proliferation, predominantly expanding the CD8$^+$ subpopulation of T-cells. Both APC signals are thought to be required for optimal T-cell activation, expansion, and long-term survival of the T-cells upon re-infusion. The requirement for MHC-matched APCs as accessory cells presents a significant problem for long-term culture systems because APCs are relatively short-lived. Therefore, in a long-term culture system, APCs must be continually obtained from a source and replenished. The necessity for a renewable supply of accessory cells is problematic for treatment of immunodeficiencies in which accessory cells are affected. In addition, when treating viral infection, if accessory cells carry the virus, the cells may contaminate the entire T-cell population during long-term culture.

In the absence of exogenous growth factors or accessory cells, a co-stimulatory signal may be delivered to a T-cell population, for example, by exposing the cells to a CD3 ligand and a CD28 ligand attached to a solid phase surface, such as a bead. See C. June, et al. (U.S. Pat. No. 5,858,358); C. June et al. WO 99/953823. While these methods are capable of achieving therapeutically useful T-cell populations, increased robustness and ease of T-cell preparation remain less than ideal.

In addition, the methods currently available in the art have not focused on short-term expansion of T-cells or obtaining a more robust population of T-cells and the beneficial results thereof and/or the expansion of particular T-cell subclasses/phenotypes. Furthermore, the applicability of expanded T-cells has been limited to only a few disease states. For maximum in vivo effectiveness, theoretically, an ex vivo- or in vivo-generated, activated T-cell population should be in a state that can maximally orchestrate an immune response to cancer, infectious disease, or other disease states. The present invention provides methods to generate an increased number of more highly activated and more pure T-cells that have surface receptor and cytokine production characteristics that appear more healthy and natural than other expansion methods.

In addition, the present invention provides compositions of phenotypically tailored cell populations of any target cell, including T-cell populations and parameters for producing the same, as well as providing other related advantages.

SUMMARY OF THE INVENTION

The present invention generally provides methods for stimulating cells, and more particularly, provides a novel method to concentrate and stimulate cells that maximizes stimulation of such cells. In one aspect the present invention provides methods for stimulating a population of T-cells by simultaneous T-cell concentration and cell surface moiety ligation that comprises providing a population of cells wherein at least a portion thereof comprises T-cells, contacting the population of cells with a surface, wherein the surface has attached thereto one or more agents that ligate a cell surface moiety of at least a portion of the T-cells and stimulates at least that portion of T-cells or a subpopulation thereof and applying a force that predominantly drives T-cell concentration and T-cell surface moiety ligation, thereby inducing T-cell stimulation.

In one embodiment of the methods the surface has attached thereto a first agent that ligates a first cell surface moiety of a T-cell; and the same or a second surface has attached thereto a second agent that ligates a second moiety of said T-cell, wherein said ligation by the first and second agent induces proliferation of said T-cell. In related embodiments the surface may be biocompatible, natural or synthetic, comprise a polymer, comprise collagen, purified proteins, purified peptides, polysaccharides, glycosaminoglycans, or extracellular matrix compositions. In certain embodiments, the polysaccharides are selected from chitosan, alginate, dextran, hyaluronic acid, and cellulose and the polymer is selected from polystyrene, polyesters, polyethers, polyanhydrides, polyalkylcyanoacrylates, polyacrylamides, polyorthoesters, polyphosphazenes, polyvinylacetates, block copolymers, polypropylene, polytetrafluoroethylene (PTFE), or polyurethanes. In yet other embodiments, the polymer may comprise lactic acid or a copolymer. While in still yet other embodiments, the polymer may be a copolymer. Such copolymers can be a variety of known copolymers and may include lactic acid and/or glycolic acid (PLGA).

With respect to biocompatible surfaces, such surfaces may be biodegradable or non-biodegradable. In related embodiments, while not limited thereto, the non-biodegradable surfaces may comprise poly(dimethysiloxane) and/or poly(ethylene-vinyl acetate). Further, the biocompatible surface, while not limited thereto, may include cell surfaces, liposomes, collagen, metal, hydroxyapatite, glass, aluminate, bioceramic materials, hyaluronic acid polymers, alginate, acrylic ester polymer, lactic acid polymer, glycolic acid polymer, lactic acid/glycolic acid polymer, purified proteins, purified peptides, and/or extracellular matrix compositions. In certain embodiments, the biocompatible surfaces may be magnetic. In further embodiments, the biocompatible surfaces may be magnetic and/or ingestible.

In still yet further embodiments, the biocompatible surface is associated with an implantable device. The implantable device may be any that is desired to be used and may include a stent, a catheter, a fiber, a hollow fiber, a patch, or a suture. In related embodiments the surface may be glass, silica, silicon, collagen, hydroxyapatite, hydrogels, PTFE, polypropylene, polystyrene, nylon, or polyacrylamide. Yet additional embodiments include wherein the surface comprises a lipid, a plate, a bag, a rod, a pellet, a fiber, or a mesh. Other embodiments include wherein the surface is a particle and additionally wherein the particle comprises a bead, a microsphere, a nanoparticle, or a colloidal particle. Particle and bead sizes may also be chosen and may have a variety of sizes including wherein the bead is about 5 nanometers to about 500 microns in diameter.

In other embodiments, the agents used in the methods can be independently selected from a protein ligand, a natural ligand, or a synthetic ligand. Further, the agents may also comprise an antibody, an antibody fragment, a peptide, a polypeptide, a glycopeptide, a soluble receptor, a steroid, a hormone, a mitogen, an antigen, a superantigen, a growth factor, a cytokine, a lectin, a viral protein, an adhesion molecule, or a chemokine. In specific embodiments, at least one agent is an antibody or an antibody fragment. While in yet other embodiments, a first agent is an antibody and a fragment thereof, and a second agent is an antibody or a fragment thereof. It would of course be understood that the first and second agents could either be the same or different antibodies.

In selected embodiments the first agent is an anti-CD3 antibody, an anti-CD2 antibody, or an antibody fragment of an anti-CD3 or anti-CD2 antibody. Further selected embodiments include wherein the second agent is an anti-CD28 antibody or antibody fragment thereof. Further embodiments include wherein the second agent comprises a natural ligand for CD28, such as, e.g., B7-1 or B7-2. In addition, other stimulatory agents could be used.

In certain embodiments, the force used to drive the cells may include a variety of forces that function similarly, and include a force greater than gravitational force, a hydraulic force, a filtration force generated by transmembrane pressure, a centrifugal force, or a magnetic force. When magnetic forces are used, some embodiments utilize a magnetic force that is generated by a magnet having a magnetic field strength ranging from between about 200 gauss to about 12,000 gauss at the surface of the magnet.

Another embodiment includes surfaces wherein the surface is a surface of a paramagnetic particle. While in embodiments utilizing surfaces including a surface of a paramagnetic particle the agents attachment to the surface may be covalent, noncovalent, electrostatic, inter-molecular adhesion, or hydrophobic.

In still yet other embodiments the T-cells that are ligated are separated from the T-cells that are not ligated. While in other embodiments the T-cells ameliorate immune response dysfunction.

Other aspects that may be combined with the embodiments above include, for example methods for stimulation of T-cells by simultaneous cell surface moiety ligation and T-cell aggregation comprising providing a cell population comprising T-cells, contacting said cell population with a surface, wherein said surface has attached thereto one or more ligands specific for a cell surface moiety, applying a force that drives concentration of T-cells and surface and incubating said cells for a period of time sufficient to achieve desired stimulation. In related embodiments the time sufficient to achieve desired stimulation may range from 1 minute to 60 days and all integer values in between. For example, it may be desirable in certain embodiments, to generate T cell lines that require numerous stimulation cycles. In other embodiments, it may be desirable to clone T cells from a stimulated T cell line using either limiting dilution or by cell sorting. In certain embodiments, the time range may be from about 1 day to about 0 days. In yet a further embodiment, the time range may be from about 1 day to about 10 days. In an additional embodiment, the time range may be from about 1 day to about 8 days, while in yet other embodiments the time range may be from about 3 days to about 5 days, or from about 1 day to about 5 days. In related embodiments the incubation temperature may range from about 2 to about 38° C.

Further embodiments that can be used with all the recited methods include wherein the surface is selected from glass, silica, silicon, collagen, hydroxyapatite, hydrogels, PTFE, polypropylene, polystyrene, nylon, dextran, or polyacrylamide or mixtures of any of these. Further, embodiments include prior to or concurrently with any steps noted above, separating T-cells concentrated with surface from non-concentrated cells.

In other aspects methods of inducing T-cell activation in vivo are provided, comprising providing paramagnetic particles to an animal, said particles having attached thereto, ligands specific for a T-cell surface moiety that induces T-cell activation; applying a magnetic field to a discrete region of the animal; and thereby inducing localization and activation of T-cells bound to said particles at said discrete region.

An additional aspect is provided that includes methods for stimulating a population of target cells by simultaneous target cell concentration and target cell surface moiety ligation, comprising providing a population of cells wherein at least a portion thereof comprises target cells contacting said population of cells with a surface, wherein said surface has attached thereto one or more agents that ligate a cell surface moiety of at least a portion of said target cells and stimulates at least said portion of target cells, applying a force that predominantly drives target cell concentration and target cell surface moiety ligation, thereby inducing target cell stimulation.

In certain embodiments, the methods described herein utilize a surface that has attached thereto a first agent that ligates a first cell surface moiety of a target cell; and the same or a second surface has attached thereto a second agent that ligates a second moiety of said target cell, wherein said ligation by the first and second agent induces signal transduction in said target cell.

As noted previously, the surface may include a variety of components including collagen, purified proteins, purified peptides, polysaccharides, glycosaminoglycans, and/or extracellular matrix compositions. Some polysaccharides that are utilized in specific embodiments may include chitosan, alginate, dextran, hyaluronic acid, and/or cellulose. Further, polymers as noted above and applicable to all methods may be selected from polyesters, polyethers, polyanhydrides, polyalkylcyanoacrylates, polyacrylamides, polyorthoesters, polyphosphazenes, polyvinylacetates, block copolymers, polypropylene, polytetrafluoroethylene (PTFE), and/or polyurethanes and mixtures thereof.

In other aspects the methods are provided for stimulation of target cells by cell surface moiety ligation and target cell concentration, comprising providing a cell population comprising target cells, contacting said cell population with a surface, wherein said surface has attached thereto one or more ligands specific for a cell surface moiety, applying a force that drives concentration of target cells and concentration of said cells on said surface and incubating said cells for a period of time sufficient to achieve desired stimulation.

In related embodiments the target cells may be T-cells, B-cells, or stem cells.

Other aspects provide methods of inducing target cell stimulation in vivo, comprising providing paramagnetic particles to an animal, said particles having attached thereto, ligands specific for a target cell surface moiety that induces target cell stimulation; applying a magnetic field to a discrete region of the animal; and thereby inducing localization and stimulation of the target cells bound to said particles at said discrete region.

Still other aspects are provided which include methods for inducing receptor polarization in receptor bearing cells comprising providing a cell population, contacting said cell population with a solid surface, wherein said solid surface has attached thereto one or more ligands specific for a cell surface receptor present on at least a portion of said cell population and applying a force that drives cell concentration and cell surface receptor ligation.

Other aspects include methods for inducing aggregation of cell surface molecules, comprising providing a population of cells having a target cell surface molecule, contacting said population of cells with a solid surface, wherein said solid surface has attached thereto a ligand for at least one target cell surface molecule, applying a force that drives aggregation of targeted cell surface molecules.

In certain embodiments the cell population comprises lymphocytes.

In yet other certain embodiments the receptor or cell surface moiety binding leads to down regulation or suppression of a cellular event. Related embodiments include wherein the receptor binding leads to up regulation or activation of a cellular event, which may include, for example, receptor mediated signal transduction.

Another embodiment of the invention envisions the use of a force to drive concentration or orientation of cell surface moieties.

Yet additional embodiments of the present invention provide phenotypically tailored target cell populations and/or compositions including T-cell compositions. In addition, methods are provided for activating such cells by ligating a cell surface moiety. Further provided are methods for inducing a population of T-cells to proliferate, comprising contacting the T-cells with a solid surface for a period of time of between about two hours and about nine days, the solid surface having immobilized thereon a first agent and second agent, and wherein the first agent provides an activation signal and the second agent provides a co-stimulatory signal to said T-cells.

These and other aspects of the present invention will become evident upon reference to the following detailed description and attached drawings.

BRIEF DESCRIPTION OF THE DRAWINGS

FIG. 6A, depicts CD25 expression on $CD4^+$ cells, while FIG. 6B depicts CD25 expression on $CD8^+$ cells.

FIG. 7A, depicts CD154 expression on $CD4^+$ cells, while FIG. 7B depicts CD154 expression on $CD8^+$ cells.

FIG. 11A represents the expression profile of CD25 on $CD4^+$ cells, while FIG. 11B represents the expression profile of CD25 on $CD8^+$ cells.

FIG. 13A represents the expression profile of CD25 on CD4+ cells, while FIG. 13B represents the expression profile of CD25 on CD8+ cells.

FIG. 14A represents the expression profile of CD154 on CD4+ cells, while FIG. 14B represents the expression profile of CD154 on CD8+ cells.

FIG. 16A represents the expression of CD54 on CD4+ cells, while FIG. 16B represents the expression of CD54 on CD8+ cells.

FIGS. 17A and 17B represent CD4+ and CD8+ cells present in samples 13 days post-stimulation with anti-CD3 and anti-CD28 coupled beads (17A) and 18 days post-primary stimulation and 7 days post-secondary stimulation with anti-CD3 and anti-CD28 coupled beads (17B). FIGS. 17C and 17D are flow cytometry data plots representing CD154 and CD137 expression after secondary stimulation of cells obtained from a patient with B-cell chronic lymphocytic leukemia.

FIGS. 26A–26L are bar graphs representing flow cytometry data of CD62L expression (mean fluorescence intensity, MFI) (26A), CD49d (MFI) (26B), CD25 (MFI) (26C), CD69 (MFI) (26D), CD154 (MFI) (26E), forward light scatter (size) (26F), viability (% live gate) (26G); all following stimulation with anti-CD3 and anti-CD28 co-immobilized beads and re-stimulation with the same at day 8. FIGS. 26H–26L depict CD62L, CD69, CD49d, CD154, and CD25 at 4 and 18 hours post-stimulation, respectively.

DETAILED DESCRIPTION OF THE INVENTION

Figure 1:
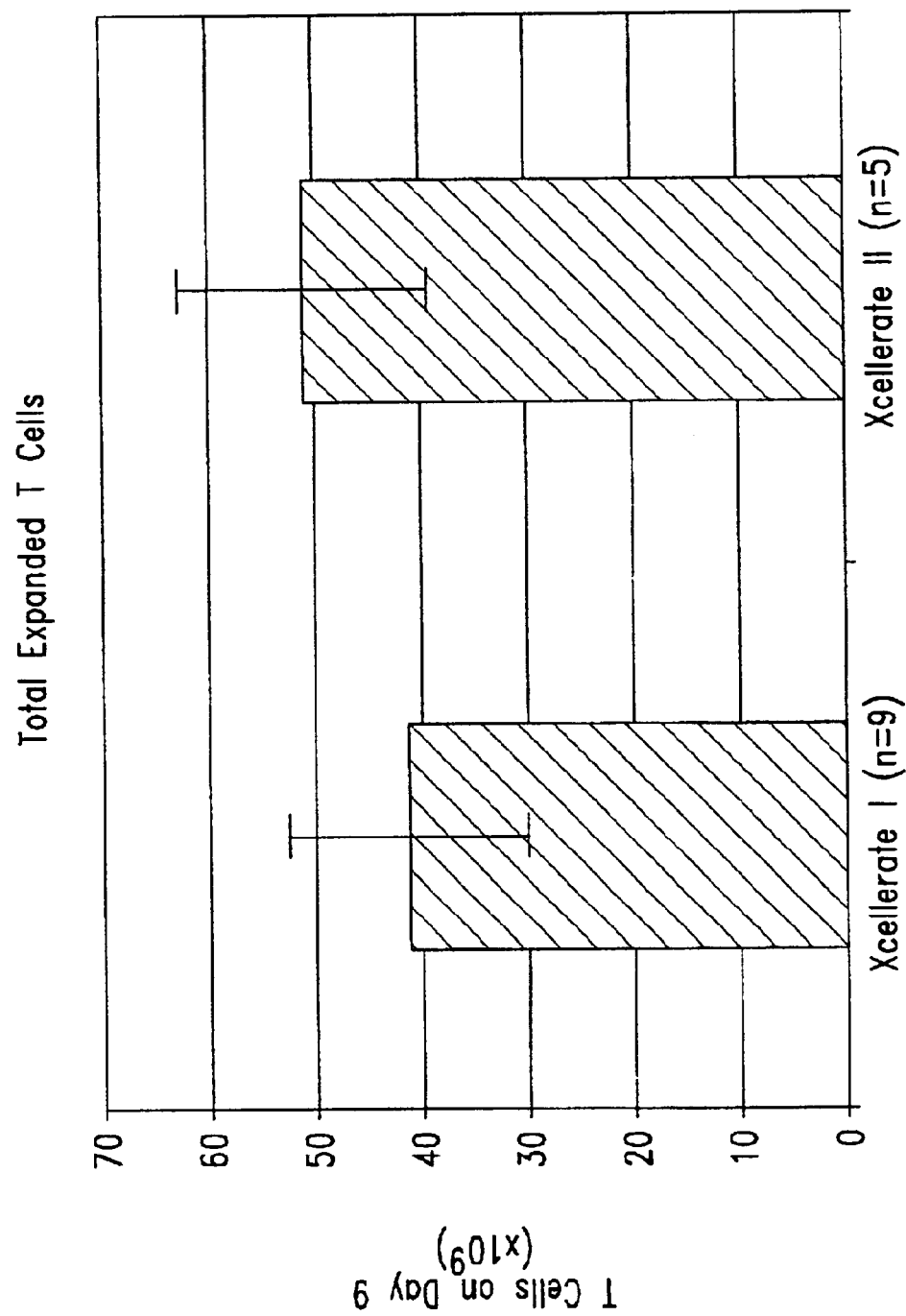
FIG. 1 is a plot comparing the total numbers of activated and expanded T-cells measured at day 8 starting with about $0.5 \times 10^9$ T-cells with (XCELLERATE II™) or without (XCELLERATE I™) magnetic concentration and stimulation.

Prior to setting forth the invention, it may be helpful to an understanding thereof to set forth definitions of certain terms that will be used hereinafter.

The term "biocompatible", as used herein, refers to the property of being predominantly non-toxic to living cells.

The term "stimulation", as used herein, refers to a primary response induced by ligation of a cell surface moiety. For example, in the context of receptors, such stimulation entails the ligation of a receptor and a subsequent signal transduction event. With respect to stimulation of a T-cell, such stimulation refers to the ligation of a T-cell surface moiety that in one embodiment subsequently induces a signal transduction event, such as binding the TCR/CD3 complex. Further, the stimulation event may activate a cell and upregulate or downregulate expression or secretion of a molecule, such as downregulation of TGF-β. Thus, ligation of cell surface moieties, even in the absence of a direct signal transduction event, may result in the reorganization of cytoskeletal structures, or in the coalescing of cell surface moieties, each of which could serve to enhance, modify, or alter subsequent cell responses.

The term "activation", as used herein, refers to the state of a cell following sufficient cell surface moiety ligation to induce a noticeable biochemical or morphological change. Within the context of T-cells, such activation, refers to the state of a T-cell that has been sufficiently stimulated to induce cellular proliferation. Activation of a T-cell may also induce cytokine production and performance of regulatory or cytolytic effector functions. Within the context of other cells, this term infers either up or down regulation of a particular physico-chemical process.

The term "force", as used herein, refers to an artificial or external force applied to the cells to be stimulated that induces cellular concentration and concentration of cells with the agent that binds a cell surface moiety. For example, the term "force" includes any force greater than gravity (i.e., in addition to gravity and not solely gravitational force) that induces cell concentration and/or cell surface moiety aggregation. Such forces include transmembrane pressure such as filtration, a hydraulic force, an electrical force, an acoustical force, a centrifugal force, or a magnetic force. Ideally, the force utilized drives the concentration of the target cell of interest with an agent that ligates a cell surface moiety. In various contexts, the force can be pulsed, i.e., applied and reapplied (e.g., a magnetic force could be turned off and on, pulsing the population of cells in combination with a paramagnetic particle).

The term "simultaneous", as used herein, refers to the fact that inherently upon concentrating cells at a surface that has cell surface moiety binding agents attached thereto, results in concentration of cells with each other and with the surface, thus ligands (i.e., agents). However, the use of the term "simultaneous" does not preclude previous binding of the target cells with a surface having cell surface moiety binding agents attached thereto, as concentration and further ligand binding occurs simultaneously at the concentration surface. For example, within the context of T-cell activation, the T-cells may be exposed to a surface such as a paramagnetic bead having anti-CD3 and anti-CD28 antibodies attached thereto and subsequently concentrated by a magnetic field. Thus, in this context while cells and beads have previous contact and ligation, nevertheless, during concentration of cells additional ligation occurs.

The term "target cell", as used herein, refers to any cell that is intended to be stimulated by cell surface moiety ligation.

An "antibody", as used herein, includes both polyclonal and monoclonal antibodies; primatized (e.g., humanized); murine; mouse-human; mouse-primate; and chimeric; and may be an intact molecule, a fragment thereof (such as scFv, Fv, Fd, Fab, Fab' and F(ab)'$_2$ fragments), or multimers or aggregates of intact molecules and/or fragments; and may occur in nature or be produced, e.g., by immunization, synthesis or genetic engineering; an "antibody fragment," as used herein, refers to fragments, derived from or related to an antibody, which bind antigen and which in some embodiments may be derivatized to exhibit structural features that facilitate clearance and uptake, e.g., by the incorporation of galactose residues. This includes, e.g., F(ab), F(ab)'$_2$, scFv, light chain variable region ($V_L$), heavy chain variable region ($V_H$), and combinations thereof.

The term "protein", as used herein, includes proteins, polypeptides and peptides; and may be an intact molecule, a fragment thereof, or multimers or aggregates of intact molecules and/or fragments; and may occur in nature or be produced, e.g., by synthesis (including chemical and/or enzymatic) or genetic engineering.

The term "agent", "ligand", or "agent that binds a cell surface moiety", as used herein, refers to a molecule that binds to a defined population of cells. The agent may bind any cell surface moiety, such as a receptor, an antigenic determinant, or other binding site present on the target cell population. The agent may be a protein, peptide, antibody and antibody fragments thereof, fusion proteins, synthetic molecule, an organic molecule (e.g., a small molecule), or the like. Within the specification and in the context of T-cell stimulation, antibodies are used as a prototypical example of such an agent.

The terms "agent that binds a cell surface moiety" and "cell surface moiety", as used herein, are used in the context of a ligand/anti-ligand pair. Accordingly, these molecules should be viewed as a complementary/anti-complementary set of molecules that demonstrate specific binding, generally of relatively high affinity (an affinity constant, $K_a$, of about $10^6$ $M^{-1}$).

A "co-stimulatory signal", as used herein, refers to a signal, which in combination with a primary signal, such as TCR/CD3 ligation, leads to T-cell proliferation.

A "ligand/anti-ligand pair", as used herein, refers to a complementary/anti-complementary set of molecules that demonstrate specific binding, generally of relatively high affinity (an affinity constant, $K_a$, of about $10^6$ $M^{-1}$,). Exemplary ligand/anti-ligand pairs enzyme/inhibitor, hapten/antibody, lectin/carbohydrate, ligand/receptor, and biotin/avidin or streptavidin. Within the context of the present invention specification receptors and other cell surface moieties are anti-ligands, while agents (e.g., antibodies and antibody fragments) reactive therewith are considered ligands.

"Separation", as used herein, includes any means of substantially purifying one component from another (e.g., by filtration or magnetic attraction).

"Quiescent", as used herein, refers to a cell state wherein the cell is not actively proliferating.

A "surface", as used herein, refers to any surface capable of having an agent attached thereto and includes, without limitation, metals, glass, plastics, co-polymers, colloids, lipids, cell surfaces, and the like. Essentially any surface that is capable of retaining an agent bound or attached thereto. A prototypical example of a surface used herein, is a particle such as a bead.

One aspect of the present invention is directed to the surprising finding that the combination of a force which induces the concentration of cells and ligation of cell surface moieties results in a profound enhancement in stimulation of these cells. In the prototypic example set forth herein, T-cells are utilized. However, one of skill in the art would readily conclude that the present invention has broad applicability to any cell type where cell surface moiety ligation or aggregation is desired or where such binding leads to a subsequent cellular signaling event (e.g., receptors). While not wishing to be bound by theory, the present invention may function by taking advantage of a phenomenon involving lipid rafting and/or receptor polarization. The phenomena are similar in that they suggest either initiation/enhancement of signal transduction by the aggregation of lipid rafts comprising cell surface moieties or enhanced signal transduction due to localization (i.e., polarization) of receptors at one, or even several area(s) of a cell. Thus, not only does such cell surface moiety ligation lead to unexpectedly robust cell activation and proliferation in T-cells but can also be applied to magnifying the signal transduction event of many cell types. Thus the present invention could be used in combination with an implantable device to induce a signal transduction event in a particular location in the body, used to ex vivo stimulate cells for subsequent infusion into a patient, and used to substantially enhance the study of signal transduction events in cells by amplifying signal transduction signals, thereby aiding in screening for drugs that affect such transduction events (e.g., G-coupled protein receptors, related to schizophrenia, sleep, and other neurological indications; Fc fragment receptors on mast cells and basophils related to the allergic response). Accordingly, within the context of T-cells, the present invention provides a variety of unexpected advantages, first it eliminates the need for a separate monocyte-depletion step using "uncoated" particles, simplifies expansion of T-cells by requiring less cell transfers and less reagents, increased level of T-cell activation during activation process, reduces time and labor involved in the processing of the cells, reduces the cost of manufacturing, and increases the flexibility of scheduling patient processing and infusions.

In an additional aspect of the present invention, a first and second or more surfaces are utilized with or without ligands/agents bound thereto. In this embodiment, the various surfaces may have the same or different agents attached thereto for binding cell surface moieties of target cells. For example, a paramagnetic bead may have attached thereto an antibody for a receptor on a target cell and such beads may be mixed with a population of cells containing the target cell. Further, the cell population may be mixed with a second or more bead with the same or different cell surface moiety binding agents attached thereto. Upon force induced concentration, the beads and cells are brought together in a smaller volume and thus signaling is magnified. In another example, paramagnetic beads that have an agent specific for a carbohydrate or other non-receptor cell surface moiety attached thereto are mixed with a population of cells containing the target cell. A magnetic field is then used to draw the bead attached cells to another surface that has receptor ligating agents attached thereto. Thus, the signal transduction inducing agent is on the second surface. In yet another example, an agent that binds a cell surface moiety of target cell may be attached to a particle large enough to be retained in a mesh or filter that itself may have ligands attached thereto.

As noted above, the present invention provides methods for stimulating a cell population by simultaneously concentrating and binding moieties on the surfaces of the cells in that population. Contacting a cell population with an agent (e.g., a ligand) that binds to a cell surface moiety can stimulate the cell population. The ligand may be in solution but also may be attached to a surface. Ligation of cell surface moieties, such as a receptor, may generally induce a particular signaling pathway. Recent studies suggest that for signaling to occur, critical concentrations of lipid rafts containing the requisite receptors must aggregate. By way of example, raft aggregation may be facilitated in vivo or in vitro by attaching ligands for particular cell surface moieties to paramagnetic particles, exposing the ligand-bearing particles to the cells, and shortly thereafter or simultaneously applying a force, such as a magnetic field to assist polarizing the ligated moieties (e.g., receptors) and concentrating cells in a small volume. The application of a magnetic force concentrates the cells as well as concentrating the cells with the surface having agents attached thereto that ligate cell surface moieties, thereby bringing greater contact of the cells with the ligands, resulting in accelerated and more potent activation. Many applications of the present invention are possible, for example, if cells have low numbers of and/or dysfunctional receptors, the method may sufficiently concentrate such receptors in the lipid rafts to overcome such defects and to permit proper signaling activity. One example of such cell surface repertoire correction is in patients with certain types of leukemia, wherein prior to cell surface moiety stimulation with agents such as anti-CD3 and anti-CD28 antibodies several normal cell surface markers are unusually low, such as the CD3/TCR complex. By stimulating these cell populations with agents such as anti-CD3 and anti-CD28 antibodies, the cell surface markers of these cells return to a level that appears normal and as such can provide a more robust immunotherapy product for cancer therapy that provides a stronger and more rapid immune response when returned to the patient. In yet other applications of this invention, cells may be efficiently concentrated and activated, including inducing receptor polarization, thereby maximizing receptor signaling events. Such applications have broad utility including the use in screening assays directed at receptors or by collecting cellular rafts on the surface of a cell to induce activation such as inducing apoptosis by ligating Fas or like molecules in a tumor cell.

In one example of such screening assays, one could use G-coupled protein receptor bearing cells and contact them with agents that bind thereto, these agents being bound to a surface that allows force induced concentration. Accordingly, as the receptors raft together the signal transduction event would be amplified. This could be important in the study of signal transduction events that are very low level in typical experiments and thus screening for drug compounds to inhibit or somehow modify such signal transduction events.

Stimulation of a Cell Population

The methods of the present invention relates to the stimulation of a target cell by introducing a ligand or agent that binds to a cellular moiety, inducing a cellular event. Binding of the ligand or agent to the cell may trigger a signaling pathway that in turn activates particular phenotypic or biological changes in the cell The stimulation of a target cell by introducing a ligand or agent that binds to a cellular moiety as described herein may upregulate or downregulate any number of cellular processes leading to particular phenotypic or biological changes in the cell. The activation of the cell may enhance normal cellular functions or initiate normal cell functions in an abnormal cell. The method described herein provides stimulation by forcing concentration of the cells together with the ligand or agent that binds a cell surface moiety. Stimulation of a cell may be enhanced or a particular cellular event may be stimulated by introducing a second agent or ligand that ligates a second cell surface moiety. This method may be applied to any cell for which ligation of a cell surface moiety leads to a signaling event. The invention further provides means for selection or culturing the stimulated cells. The prototypic example described is stimulation of T-cells, but one of ordinary skill in the art will readily appreciate that the method may be applied to other cell types. By way of example, cell types that may be stimulated and selected include fibroblasts, neuroblasts, hematopoietic stem cells and hematopoietic progenitor cells ($CD34^+$ cells), mesenchymal stem cells, mesenchymal progenitor cells, neural and hepatic progenitor and stem cells, dendritic cells, cytolytic T-cells ($CD8^+$ cells), other leukocyte populations, pluripotent stem cells, multi-potent stem cells, islet cells, etc. Accordingly, the present invention also provides populations of cells resulting from this methodology as well as cell populations having distinct phenotypical characteristics, including T-cells with specific phenotypic characteristics.

As noted above a variety of cell types may be utilized within the context of the present invention. For example, cell types such as B cells, T-cells, NK cells, other blood cells, neuronal cells, glandular (endocrine) cells, bone forming cells (osteoclasts, etc.), germ cells (e.g., oocytes), epithelial cells lining reproductive organs, and others may be utilized. Cell surface moiety-ligand pairs could include (but not exclusively): T-cell antigen receptor (TCR) and anti-CD3 mAb, TCR and major histocompatibility complex (MHC)+ antigen, TCR and peptide-MHC tetramer, TCR and superantigens (e.g., staphylococcal enterotoxin B (SEB), toxic shock syndrome toxin (TSST), etc.), B cell antigen receptor (BCR) and anti-Ig, BCR and LPS, BCR and specific antigens (univalent or polyvalent), NK receptor and anti-NK receptor antibodies, FAS (CD95) receptor and FAS ligand, FAS receptor and anti-FAS antibodies, CD54 and anti-CD54 antibodies, CD2 and anti-CD2 antibodies, CD2 and LFA-3 (lymphocyte function related antigen-3), cytokine receptors and their respective cytokines, cytokine receptors and anti-cytokine receptor antibodies, TNF-R (tumor necrosis factor-receptor) family members and antibodies directed against them, TNF-R family members and their respective ligands, adhesion/homing receptors and their ligands, adhesion/homing receptors and antibodies against them, oocyte or fertilized oocyte receptors and their ligands, oocyte or fertilized oocyte receptors and antibodies against them, receptors on the endometrial lining of uterus and their ligands, hormone receptors and their respective hormone, hormone receptors and antibodies directed against them, and others.

The nature of the binding of a receptor by a ligand will either result in the multimerization of the receptors, or aggregation/orientation of the receptors, such that signaling or cell response is upregulated, downregulated, accelerated, improved, or otherwise altered so as to confer a particular benefit, such as cell division, cytokine secretion, cell migration, increased cell-cell interaction, etc.

Two examples are given below that illustrate how such a multimerization, aggregation, or controlled reorientation of cell surface moieties could be of practical benefit.

In one example, normal T-cell activation by antigen and antigen presenting cells usually results in aggregation of TCR rafts, cytoskeletal reorganization, polarization of "activation" signals and cell division, for example. Using man-made approaches, such as those described herein, in the absence of "normal" in-vivo T-cell activation, one could accelerate, improve, or otherwise affect the functions described above, in particular through the accelerated, controlled, and spatially oriented ligation of TCR and CD28. Benefits could be improved cell expansion in vitro resulting in higher numbers of infuseable and more robust cells for therapeutic applications. Other benefits could be improved receptor "aggregation" for cells with defects, such as lower-than-normal TCR density on the cell surface. Similarly, in vivo applications could be beneficial where specific T-cell populations need to be activated, such as tumor-specific T-cells at tumor sites. Improved receptor aggregation and orientation could provide an activation signal otherwise difficult to obtain for functionally tolerized T-cells. Further, such activation could be used within the context of antigen specific T-cells. In this regard T-cells from a tumor could be isolated and expanded and infused into the patient. Similarly, T-cells exposed to an antigen either in vivo or in vitro could be expanded by the present methodologies.

In another example, improved induction of cell death occurs via the FAS pathway: The ability to accelerate the multimerization of FAS, spatially orient "activated" FAS on target cell surfaces, or to promote a cumulative FAS ligation that would otherwise be unachievable, could provide significant benefit in vivo, particularly for treating cancer, autoimmune responses, or graft-versus-host disease. For example, a tumor cell may express low levels of FAS in vivo, and the host may express low levels of FAS-L at tumor sites (due to suppressive cytokines, etc.). Due to these low levels, an adequate FAS signal cannot be generated, allowing for tumor survival and growth. One possible way to overcome this FAS/FAS-ligand deficiency could be to target tumors/tumor sites with monovalent or multivalent ligands for FAS (FAS-L, antibodies, etc.), bound to paramagnetic particles. Application of a strong magnetic field using the present at tumor sites (e.g., melanoma, Kaposi's sarcoma, squamous cell neck carcinomas, etc.) could provide for the spacial orientation of the paramagnetic particles at tumor sites as the particles bound FAS on tumor cells, adapted for receptor activation and/or T-cell activation and expansion. Increased FAS aggregation accompanied by signal polarization might provide adequate signal to now induce cell death in the tumor cells.

In one particular embodiment of the invention, a T-cell population may be stimulated by simultaneously concentrating and ligating the surfaces of the T-cells. In one aspect of the present invention, antibodies to CD3 and CD28 are co-immobilized on a surface. A preferred surface for such immobilization includes particles, and in certain aspects, beads, such as paramagnetic beads. In another aspect of the present invention, any ligand that binds the TCR/CD3 complex and initiates a primary stimulation signal may be utilized as a primary activation agent immobilized on the surface. Any ligand that binds CD28 and initiates the CD28 signal transduction pathway, thus causing co-stimulation of the cell with a CD3 ligand and enhancing activation of a population of T-cells, is a CD28 ligand and accordingly, is a co-stimulatory agent within the context of the present invention. In a further aspect of the invention, a force is applied to the mixture of T-cells and anti-CD3 and anti-CD28-conjugated surfaces to concentrate the T-cells, thus maximizing T-cell surface ligation. While in one particular embodiment the concentration force is magnetic force applied where the anti-CD3 and anti-CD28 coated surfaces are paramagnetic beads, other means to bring the cells and the ligands together in a concentrated fashion are available in the art. Such methods of stimulating a T-cell population provides significant bead-cell and/or cell-cell contact that induces surprisingly greater activation and/or proliferation of T-cells. Furthermore, the inventive methods alter the cell surface marker profile wherein the activated T-cells express cell surface markers that indicate a more normal phenotype and less variable final product compared to the profile of the T-cells when first isolated from a subject with a disease.

The Primary Signal

The biochemical events responsible for ex vivo T-cell stimulation are set forth briefly below. Interaction between the TCR/CD3 complex and antigen presented in conjunction with either MHC class I or class II molecules on an antigen-presenting cell initiates a series of biochemical events termed antigen-specific T-cell activation. Accordingly, activation of T-cells can be accomplished by stimulating the T-cell TCR/CD3 complex or by stimulating the CD2 surface protein. An anti-CD3 monoclonal antibody can be used to activate a population of T-cells via the TCR/CD3 complex. A number of anti-human CD3 monoclonal antibodies are commercially available, exemplary are OKT3, prepared from hybridoma cells obtained from the American Type Culture Collection, and monoclonal antibody G19-4. Similarly, stimulatory forms of anti-CD2 antibodies are known and available. Stimulation through CD2 with anti-CD2 antibodies is typically accomplished using a combination of at least two different anti-CD2 antibodies. Stimulatory combinations of anti-CD2 antibodies that have been described include the following: the T11.3 antibody in combination with the T11.1 or T11.2 antibody (Meuer et al., *Cell* 36:897–906, 1984), and the 9.6 antibody (which recognizes the same epitope as T11.1) in combination with the 9-1 antibody (Yang et al., *J. Immunol.* 13 7:1097–1100, 1986). Other antibodies that bind to the same epitopes as any of the above described antibodies can also be used. Additional antibodies, or combinations of antibodies, can be prepared and identified by standard techniques.

A primary activation signal can also be delivered to a T-cell through other mechanisms. For example, a combination that may be used includes a protein kinase C (PKC) activator, such as a phorbol ester (e.g., phorbol myristate acetate), and a calcium ionophore (e.g., ionomycin, which raises cytoplasmic calcium concentrations), or the like. The use of such agents bypasses the TCR/CD3 complex but delivers a stimulatory signal to T-cells. Other agents acting as primary signals may include natural and synthetic ligands. A natural ligand may include MHC with or without a peptide presented. Other ligands may include, but are not limited to, a peptide, polypeptide, growth factor, cytokine, chemokine, glycopeptide, soluble receptor, steroid, hormone, mitogen, such as PHA, or other superantigens, peptide-MHC tetramers (Altman, et al., Science. 1996 Oct. 4;274(5284):94–6.) and soluble MHC dimers (Dal Porto, et al. Proc Natl Acad Sci USA 1993 Jul. 15;90). Within the context of the present invention, the use of concentration and stimulation may result in such high receptor polarization that no secondary signal is required to induce proliferation of T-cells.

In other embodiments, signal transduction events of any kind may be magnified or analyzed by utilizing the current invention. For example, G protein-coupled receptors may stimulated and measured using the concentration methods of the present invention.

The Secondary Signal

While stimulation of the TCR/CD3 complex or CD2 molecule appears to be required for delivery of a primary activation signal in a T-cell, a number of molecules on the surface of T-cells, termed accessory or co-stimulatory molecules, have been implicated in regulating the transition of a resting T-cell to blast transformation, and subsequent proliferation and differentiation. Thus, in addition to the primary activation signal, induction of T-cell responses requires a second, co-stimulatory signal. One such co-stimulatory or accessory molecule, CD28, is believed to initiate or regulate a signal transduction pathway that is distinct from any stimulated by the TCR complex.

Therefore, to enhance activation and proliferation of a population of T-cells in the absence of exogenous growth factors or accessory cells, an accessory molecule on the surface of the T-cell, such as CD28, is stimulated with a ligand that binds the accessory molecule. In one embodiment, stimulation of the accessory molecule CD28 and T-cell activation occur simultaneously by contacting a population of T-cells with a surface to which a ligand that binds CD3 and a ligand that binds CD28 are attached. Activation of the T-cells, for example, with an anti-CD3 antibody, and stimulation of the CD28 accessory molecule results in selective proliferation of $CD4^+$ T-cells.

Accordingly, one of ordinary skill in the art will recognize that any agent, including an anti-CD28 antibody or fragment thereof capable of cross-linking the CD28 molecule, or a natural ligand for CD28 can be used to stimulate T-cells. Exemplary anti-CD28 antibodies or fragments thereof useful in the context of the present invention include monoclonal antibody 9.3 ($IgG2_a$) (Bristol-Myers Squibb, Princeton, N.J.), monoclonal antibody KOLT-2 (IgG1), 15E8 (IgG1), 248.23.2 (IgM), and EX5.3D10 ($IgG2_a$) (ATCC HB11373). Exemplary natural ligands include the B7 family of proteins, such as B7-1 (CD80) and B7-2 (CD86) (Freedman et al., *J. Immunol.* 137:3260–3267, 1987; Freeman et al., *J. Immunol.* 143:2714–2722, 1989; Freeman et al., *J. Exp. Med.* 174:625–631, 1991; Freeman et al., *Science* 262:909–911, 1993; Azuma et al., *Nature* 366:76–79, 1993; Freeman et al., *J. Exp. Med.* 178:2185–2192, 1993). In addition, binding homologues of a natural ligand, whether native or synthesized by chemical or recombinant techniques, can also be used in accordance with the present invention. Other agents acting as secondary signals may include natural and synthetic ligands. Agents may include, but are not limited to, other antibodies or fragments thereof, a peptide, polypeptide, growth factor, cytokine, chemokine, glycopeptide, soluble receptor, steroid, hormone, mitogen, such as PHA, or other superantigens.

In a further embodiment of the invention, activation of a T-cell population may be enhanced by co-stimulation of other T-cell integral membrane proteins. For example, binding of the T-cell integrin LFA-1 to its natural ligand, ICAM-1, may enhance activation of cells. Another cell surface molecule that may act as a co-stimulator for T-cells is VCAM-1 (CD106) that binds very-late-antigen-4 (VLA-4) on T-cells.

One of skill in the art will appreciate that cells other than T-cells may be stimulated by binding of an agent that ligates a cell surface moiety and induces aggregation of the moiety, which in turn results in activation of a signaling pathway. Other such cell surface moieties include, but are not limited to, GPI-anchored folate receptor (CD59), human IgE receptor (FcεRi receptor), BCR, EGF receptor, insulin receptor, ephrin B1 receptor, neurotrophin, glial-cell derived neutrophic factor (GNDF), hedgehog and other cholesterol-linked and palmitoylated proteins, H-Ras, integrins, endothelial nitric oxide synthase (eNOS), FAS, members of the TNF receptor family, GPI-anchored proteins, doubly acylated proteins, such as the Src-family kinases, the alpha-subunit of heterotrimeric G proteins, and cytoskeletal proteins.

Expansion of T-Cell Population

In one aspect of the present invention, ex vivo T-cell expansion can be performed by isolation of T-cells and subsequent stimulation. In one embodiment of the invention, the T-cells may be stimulated by a single agent. In another embodiment, T-cells are stimulated with two agents, one that induces a primary signal and a second that is a co-stimulatory signal. Ligands useful for stimulating a single signal or stimulating a primary signal and an accessory molecule that stimulates a second signal may be used in soluble form, attached to the surface of a cell, or immobilized on a surface as described herein. A ligand or agent that is attached to a surface serves as a "surrogate" antigen presenting cell (APC). In a preferred embodiment both primary and secondary agents are co-immobilized on a surface. In one embodiment, the molecule providing the primary activation signal, such as a CD3 ligand, and the co-stimulatory molecule, such as a CD28 ligand, are coupled to the same surface, for example, a particle. Further, as noted earlier, one, two, or more stimulatory molecules may be used on the same or differing surfaces.

Prior to expansion, a source of T-cells is obtained from a subject. The term "subject" is intended to include living organisms in which an immune response can be elicited (e.g., mammals). Examples of subjects include humans, dogs, cats, mice, rats, and transgenic species thereof. T-cells can be obtained from a number of sources, including peripheral blood mononuclear cells, bone marrow, lymph node tissue, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as ficoll separation. In one preferred embodiment, cells from the circulating blood of an individual are obtained by apheresis or leukapheresis. The apheresis product typically contains lymphocytes, including T-cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor) according to the manufacturer's instructions. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T-cells are isolated from peripheral blood lymphocytes by lysing the red blood cells and depleting the monocytes, for example, by centrifugation through a PERCOLL™ gradient. A specific subpopulation of T-cells, such as $CD28^+$, $CD4^+$, $CD8^+$, $CD45RA^+$, and $CD45RO^+$ T-cells, can be further isolated by positive or negative selection techniques. For example, in one preferred embodiment, T-cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells.

Enrichment of a T-cell population by negative selection can be accomplished with a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g. particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g. particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one embodiment, the concentration of cells used is $5 \times 10^6$/ml. In other embodiments, the concentration used can be from about $1 \times 10^5$/ml to $1 \times 10^6$/ml, and any integer value in between.

With respect to monocyte depletion noted above, if desired or necessary, monocyte populations (i.e., $CD14^+$ cells) may be depleted from blood preparations prior to ex vivo expansion by a variety of methodologies, including anti-CD14 coated beads or columns, or utilization of the phagocytotic activity of these cells to facilitate removal. Accordingly, in one embodiment, the invention uses paramagnetic particles of a size sufficient to be engulfed by phagocytotic monocytes. In certain embodiments, the paramagnetic particles are commercially available beads, for example, those produced by Dynal AS under the trade name Dynabeads™. Exemplary Dynabeads™ in this regard are M-280, M-450, and M-500. In one aspect, other non-specific cells are removed by coating the paramagnetic particles with "irrelevant" proteins (e.g., serum proteins or antibodies). Irrelevant proteins and antibodies include those proteins and antibodies or fragments thereof that do not specifically target the T-cells to be expanded. In certain embodiments the irrelevant beads include beads coated with sheep anti-mouse antibodies, goat anti-mouse antibodies, and human serum albumin.

In brief, such depletion of monocytes is performed by preincubating PBMC isolated from whole blood or apheresed peripheral blood with one or more varieties of irrelevant or non-antibody coupled paramagnetic particles at any amount that allows for removal of monocytes (approximately a 20:1 bead:cell ratio) for about 30 minutes to 2 hours at 22 to 37 degrees C., followed by magnetic removal of cells which have attached to or engulfed the paramagnetic particles. Such separation can be performed using standard methods available in the art. For example, any magnetic separation methodology may be used including a variety of which are commercially available, (e.g., DYNAL® Magnetic Particle Concentrator (DYNAL MPC®)). Assurance of requisite depletion can be monitored by a variety of methodologies known to those of ordinary skill in the art, including flow cytometric analysis of CD14 positive cells, before and after said depletion.

T-cells for stimulation can also be frozen after the washing step, which does not require the monocyte-removal step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or other suitable cell freezing media, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

The cell population may be stimulated as described herein, such as by contact with an anti-CD3 antibody or an anti-CD2 antibody immobilized on a surface, or by contact with a protein kinase C activator (e.g., bryostatin) in conjunction with a calcium ionophore. For co-stimulation of an accessory molecule on the surface of the T-cells, a ligand that binds the accessory molecule is used. For example, a population of $CD4^+$ cells can be contacted with an anti-CD3 antibody and an anti-CD28 antibody, under conditions appropriate for stimulating proliferation of the T-cells. Similarly, to stimulate proliferation of $CD8^+$ T-cells, an anti-CD3 antibody and the anti-CD28 antibody B-T3, XR-CD28 (Diaclone, Besancon, France) can be used as can other methods commonly known in the art (Berg et al., *Transplant Proc.* 30(8):3975–3977, 1998; Haanen et al., *J. Exp. Med.* 190(9):1319–1328, 1999; Garland et al.,*J. Immunol Meth.* 227(1–2):53–63, 1999).

The primary stimulatory signal and the co-stimulatory signal for the T-cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing FC receptors or an antibody or other binding agent which will bind to the agents. In a preferred embodiment, the two agents are immobilized on beads, either on the same bead, i.e., "cis," or to separate beads, i.e., "trans." By way of example, the agent providing the primary activation signal is an anti-CD3 antibody and the agent providing the co-stimulatory signal is an anti-CD28 antibody; and both agents are co-immobilized to the same bead in equivalent molecular amounts. In one embodiment, a 1:1 ratio of each antibody bound to the beads for $CD4^+$ T-cell expansion and T-cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 0.5 to about 3 fold is observed as compared to the expansion oberserved using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e. the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T-cells or other target cells. As those of ordinary skill in the art can readily appreciate, the ratio of particle to cells may dependant on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T-cells. The ratio of anti-CD3- and anti-CD28-coupled particles to T-cells that result in T-cell stimulation can vary as noted above, however certain preferred values include at least 1:5, 1:4, 1:3, 1:2, 1:1, 2:1, 3:1, 4:1 to 6:1, with one preferred ratio being at least 1:1 particles per T-cell. In one embodiment, a ratio of particles to cells of 1:1 or less is used. In further embodiments, the ratio of particles to cells can be varied depending on the day of stimulation. For example, in one embodiment, the ratio of particles to cells is from 1:0 to 10:1 on the first day and additional particles are added to the cells every day or every other day thereafter for up to 10 days, at final ratios of from 1:1 to 1:0 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

Using certain methodologies it may be advantageous to maintain long-term stimulation of a population of T-cells following the initial activation and stimulation, by separating the T-cells from the stimulus after a period of about 12 to about 14 days. The rate of T-cell proliferation is monitored periodically (e.g., daily) by, for example, examining the size or measuring the volume of the T-cells, such as with a Coulter Counter. In this regard, a resting T-cell has a mean diameter of about 6.8 microns, and upon initial activation and stimulation, in the presence of the stimulating ligand, the T-cell mean diameter will increase to over 12 microns by day 4 and begin to decrease by about day 6. When the mean T-cell diameter decreases to approximately 8 microns, the T-cells may be reactivated and re-stimulated to induce further proliferation of the T-cells. Alternatively, the rate of T-cell proliferation and time for T-cell re-stimulation can be monitored by assaying for the presence of cell surface molecules, such as, CD154, CD54, CD25, CD137, CD134, which are induced on activated T-cells.

For inducing long-term stimulation of a population of $CD4^+$ and/or $CD8^+$ T-cells, it may be necessary to reactivate and re-stimulate the T-cells with a stimulatory agent such as an anti-CD3 antibody and an anti-CD28 antibody (such as B-T3, XR-CD28 (Diaclone, Besancon, France) or monoclonal antibody ES5.2D8 several times to produce a population of $CD4^+$ or $CD8^+$ cells increased in number from about 10 to about 1,000-fold the original T-cell population. For example, in one embodiment of the present invention, T-cells are stimulated as described in Example 1 for 2–3 times. In further embodiments, T-cells are stimulated as described in Example 1 for 4 or 5 times. Using the present methodology, it is possible to achieve T-cell numbers from about 100 to about 100,000-fold. Moreover, as described in EXAMPLE XII, T-cells expanded by the method of the present invention secrete high levels of cytokines (e.g., IL-2, IFN-γ, IL-4, GM-CSF and TNF-α) into the culture supernatants. For example, as compared to stimulation with IL-2, CD4+ T-cells expanded by use of anti-CD3 and anti-CD28 co-stimulation secrete high levels of GM-CSF and TNF-α into the culture medium. These cytokines can be purified from the culture supernatants or the supernatants can be used directly for maintaining cells in culture. Similarly, the T-cells expanded by the method of the present invention together with the culture supernatant and cytokines can be administered to support the growth of cells in vivo.

In one embodiment, T-cell stimulation is performed with anti-CD3 and anti-CD28 antibodies co-immobilized on beads (3×28 beads), for a period of time sufficient for the cells to return to a quiescent state (low or no proliferation) (approximately 8–14 days after initial stimulation). The stimulation signal is then removed from the cells and the cells are washed and infused back into the patient. The cells at the end of the stimulation phase are rendered "super-inducible" by the methods of the present invention, as demonstrated by their ability to respond to antigens and the ability of these cells to demonstrate a memory-like phenotype, as is evidence by the examples. Accordingly, upon re-stimulation either exogenously or by an antigen in vivo after infusion, the activated T-cells demonstrate a robust response characterized by unique phenotypic properties, such as sustained CD154 expression and increased cytokine production.

In further embodiments of the present invention, the cells, such as T-cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, resulting in cell surface moiety ligation, thereby inducing cell stimulation.

By way of example, when T-cells are the target cell population, the cell surface moieties may be ligated by allowing paramagnetic beads to which anti-CD3 and anti-CD28 are attached (3×28 beads) to contact the T-cells. In one embodiment the cells (for example, $10^4$ to $10^9$ T-cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e. 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and particles, interactions between particles and cells is minimized. This selects for cells that express high amounts of desired antigens to be bound to the particles. For example, CD4+ T cells express higher levels of CD28 and are more efficiently captured and stimulated than CD8+ T cells in dilute concentrations. In one embodiment, the concentration of cells used is about $5 \times 10^6$/ml. In other embodiments, the concentration used can be from about $1 \times 10^5$/ml to about $1 \times 10^6$/ml, and any integer value in between.

The buffer that the cells are suspended in may be any that is appropriate for the particular cell type. When utilizing certain cell types the buffer may contain other components, e.g. 1–5% serum, necessary to maintain cell integrity during the process. In another embodiment, the cells and beads may be combined in cell culture media. The cells and beads may be mixed, for example, by rotation, agitation or any means for mixing, for a period of time ranging from one minute to several hours. The container of beads and cells is then concentrated by a force, such as placing in a magnetic field. Media and unbound cells are removed and the cells attached to the beads are washed, for example, by pumping via a peristaltic pump, and then resuspended in media appropriate for cell culture.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T-cells are cultured together for about eight days. In another embodiment, the beads and T-cells are cultured together for 2–3 days. As described above, several cycles of stimulation may also be desired such that culture time of T cells can be 60 days or more. Conditions appropriate for T-cell culture include an appropriate media (e.g., Minimal Essential Media or RPMI Media 1640 or, X-vivo 15, (BioWhittaker)) that may contain factors necessary for proliferation and viability, including serum (e.g., fetal bovine or human serum), interleukin-2 (IL-2), insulin, or any other additives for the growth of cells known to the skilled artisan. Media can include RPMI 1640, AIM-V, DMEM, MEM, α-MEM, F-12, X-Vivo 15, and X-Vivo 20, with added amino acids and vitamins, either serum-free or supplemented with an appropriate amount of serum (or plasma) or a defined set of hormones, and/or an amount of cytokine(s) sufficient for the growth and expansion of T-cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

When using a magnetic field as the concentrating force the magnetic field strength applied to the cells prior to cell culture may be between the range of 200 gauss to 12,000 gauss on the magnetic surface. The shape and size of the magnet may be adapted to the size and shape of the mixing or cell culture vessels or to any other parameter that facilitates or increases cell to cell contact and concentration of the cells. The magnetic force may be diffused by placing a material that acts as a buffer or spacer between the magnet and the paramagnetic beads contained within the mixture with cells. A strong magnetic force is generally considered to be at least 7500 gauss at the surface, whereas a weak magnetic force is considered to be in the range of 2000–2500 gauss at the surface. The approximate magnetic force applied by a magnet on a paramagnetic bead depends upon the volume of the paramagnetic bead and the magnetic field strength according to the following formula:

$$F_{mag}=(v)(\psi)(B)(dB/dx)$$

where $F_{mag}$ equals the magnetic force, v equals the volume of the paramagnetic bead, $\psi$ equals the magnetic susceptibility of a paramagnetic bead (a value provided by the manufacturer), B equals the magnetic field strength, and (dB/dx) equals the field strength gradient. One of skill in the art will appreciate that the factors on the right-hand side of the equation can be obtained or measured, allowing the magnetic force applied to be calculated.

Cells stimulated by the methods of the present invention are activated as shown by the induction of signal transduction, expression of cell surface markers and/or proliferation. One such marker appropriate for T-cells is CD154 which is an important immunomodulating molecule, The expression of CD154 is extremely beneficial in amplifying the immune response. CD154 interacts with the CD40 molecule expressed on many B cells, dendritic cells, monocytes, and some endothelial cells. Accordingly, this unexpected and surprising increase in CD154 expression is likely to lead to more efficacious T-cell compositions. Stimulation of $CD3^+$ cells as described herein provides T-cells that express a 1.1 to 20-fold increases in the levels of certain cell surface markers such as CD154 expression on days 1, 2, 3, or 4 following stimulation. (See EXAMPLE 5, Table 2 and FIG. 4.) Expression of another cell surface marker, CD25, also was greater on T-cells after concentration and stimulation than on cells prior to culture or cells stimulated by other methods. (See Table 2.)

One of skill in the art will appreciate that any target cell that can be stimulated by cell surface moiety ligation may be combined with the agent-coated surface, such as beads. Further, the agent-coated surfaces, such as, beads may be separated from the cells prior to culture, at any point during culture, or at the termination of culture. In addition, the agent-coated surfaces ligated to the target cells may be separated from the non-binding cells prior to culture or the other cells may remain in culture as well. In one embodiment, prior to culture, the agent-coated beads and target cells are not separated but are cultured together. In a further embodiment, the beads and target cells are first concentrated by application of a force, resulting in cell surface moiety ligation, thereby inducing stimulation and subsequent activation.

Also contemplated by this invention, are other means to increase the concentration of the target cells, for example, a T-cell fraction bound to a surface coated with primary and secondary stimulatory molecules. In addition to application of a magnetic force, other forces greater than gravitational force may be applied, for example, but not limited to, centrifugal force, transmembrane pressure, and a hydraulic force. Concentration may also be accomplished by filtration.

One of skill in the art will readily appreciate that contact between the agent-coated beads and the cells to be stimulated can be increased by concentration using other forces. Accordingly, any means for concentrating cells with cell surface moiety binding ligands will be sufficient as long as the concentration brings together cells and agents in a manner that exceeds gravity or diffusion.

It should be understood that in various embodiments the agent-coated surface may be a particle, such as a bead which is mixed with the cells and concentrated in a small volume in a magnetic field, thus drawing all the particles and particle bound cells into a defined and concentrated area. In certain embodiments, the agent-coated surface may be drawn together by force within thirty seconds to four hours of being exposed to the target cells. In other embodiments the time may be from 1 minute to 2 hours, or all integer ranges in between. Application of a force to a cell population with receptor bearing cells that is mixed with a surface to which at least one cell surface ligand is attached may induce cell receptor polarization, aggregating cell surface molecules. This means for inducing cell surface polarization may enhance signaling within the cell by aggregating cell surface molecules that comprise lipid rafts. Such aggregation can induce a signal pathway, which may lead to down-regulation or suppression of a cellular event. Alternatively, the aggregation of cell surface molecules may lead to up-regulation or activation of a cellular event.

A cellular event may include, for example, receptor-mediated signal transduction that induces or suppresses a particular pathway, including an apoptotic pathway, or induces phosphorylation of proteins, or stimulates or suppresses growth signals. In one embodiment, the cells may be lymphocytes, particularly a T-cell, and the cell surface ligand may be an anti-CD3 antibody attached to a surface, for example, a particle. The particle may be a paramagnetic bead and the force applied a magnetic force. Application of a magnetic force to a mixture of the lymphocytes and anti-CD3-coated surface of the paramagnetic bead may cause the CD3 receptors of the T-cell to polarize more quickly than would occur in the absence of an external force. This method of stimulating the T-cell promotes more rapid activation of the T-cell immune response pathways and proliferation of cells.

In another embodiment, the time of exposure to stimulatory agents such as anti-CD3/anti-CD28 (i.e., 3×28)-coated beads may be modified or tailored to obtain a desired T-cell phenotype. Alternatively, a desired population of T-cells can be selected using any number of selection techniques, prior to stimulation. One may desire a greater population of helper T-cells ($T_H$), typically $CD4^+$ as opposed to $CD8^+$ cytotoxic or regulatory T-cells, because an expansion of $T_H$ cells could improve or restore overall immune responsiveness. While many specific immune responses are mediated by $CD8^+$ antigen-specific T-cells, which can directly lyse or kill target cells, most immune responses require the help of $CD4^+$ T-cells, which express important immune-regulatory molecules, such as GM-CSF, CD40L, and IL-2, for example. Where CD4-mediated help if preferred, a method, such as that described herein, which preserves or enhances the CD4:CD8 ratio could be of significant benefit. Increased numbers of $CD4^+$ T-cells can increase the amount of cell-expressed CD40L introduced into patients, potentially improving target cell visibility (improved APC function). Similar effects can be seen by increasing the number of infused cells expressing GM-CSF, or IL-2, all of which are expressed predominantly by $CD4^+$ T-cells. Alternatively, in situations where CD4-help is needed less and increased numbers of $CD8^+$ T-cells are desirous, the XCELLERATE approaches described herein can also be utilized, by for example, pre-selecting for $CD8^+$ cells prior to stimulation and/or culture. Such situations may exist where increased levels of IFN-γ or increased cytolysis of a target cell is preferred.

To effectuate isolation of different T-cell populations, exposure times to the to the particles may be varied. For example, in one preferred embodiment, T-cells are isolated by incubation with 3×28 beads, such as Dynabeads M-450, for a time period sufficient for positive selection of the desired T cells. In one embodiment, the time period is about 30 minutes. In a further embodiment, the time period is at least 1, 2, 3, 4, 5, or 6 hours. In yet another preferred embodiment, the time period is 10 to 24 hours or more. In one preferred embodiment, the incubation time period is 24 hours. For isolation of T cells from cancer patients, use of longer incubation times, such as 24 hours, can increase cell yield.

To effectuate isolation of different T-cell populations, exposure times to the concentration force may be varied or pulsed. For example when such force is a magnet, exposure to the magnet or the magnetic field strength may be varied, and/or expansion times may be varied to obtain the specific phenotype of interest. The expression of a variety of phenotypic markers change over time; therefore, a particular time point may be chosen to obtain a specific population of T-cells. Accordingly, depending on the cell type to be stimulated, the stimulation and/or expansion time may be 10 weeks or less, 8 weeks or less, four weeks or less, 2 weeks or less, 10 days or less, or 8 days or less (four weeks or less includes all time ranges from 4 weeks down to 1 day (24 hours) or any value between these numbers). In some embodiments in may be desirable to clone T cells using, for example, limiting dilution or cell sorting, wherein longer stimulation time may be necessary. In some embodiments, stimulation and expansion may be carried out for 6 days or less, 4 days or less, 2 days or less, and in other embodiments for as little as 24 or less hours, and preferably 4–6 hours or less (these ranges include any integer values in between). When stimulation of T-cells is carried out for shorter periods of time, the population of T-cells may not increase in number as dramatically, but the population will provide more robust and healthy activated T-cells that can continue to proliferate in vivo and more closely resemble the natural effector T-cell pool. As the availability of T-cell help is often the limiting factor in antibody responses to protein antigens, the ability to selectively expand or selectively infuse a CD4$^+$ rich population of T-cells into a subject is extremely beneficial. Further benefits of such enriched populations are readily apparent in that activated helper T-cells that recognize antigens presented by B lymphocytes deliver two types of stimuli, physical contact and cytokine production, that result in the proliferation and differentiation of B cells.

T-cells that have been exposed to varied stimulation times may exhibit different characteristics. For example, typical blood or apheresed peripheral blood mononuclear cell products have a helper T-cell population($T_H$, CD4$^+$) that is greater than the cytotoxic or suppressor T-cell population ($T_C$, CD8$^+$). Ex vivo expansion of T-cells by stimulating CD3 and CD28 receptors produces a population of T-cells that prior to about days 8–9 consists predominately of $T_H$ cells, while after about days 8–9, the population of T-cells comprises an increasingly greater population of $T_C$ cells. Accordingly, depending on the purpose of treatment, infusing a subject with a T-cell population comprising predominately of $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T-cell product for specific purposes.

In one such example, among the important phenotypic markers that reproducibly vary with time are the high affinity IL-2 receptor (CD25), CD40 ligand (CD154), and CD45RO (a molecule that by preferential association with the TCR may increase the sensitivity of the TCR to antigen binding). As one of ordinary skill in the art readily appreciates, such molecules are important for a variety of reasons. For example, CD25 constitutes an important part of the autocrine loop that allows rapid T-cell division. CD154 has been shown to play a key role in stimulating maturation of the antigen-presenting dendritic cells; activating B-cells for antibody production; regulating $T_H$ cell proliferation; enhancing $T_C$ cell differentiation; regulating cytokine secretion of both $T_H$ cells and antigen-presenting cells; and stimulating expression of co-stimulatory ligands, including CD80, CD86, and CD154.

Cytokine production peaks in the first few days of the ex vivo expansion process. Accordingly, because cytokines are known to be important for mediating T-cell activation and function as well as immune response modulation, such cytokines are likely critical in the development of a therapeutic T-cell product, that is able to undergo reactivation upon contact with an additional antigen challenge. Cytokines important in this regard, include, but are not limited to, IL-2, IL-4, TNF-α, and IFN-γ. Thus, by obtaining a population of T-cells during the first few days of expansion and infusing these cells into a subject, a therapeutic benefit may occur in which additional activation and expansion of T-cells in vivo occurs.

In addition to the cytokines and the markers discussed previously, expression of adhesion molecules known to be important for mediation of T-cell activation and immune response modulation also change dramatically but reproducibly over the course of the ex vivo expansion process. For example, CD62L is important for homing of T-cells to lymphoid tissues and trafficking T-cells to sites of inflammation. Under certain circumstances of disease and injury, the presence of activated T-cells at these sites may be disadvantageous. Because down-regulation of CD62L occurs early following activation, the T-cells could be expanded for shorter periods of time. Conversely, longer periods of time in culture would generate a T-cell population with higher levels of CD62L and thus a higher ability to target the activated T-cells to these sites under other preferred conditions. Another example of a polypeptide whose expression varies over time is CD49d, an adhesion molecule that is involved in trafficking lymphocytes from blood to tissues spaces at sites of inflammation. Binding of the CD49d ligand to CD49d also allows the T-cell to receive co-stimulatory signals for activation and proliferation through binding by VCAM-1 or fibronectin ligands. The expression of the adhesion molecule CD54, involved in T-cell-APC and T-cell-T-cell interactions as well as homing to sites of inflammation, also changes over the course of expansion. Accordingly, T-cells could be stimulated for selected periods of time that coincide with the marker profile of interest and subsequently collected and infused. Thus, T-cell populations could be tailored to express the markers believed to provide the most therapeutic benefit for the indication to be treated.

In the various embodiments, one of ordinary skill in the art understands removal of the stimulation signal from the cells is dependent upon the type of surface used. For example, if paramagnetic beads are used, then magnetic separation is the feasible option. Separation techniques are described in detail by paramagnetic bead manufacturers' instructions (for example, DYNAL Inc., Oslo, Norway). Furthermore, filtration may be used if the surface is a bead large enough to be separated from the cells. In addition, a variety of transfusion filters are commercially available, including 20 micron and 80 micron transfusion filters (Baxter). Accordingly, so long as the beads are larger than the mesh size of the filter, such filtration is highly efficient. In a related embodiment, the beads may pass through the filter, but cells may remain, thus allowing separation. In one particular embodiment the biocompatible surface used degrades (i.e. biodegradable) in culture during the exposure period.

Although the antibodies used in the methods described herein can be readily obtained from public sources, such as the ATCC, antibodies to T-cell accessory molecules and the CD3 complex can be produced by standard techniques. Methodologies for generating antibodies for use in the methods of the invention are well-known in the art and are discussed in further detail herein.

Ligand Immobilization on a Surface

As indicated above, the methods of the present invention preferably use ligands bound to a surface. The surface may be any surface capable of having a ligand bound thereto or integrated into and that is biocompatible, that is, substantially non-toxic to the target cells to be stimulated. The biocompatible surface may be biodegradable or non-biodegradable. The surface may be natural or synthetic, and a synthetic surface may be a polymer. The surface may comprise collagen, purified proteins, purified peptides, polysaccharides, glycosaminoglycans, or extracellular matrix compositions. A polysaccharide may include for example, cellulose, agarose, dextran, chitosan, hyaluronic acid, or alginate. Other polymers may include polyesters, polyethers, polyanhydrides, polyalkylcyanoacryllates, polyacrylamides, polyorthoesters, polyphosphazenes, polyvinylacetates, block copolymers, polypropylene, polytetrafluorethylene (PTFE), or polyurethanes. The polymer may be lactic acid or a copolymer. A copolymer may comprise lactic acid and glycolic acid (PLGA). Non-biodegradable surfaces may include polymers, such as poly (dimethylsiloxane) and poly(ethylene-vinyl acetate). Biocompatible surfaces include for example, glass (e.g., bioglass), collagen, metal, hydroxyapatite, aluminate, bioceramic materials, hyaluronic acid polymers, alginate, acrylic ester polymers, lactic acid polymer, glycolic acid polymer, lactic acid/glycolic acid polymer, purified proteins, purified peptides, or extracellular matrix compositions. Other polymers comprising a surface may include glass, silica, silicon, hydroxyapatite, hydrogels, collagen, acrolein, polyacrylamide, polypropylene, polystyrene, nylon, or any number of plastics or synthetic organic polymers, or the like. The surface may comprise a biological structure, such as a liposome or a cell. The surface may be in the form of a lipid, a plate, bag, pellet, fiber, mesh, or particle. A particle may include, a colloidal particle, a microsphere, nanoparticle, a bead, or the like. In the various embodiments, commercially available surfaces, such as beads or other particles, are useful (e.g., Miltenyi Particles, Miltenyi Biotec, Germany; Sepharose beads, Pharmacia Fine Chemicals, Sweden; DYNABEADS™, Dynal Inc., New York; PURABEADS™, Prometic Biosciences).

When beads are used, the bead may be of any size that effectuates target cell stimulation. In one embodiment, beads are preferably from about 5 nanometers to about 500 µm in size. Accordingly, the choice of bead size depends on the particular use the bead will serve. For example, if the bead is used for monocyte depletion, a small size is chosen to facilitate monocyte ingestion (e.g., 2.8 µm and 4.5 µm in diameter or any size that may be engulfed, such as nanometer sizes); however, when separation of beads by filtration is desired, bead sizes of no less than 50 µm are typically used. Further, when using paramagnetic beads, the beads typically range in size from about 2.8 µm to about 500 µm and more preferably from about 2.8 µm to about 50 µm. Lastly, one may choose to use super-paramagnetic nanoparticles which can be as small as about $10^{-5}$ nm. Accordingly, as is readily apparent from the discussion above, virtually any particle size may be utilized.

An agent may be attached or coupled to, or integrated into a surface by a variety of methods known and available in the art. The agent may be a natural ligand, a protein ligand, or a synthetic ligand. The attachment may be covalent or noncovalent, electrostatic, or hydrophobic and may be accomplished by a variety of attachment means, including for example, chemical, mechanical, enzymatic, electrostatic, or other means whereby a ligand is capable of stimulating the cells. For example, the antibody to a ligand first may be attached to a surface, or avidin or streptavidin may be attached to the surface for binding to a biotinylated ligand. The antibody to the ligand may be attached to the surface via an anti-idiotype antibody. Another example includes using protein A or protein G, or other non-specific antibody binding molecules, attached to surfaces to bind an antibody. Alternatively, the ligand may be attached to the surface by chemical means, such as cross-linking to the surface, using commercially available cross-linking reagents (Pierce, Rockford, Ill.) or other means. In certain embodiments, the ligands are covalently bound to the surface. Further, in one embodiment, commercially available tosyl-activated DYNABEADS™ or DYNABEADS™ with epoxy-surface reactive groups are incubated with the polypeptide ligand of interest according to the manufacturer's instructions. Briefly, such conditions typically involve incubation in a phosphate buffer from pH 4 to pH 9.5 at temperatures ranging from 4 to 37 degrees C.

In one aspect, the agent, such as certain ligands may be of singular origin or multiple origins and may be antibodies or fragments thereof while in another aspect, when utilizing T-cells, the co-stimulatory ligand is a B7 molecule (e.g., B7-1, B7-2). These ligands are coupled to the surface by any of the different attachment means discussed above. The B7 molecule to be coupled to the surface may be isolated from a cell expressing the co-stimulatory molecule, or obtained using standard recombinant DNA technology and expression systems that allow for production and isolation of the co-stimulatory molecule(s) as described herein. Fragments, mutants, or variants of a B7 molecule that retain the capability to trigger a co-stimulatory signal in T-cells when coupled to the surface of a cell can also be used. Furthermore, one of ordinary skill in the art will recognize that any ligand useful in the activation and induction of proliferation of a subset of T-cells may also be immobilized on beads or culture vessel surfaces or any surface. In addition, while covalent binding of the ligand to the surface is one preferred methodology, adsorption or capture by a secondary monoclonal antibody may also be used. The amount of a particular ligand attached to a surface may be readily determined by flow cytometric analysis if the surface is that of beads or determined by enzyme-linked immunosorbent assay (ELISA) if the surface is a tissue culture dish, mesh, fibers, bags, for example.

In a particular embodiment, the stimulatory form of a B7 molecule or an anti-CD28 antibody or fragment thereof is attached to the same solid phase surface as the agent that stimulates the TCR/CD3 complex, such as an anti-CD3 antibody. In addition to anti-CD3 antibodies, other antibodies that bind to receptors that mimic antigen signals may be used. For example, the beads or other surfaces may be coated with combinations of anti-CD2 antibodies and a B7 molecule and in particular anti-CD3 antibodies and anti-CD28 antibodies.

When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In a preferred embodiment, the two agents are immobilized on beads, either on the same bead, i.e., "cis," or to separate beads, i.e., "trans." By way of example, the agent providing the primary activation signal is an anti-CD3 antibody and the agent providing the co-stimulatory signal is an anti-CD28 antibody; and both agents are co-immobilized to the same bead in equivalent molecular amounts. In one embodiment, a 1:1 ratio of each antibody bound to the beads for $CD4^+$ T-cell expansion and T-cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 0.5 to about 3 fold is observed as compared to the expansion oberserved using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e. the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Agents

Agents contemplated by the present invention include protein ligands, natural ligands, and synthetic ligands. Agents that can bind to cell surface moieties, and under certain conditions, cause ligation and aggregation that leads to signalling include, but are not limited to, lectins (for example, PHA, lentil lectins, concanavalin A), antibodies, antibody fragments, peptides, polypeptides, glycopeptides, receptors, B cell receptor and T-cell receptor ligands, extracellular matrix components, steroids, hormones (for example, growth hormone, corticosteroids, prostaglandins, tetra-iodo thyronine), bacterial moieties (such as lipopolysaccharides), mitogens, antigens, superantigens and their derivatives, growth factors, cytokine, viral proteins (for example, HIV gp-120), adhesion molecules (such as, L-selectin, LFA-3, CD54, LFA-1), chemokines, and small molecules. The agents may be isolated from natural sources such as cells, blood products, and tissues, or isolated from cells propogated in vitro, or prepared recombinantly, or by other methods known to those with skill in the art.

In one aspect of the present invention, when it is desirous to stimulate T-cells, useful agents include ligands that are capable of binding the CD3/TCR complex, CD2, and/or CD28 and initiating activation or proliferation, respectively. Accordingly, the term ligand includes those proteins that are the "natural" ligand for the cell surface protein, such as a B7 molecule for CD28, as well as artificial ligands such as antibodies directed to the cell surface protein. Such antibodies and fragments thereof may be produced in accordance with conventional techniques, such as hybridoma methods and recombinant DNA and protein expression techniques. Useful antibodies and fragments may be derived from any species, including humans, or may be formed as chimeric proteins, which employ sequences from more than one species.

Methods well known in the art may be used to generate antibodies, polyclonal antisera, or monoclonal antibodies that are specific for a ligand. Antibodies also may be produced as genetically engineered immunoglobulins (Ig) or Ig fragments designed to have desirable properties. For example, by way of illustration and not limitation, antibodies may include a recombinant IgG that is a chimeric fusion protein having at least one variable (V) region domain from a first mammalian species and at least one constant region domain from a second distinct mammalian species. Most commonly, a chimeric antibody has murine variable region sequences and human constant region sequences. Such a murine/human chimeric immunoglobulin may be "humanized" by grafting the complementarity determining regions (CDRs), which confer binding specificity for an antigen, derived from a murine antibody into human-derived V region framework regions and human-derived constant regions. Fragments of these molecules may be generated by proteolytic digestion, or optionally, by proteolytic digestion followed by mild reduction of disulfide bonds and alkylation, or by recombinant genetic engineering techniques.

Antibodies are defined to be "immunospecific" if they specifically bind the ligand with an affinity constant, $K_a$, of greater than or equal to about $10^4$ $M^{-1}$, preferably of greater than or equal to about $10^5$ $M^{-1}$, more preferably of greater than or equal to about $10^6$ $M^{-1}$, and still more preferably of greater than or equal to about $10^7$ $M^{-1}$. Affinities of binding partners or antibodies can be readily determined using conventional techniques, for example, those described by Scatchard et al. (*Ann. N.Y. Acad. Sci. USA* 51:660, 1949) or by surface plasmon resonance (BIAcore, Biosensor, Piscataway, N.J.) See, e.g., Wolff et al., *Cancer Res.*, 53:2560–2565, 1993).

Antibodies may generally be prepared by any of a variety of techniques known to those having ordinary skill in the art (See, e.g., Harlow et al., *Antibodies: A Laboratory Manual*, 1988, Cold Spring Harbor Laboratory). In one such technique, an animal is immunized with the ligand as antigen to generate polyclonal antisera. Suitable animals include rabbits, sheep, goats, pigs, cattle, and may include smaller mammalian species, such as, mice, rats, and hamsters.

An immunogen may be comprised of cells expressing the ligand, purified or partially purified ligand polypeptides or variants or fragments thereof, or ligand peptides. Ligand peptides may be generated by proteolytic cleavage or may be chemically synthesized. Peptides for immunization may be selected by analyzing the primary, secondary, or tertiary structure of the ligand according to methods know to those skilled in the art in order to determine amino acid sequences more likely to generate an antigenic response in a host animal (See, e.g., Novotny, *Mol. Immunol.* 28:201–207, 1991; Berzoksky, *Science* 229:932–40, 1985).

Preparation of the immunogen may include covalent coupling of the ligand polypeptide or variant or fragment thereof, or peptide to another immunogenic protein, such as, keyhole limpet hemocyanin or bovine serum albumin. In addition, the peptide, polypeptide, or cells may be emulsified in an adjuvant (See Harlow et al., *Antibodies: A Laboratory Manual,* 1988 Cold Spring Harbor Laboratory). In general, after the first injection, animals receive one or more booster immunizations according to a preferable schedule for the animal species. The immune response may be monitored by periodically bleeding the animal, separating the sera, and analyzing the sera in an immunoassay, such as an Ouchterlony assay, to assess the specific antibody titer. Once an antibody titer is established, the animals may be bled periodically to accumulate the polyclonal antisera. Polyclonal antibodies that bind specifically to the ligand polypeptide or peptide may then be purified from such antisera, for example, by affinity chromatography using protein A or using the ligand polypeptide or peptide coupled to a suitable solid support.

Monoclonal antibodies that specifically bind ligand polypeptides or fragments or variants thereof may be prepared, for example, using the technique of Kohler and Milstein (*Nature,* 256:495–497, 1975; *Eur. J. Immunol.* 6:511–519, 1976) and improvements thereto. Hybridomas, which are immortal eucaryotic cell lines, may be generated that produce antibodies having the desired specificity to a the ligand polypeptide or variant or fragment thereof. An animal—for example, a rat, hamster, or preferably mouse—is immunized with the ligand immunogen prepared as described above. Lymphoid cells, most commonly, spleen cells, obtained from an immunized animal may be immortalized by fusion with a drug-sensitized myeloma cell fusion partner, preferably one that is syngeneic with the immunized animal. The spleen cells and myeloma cells may be combined for a few minutes with a membrane fusion-promoting agent, such as polyethylene glycol or a nonionic detergent, and then plated at low density on a selective medium that supports the growth of hybridoma cells, but not myeloma cells. A preferred selection media is HAT (hypoxanthine, aminopterin, thymidine). After a sufficient time, usually about 1 to 2 weeks, colonies of cells are observed. Single colonies are isolated, and antibodies produced by the cells may be tested for binding activity to the ligand polypeptide or variant or fragment thereof. Hybridomas producing antibody with high affinity and specificity for the ligand antigen are preferred. Hybridomas that produce monoclonal antibodies that specifically bind to a ligand polypeptide or variant or fragment thereof are contemplated by the present invention.

Monoclonal antibodies may be isolated from the supernatants of hybridoma cultures. An alternative method for production of a murine monoclonal antibody is to inject the hybridoma cells into the peritoneal cavity of a syngeneic mouse. The mouse produces ascites fluid containing the monoclonal antibody. Contaminants may be removed from the antibody by conventional techniques, such as chromatography, gel filtration, precipitation, or extraction.

Human monoclonal antibodies may be generated by any number of techniques. Methods include but are not limited to, Epstein Barr Virus (EBV) transformation of human peripheral blood cells (see, U.S. Pat. No. 4,464,456), in vitro immunization of human B cells (see, e.g., Boerner et al., *J. Immunol.* 147:86–95, 1991), fusion of spleen cells from immunized transgenic mice carrying human immunoglobulin genes and fusion of spleen cells from immunized transgenic mice carrying immunoglobulin genes inserted by yeast artificial chromosome (YAC) (see, e.g., U.S. Pat. No. 5,877, 397; Bruggemann et al., *Curr. Opin. Biotechnol.* 8:455–58, 1997; Jakobovits et al., *Ann. N. Y. Acad. Sci.* 764:525–35, 1995), or isolation from human immunoglobulin V region phage libraries.

Chimeric antibodies and humanized antibodies for use in the present invention may be generated. A chimeric antibody has at least one constant region domain derived from a first mammalian species and at least one variable region domain derived from a second distinct mammalian species (See, e.g., Morrison et al, *Proc. Natl. Acad. Sci. USA,* 81:6851–55, 1984). Most commonly, a chimeric antibody may be constructed by cloning the polynucleotide sequences that encode at least one variable region domain derived from a non-human monoclonal antibody, such as the variable region derived from a murine, rat, or hamster monoclonal antibody, into a vector containing sequences that encode at least one human constant region. (See, e.g., Shin et al., *Methods Enzymol.* 178:459–76, 1989; Walls et al., *Nucleic Acids Res.* 21:2921–29, 1993). The human constant region chosen may depend upon the effector functions desired for the particular antibody. Another method known in the art for generating chimeric antibodies is homologous recombination (U.S. Pat. No. 5,482,856). Preferably, the vectors will be transfected into eukaryotic cells for stable expression of the chimeric antibody.

A non-human/human chimeric antibody may be further genetically engineered to create a "humanized" antibody. Such an antibody has a plurality of CDRs derived from an immunoglobulin of a non-human mammalian species, at least one human variable framework region, and at least one human immunoglobulin constant region. Humanization may yield an antibody that has decreased binding affinity when compared with the non-human monoclonal antibody or the chimeric antibody. Those having skill in the art, therefore, use one or more strategies to design humanized antibodies.

Within certain embodiments, the use of antigen-binding fragments of antibodies may be preferred. Such fragments include Fab fragments or F(ab')$_2$ fragments, which may be prepared by proteolytic digestion with papain or pepsin, respectively. The antigen binding fragments may be separated from the Fc fragments by affinity chromatography, for example, using immobilized protein A or immobilized ligand polypeptide or a variant or a fragment thereof. An alternative method to generate Fab fragments includes mild reduction of F(ab')$_2$ fragments followed by alkylation (See, e.g., Weir, *Handbook of Experimental Immunology,* 1986, Blackwell Scientific, Boston).

Non-human, human, or humanized heavy chain and light chain variable regions of any of the above described Ig molecules may be constructed as single chain Fv (sFv) fragments (single chain antibodies). See, e.g., Bird et al., *Science* 242:423–426, 1988; Huston et al., *Proc. Natl. Acad. Sci. USA* 85:5879–5883, 1988. Multi-functional fusion proteins may be generated by linking polynucleotide sequences encoding an sFv in-frame with polynucleotide sequences encoding various effector proteins. These methods are known in the art, and are disclosed, for example, in EP-B1-0318554, U.S. Pat. No. 5,132,405, U.S. Pat. No. 5,091,513, and U.S. Pat. No. 5,476,786.

An additional method for selecting antibodies that specifically bind to a ligand polypeptide or variant or fragment thereof is by phage display (See, e.g., Winter et al., *Annul. Rev. Immunol.* 12:433–55, 1994; Burton et al., *Adv. Immunol.* 57:191–280, 1994). Human or murine immunoglobulin variable region gene combinatorial libraries may be created in phage vectors that can be screened to select Ig fragments (Fab, Fv, sFv, or multimers thereof) that bind specifically to a ligand polypeptide or variant or fragment thereof (See, e.g., U.S. Pat. No. 5,223,409; Huse et al., *Science* 246:1275–81, 1989; Kang et al., *Proc. Natl. Acad. Sci. USA* 88:4363–66, 1991; Hoogenboom et al., *J. Molec. Biol.* 227:381–388, 1992; Schlebusch et al., *Hybridoma* 16:47–52, 1997 and references cited therein).

Cell Populations

As discussed above, the present invention has broad applicability to any cell type having a cell surface moiety that one is desirous of ligating. In this regard, many cell signaling events can be enhanced by the methods of the present invention. Such methodologies can be used therapeutically in an ex vivo setting to activate and stimulate cells for infusion into a patient or could be used in vivo, to induce cell signaling events on a target cell population. However, as also noted above, the prototypic example provided herein is directed to T-cells, but is in no way limited thereto.

With respect to T-cells, the T-cell populations resulting from the various expansion methodologies described herein may have a variety of specific phenotypic properties, depending on the conditions employed. Such phenotypic properties include enhanced expression of CD25, CD154, IFN-γ and GM-CSF, as well as altered expression of CD137, CD134, CD62L, and CD49d. The ability to differentially control the expression of these moieties may be very important. For example, higher levels of surface expression of CD154 on "tailored T-cells," through contact with CD40 molecules expressed on antigen-presenting cells (such as dendritic cells, monocytes, and even leukemic B cells or lymphomas), will enhance antigen presentation and immune function. Such strategies are currently being employed by various companies to ligate CD40 via antibodies or recombinant CD40L. The approach described herein permits this same signal to be delivered in a more physiological manner, e.g., by the T-cell. The ability to increase IFN-γ secretion by tailoring the T-cell activation (XCELLERATE) process could help promote the generation of TH1-type immune responses, important for anti-tumor and anti-viral responses. Like CD154, increased expression of GM-CSF can serve to enhance APC function, particularly through its effect on promoting the maturation of APC progenitors into more functionally competent APC, such as dendritic cells. Altering the expression of CD137 and CD134 can effect a T-cell's ability to resist or be susceptible to apoptotic signals. Controlling the expression of adhesion/homing receptors, such as CD62L and/or CD49d may determine the ability of infused T-cells to home to lymphoid organs, sites of infection, or tumor sites.

An additional aspect of the present invention provides a T-cell population or composition that has been depleted of $CD8^+$ or $CD4^+$ cells prior to expansion. In one embodiment, $CD8^+$ cells are depleted by antibodies directed to the $CD8^+$ marker. One of ordinary skill in the art would readily be able to identify a variety of particular methodologies for depleting a sample of $CD8^+$ or $CD4^+$ cells or conversely enriching the $CD4^+$ or $CD8^+$ cell content. With respect to enriching for $CD4^+$ cells, one aspect of the present invention is focused on the identification of an extremely robust CD154 expression profile upon stimulation of T-cell populations wherein $T_C$ ($CD8^+$) cells have been depleted. As indicated above, CD154 is an important immunomodulating molecule whose expression is extremely beneficial in amplifying the immune response. Accordingly an increase in CD154 expression is likely to lead to more efficacious T-cell compositions.

An additional aspect of the present invention provides a T-cell population or composition that has been depleted or enriched for populations of cells expressing a variety of markers, such as CD62L, CD45RA or CD45RO, cytokines (e.g. IL-2, IFN-γ, IL-4, IL-10), cytokine receptors (e.g. CD25), perforin, adhesion molecules (e.g. VLA-1, VLA-2, VLA-4, LPAM-1, LFA-1), and/or homing molecules (e.g. L-Selectin), prior to expansion. In one embodiment, cells expressing any of these markers are depleted or positively selected by antibodies or other ligands/binding agents directed to the marker. One of ordinary skill in the art would readily be able to identify a variety of particular methodologies for depleting or positively selecting for a sample of cells expressing a desired marker.

The phenotypic properties of T-cell populations of the present invention can be monitored by a variety of methods including standard flow cytometry methods and ELISA methods known by those skilled in the art.

Those of ordinary skill in the art will readily appreciate that the cell stimulation methodologies described herein may be carried out in a variety of environments (i.e., containers). For example, such containers may be culture flasks, culture bags, or any container capable of holding cells, preferably in a sterile environment. In one embodiment of the present invention a bioreactor is also useful. For example, several manufacturers currently make devices that can be used to grow cells and be used in combination with the methods of the present invention. See for example, Celdyne Corp., Houston, Tex.; Unisyn Technologies, Hopkinton, Mass.; Synthecon, Inc. Houston, Tex.; Aastrom Biosciences, Inc. Ann Arbor, Mich.; Wave Biotech LLC, Bedminster, N.J. Further, patents covering such bioreactors include U.S. Pat. Nos. 6,096,532; 5,985,653; 5,888,807; 5,190,878, which are incorporated herein by reference.

In one embodiment, the magnet used for simultaneous stimulation and concentration of the cells of the present invention may be incorporated into the base rocker platform of a bioreactor device, such as "The Wave" (Wave Biotech LLC, Bedminster, N.J.). The magnet, or a magnetizable element, may also be enclosed into a standard bioreactor vessel such as a cylindrical application unit. This built-in magnetic element may be capable of being switched on and off as desired at various points in the cell culture procedure. The integrated magnet, or magnetizable element, is positioned so as to allow a magnetic field emanating therefrom to pass through the culture vessel. In certain embodiments, the magnet, or magnetizable element, is incorporated within a wall, or alternatively, within the body of the culture vessel. In a further embodiment, the cells can be magnetically concentrated and/or activated, magnetically separated or isolated at a desired point during culture without the need to transfer cells to a different culture or magnetic separation unit. Use of such a built-in magnetic element can facilitate culture, stimulation and concentration, and separation processes to enable expansion and tailoring of specific functional cell populations for immunotherapeutic infusion into patients in cell or gene-based therapies. Further, this device provides an improved means for specific production of molecules both inside cells and their secretion to the outside of cells.

The integrated magnetic or magnetizable device as described above can be used to either remove magnetic particles from the culture, retaining them in the culture vessel, whilst the desired cells and/or desired molecules present in the culture media are removed. Alternatively, the cells and/or desired molecules may be specifically retained in the culture bag, or other suitable culture vessel, by interaction with magnetic particles that have been coated with specific molecules as described herein that bind to the desired cells and/or molecules. The built-in magnetic or magnetizable device enables the washing of cell populations and replacement of media in the cell culture bag by magnetically immobilizing/concentrating cells with specific particles and flowing media and or other solutions through the bag. This device effectively eliminates the need for a separate magnetic separation device by providing a fully integrated system, thereby reducing process time and manual operations for tubing connectors, reducing the number of containers used in processing and reducing the likelihood of contamination through the number of tube and container connections required. This integrated magnetic or magnetizable device-culture system also reduces the volumes needed in the culture processing and formulation.

Methods of Use

In addition to the methods described above, cells stimulated and/or activated by the methods herein described may be utilized in a variety of contexts. With respect to the prototypic example of T-cells, the methodologies described herein can be used to selectively expand a population of $CD28^+$, $CD4^+$, $CD8^+$, $CD45RA^+$, or $CD45RO^+$ T-cells for use in the treatment of infectious diseases, cancer, and immunotherapy. As a result, a phenotypically unique population of T-cells, which is polyclonal with respect to antigen reactivity, but essentially homogeneous with respect to either $CD4^+$ or $CD8^+$ can be produced. In addition, the method allows for the expansion of a population of T-cells in numbers sufficient to reconstitute an individual's total $CD4^+$ or $CD8^+$ T-cell population (the population of lymphocytes in an individual is approximately $3-5\times10^{11}$). The resulting T-cell population can also be genetically transduced and used for immunotherapy or can be used in methods of in vitro analyses of infectious agents. For example, a population of tumor-infiltrating lymphocytes can be obtained from an individual afflicted with cancer and the T-cells stimulated to proliferate to sufficient numbers. The resulting T-cell population can be genetically transduced to express tumor necrosis factor (TNF) or other proteins (for example, any number of cytokines, inhibitors of apoptosis (e.g. Bcl-2), genes that protect cells from HIV infection such as RevM10 or intrakines, and the like, targeting molecules, adhesion and/or homing molecules and any variety of antibodies or fragments thereof (e.g. Scfv)) and given to the individual.

One particular use for the $CD4^+$ T-cells populations of the invention is the treatment of HIV infection in an individual. Prolonged infection with HIV eventually results in a marked decline in the number of $CD4^+$ T lymphocytes. This decline, in turn, causes a profound state of immunodeficiency, rendering the patient susceptible to an array of life threatening opportunistic infections. Replenishing the number of $CD4^+$ T-cells to normal levels may be expected to restore immune function to a significant degree. Thus, the method described herein provides a means for selectively expanding $CD4^+$ T-cells to sufficient numbers to reconstitute this population in an HIV infected patient. It may also be necessary to avoid infecting the T-cells during long-term stimulation or it may be desirable to render the T-cells permanently resistant to HIV infection. There are a number of techniques by which T-cells may be rendered either resistant to HIV infection or incapable of producing virus prior to restoring the T-cells to the infected individual. For example, one or more anti-retroviral agents can be cultured with $CD4^+$ T-cells prior to expansion to inhibit HIV replication or viral production (e.g., drugs that target reverse transcriptase and/or other components of the viral machinery, see e.g., Chow et al. *Nature* 361:650–653, 1993).

Several methods can be used to genetically transduce T-cells to produce molecules which inhibit HIV infection or replication. For example, in various embodiments, T-cells can be genetically transduced to produce transdominant inhibitors, "molecular decoys", antisense molecules, intrakines, or toxins. Such methodologies are described in further detail in U.S. patent application Ser. Nos. 08/253,751, 08/253,964, and PCT Publication No. WO 95/33823, which are incorporated herein by reference in their entirety.

The methods for stimulating and expanding a population of antigen specific T-cells are useful in therapeutic situations where it is desirable to up-regulate an immune response (e.g., induce a response or enhance an existing response) upon administration of the T-cells to a subject. For example, the method can be used to enhance a T-cell response against tumor-associated antigens. Tumor cells from a subject typically express tumor-associated antigens but may be unable to stimulate a co-stimulatory signal in T-cells (e.g., because they lacks expression of co-stimulatory molecules). Thus, tumor cells can be contacted with T-cells from the subject in vitro and antigen specific T-cells expanded according to the method of the invention and the T-cells returned to the subject.

Accordingly, in one embodiment malignancies such as non-Hodgkins Lymphoma (NHL) and B-cell chronic lymphocytic leukemia (B-CLL) can be treated. While initial studies using expanded T-cells have been tested in NHL, (see Liebowitz et al., *Curr. Opin. Onc.* 10:533–541, 1998), the T-cell populations of the present invention offer unique phenotypic characteristics that can dramatically enhance the success of immunotherapy by providing increased engraftment (likely supplied by stimulation of the CD28 signal) and reactivity. However, patients with B-CLL present special difficulties, including low relative T-cell numbers with high leukemic cell burden in the peripheral blood, accompanied by a general T-cell immunosuppression. The T-cell populations of the present invention can provide dramatically improved efficacy in treating this disease and especially when combined with stem cell transplantation therapy. Accordingly, increasing T-cell function and anti-CLL T-cell activity with anti-CD3×anti-CD28 co-immobilized beads would be beneficial.

For example, given that deficient expression of CD154, the ligand for CD40, on T-cells of B-CLL patients has been cited as a major immunological defect of the disease, the T-cell populations of the present invention, which may provide sustained high levels of CD154 expression upon re-infusion, could aid in its treatment. Investigators report that in CLL the capability of a patient's T-cells' to express CD154 is defective as well as the capability of the leukemic B-cells to express CD80 and CD86. The failure of leukemic B-cells in CLL to adequately express the ligands for CD28, could result in failure to fully activate tumor-responsive T-cells and, therefore, may represent the mechanism underlying the T-cells' apparent state of tolerance. Studies in which CD40 is engaged on CLL B cells, either via soluble anti-CD40 antibodies or via CD154-transduced leukemic B-cells, appears to correct the defect in CD80 and CD86 expression and up-regulates MHC surface expression. Kato et al., *J. Clin. Invest.* 101:1133–1141, 1998; Ranheim and Kipps, *J. Exp. Med.* 177:925–935, 1993. Cells treated in this way were able to stimulate specific T-cell anti-tumor responses.

With the enhanced expression of CD154 on the surface of the T-cell population of the present invention such T-cells would be expected to interact with autologous B-CLL cells, and would thus increase that tumor's immunogenicity by driving up expression of MHC, CD80, and CD86. This, in turn, should lead to a strong anti-tumor response. Further, one of ordinary skill in the art would readily understand that treatment of a patient with ex vivo expanded T-cells of the present invention may be combined with traditional cancer therapies such as chemotherapy. In this regard, for example, a patient may be treated with an agent such as Fludarabine or Campath (Berlex Laboratories, Montville, N.J., USA), followed by infusion with T-cell populations of the present invention or both.

Alternatively, T-cells can be stimulated and expanded as described herein to induce or enhance responsiveness to pathogenic agents, such as viruses (e.g., human immunodeficiency virus), bacteria, parasites and fungi.

The invention further provides methods to selectively expand a specific subpopulation of T-cells from a mixed population of T-cells. In particular, the invention provides specifically enriched populations of T-cells that have much higher ratio of $CD4^+$ and $CD8^+$ double positive T-cells.

Another embodiment of the invention, provides a method for selectively expanding a population of $T_{H1}$ cells from a population of $CD4^+$ T-cells. In this method, $CD4^+$ T-cells are co-stimulated with an anti-CD28 antibody, such as the monoclonal antibody 9.3, inducing secretion of $T_{H1}$-specific cytokines, including IFN-γ, resulting in enrichment of $T_{H1}$ cells over $T_{H2}$ cells.

The observation herein that phenotypic traits of activated T-cells vary over time during the expansion process, combined with the fact that T-cells have been demonstrated to be activated within a few hours (Iezzi et al., Immunity 8:89–95, 1998). Accordingly, in combination with the methodologies herein described, this provides the ability to expand a tailor made subset of a T-cell population in a short period of time. In one embodiment, this technique can be utilized at the bedside of a subject, in an outpatient modality, or at a subject's home, similar to the use of kidney dialysis. For example, a method or device wherein T-cells are incubated in contact with activation signals (e.g., anti-CD3 and anti-CD28 antibodies, and the like) and returned to the patient immediately in a continuous flow or after a few hour expansion period. In one aspect, such techniques of expansion could use isolated chambers with filter components, such that 3×28 beads or similarly coated microparticles are mixed with a continuous flow of blood/ concentrated cells. In another embodiment, solid surfaces within an apparatus may be coated or conjugated directly (including covalently) or indirectly (e.g., streptavidin/biotin and the like) with antibodies or other components to stimulate T-cell activation and expansion. For example, a continuous fluid path from the patient through a blood/cell collection device and/or a disposable device containing two or more immobilized antibodies (e.g., anti-CD3 and anti-CD28) or other components to stimulate receptors required for T-cell activation prior to cells returning to the subject can be utilized (immobilized on plastic surfaces or upon separable microparticles). Such a system could involve a leukapheresis instrument with a disposable set sterile docked to the existing manufacturers disposable set, or be an adaptation to the manufacturer's disposable set (e.g., the surface platform on which the antibodies/activation components are immobilized/contained is within the bag/container for collection of peripheral blood mononuclear cells during apheresis). Further, the solid surface/surface platform may be a part of a removal insert which is inserted into one of the device chambers or physically present within one of the disposable components. In another embodiment of the continuous flow aspect discussed above, the system may comprise contacting the cells with the activating components at room temperature or at physiologic temperature using a chamber within a blood collection device or an incubation chamber set up in series with the flow path to the patient.

In another example, blood is drawn into a stand-alone disposable device directly from the patient that contains two or more immobilized antibodies (e.g., anti-CD3 and anti-CD28) or other components to stimulate receptors required for T-cell activation prior to the cells being administered to the subject (e.g., immobilized on plastic surfaces or upon separable microparticles). In one embodiment, the disposable device may comprise a container (e.g., a plastic bag, or flask) with appropriate tubing connections suitable for combining/docking with syringes and sterile docking devices. This device will contain a solid surface for immobilization of T-cell activation components (e.g., anti-CD3 and anti-CD28 antibodies); these may be the surfaces of the container itself or an insert and will typically be a flat surface, an etched flat surface, an irregular surface, a porous pad, fiber, clinically acceptable/safe ferro-fluid, beads, etc.). Additionally when using the stand-alone device, the subject can remain connected to the device, or the device can be separable from the patient. Further, the device may be utilized at room temperature or incubated at physiologic temperature using a portable incubator.

As devices and methods for collecting and processing blood and blood products are well known, one of skill in the art would readily recognize that given the teachings provided herein, that a variety of devices that fulfil the needs set forth above may be readily designed or existing devices modified. Accordingly, as such devices and methods are not limited by the specific embodiments set forth herein, but would include any device or methodology capable of maintaining sterility and which maintains blood in a fluid form in which complement activation is reduced and wherein components necessary for T-cell activation (e.g., anti-CD3 and anti-CD28 antibodies or ligands thereto) may be immobilized or separated from the blood or blood product prior to administration to the subject. Further, as those of ordinary skill in the art can readily appreciate a variety of blood products can be utilized in conjunction with the devices and methods described herein. For example the methods and devices could be used to provide rapid activation of T-cells from cryopreserved whole blood, peripheral blood mononuclear cells, other cyropreserved blood-derived cells, or cryopreserved T-cell lines upon thaw and prior to subject adminstration. In another example, the methods and devices can be used to boost the activity of a previously ex vivo expanded T-cell product or T cell line prior to administration to the subject, thus providing a highly activated T-cell product. Lastly, as will be readily appreciated the methods and devices above may be utilized for autologous or allogeneic cell therapy simultaneously with the subject and donor.

The methods of the present invention may also be utilized with vaccines to enhance reactivity of the antigen and enhance in vivo effect. Further, given that T-cells expanded by the present invention have a relatively long half-life in the body, these cells could act as perfect vehicles for gene therapy, by carrying a desired nucleic acid sequence of interest and potentially homing to sites of cancer, disease, or infection. Accordingly, the cells expanded by the present invention may be delivered to a patient in combination with a vaccine, one or more cytokines, one or more therapeutic antibodies, etc. Virtually any therapy that would benefit by a more robust T-cell population is within the context of the methods of use described herein.

Pharmaceutical Compositions

Target cell populations, such as T-cell populations of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

All references referred to within the text are hereby incorporated by reference in their entirety. Moreover, all numerical ranges utilized herein explicitly include all integer values within the range and selection of specific numerical values within the range is contemplated depending on the particular use. Further, the following examples are offered by way of illustration, and not by way of limitation.

EXAMPLES

Example I

T-Cell Stimulation

In certain experiments described herein, the process referred to as XCELLERATE I™ was utilized. In brief, in this process, the XCELLERATED™ T-cells are manufactured from a peripheral blood mononuclear cell (PBMC) apheresis product. After collection from the patient at the clinical site, the PBMC apheresis are washed and then incubated with "uncoated" DYNABEADS® M-450 Epoxy T. During this time phagocytic cells such as monocytes ingest the beads. After the incubation, the cells and beads are processed over a MaxSep Magnetic Separator in order to remove the beads and any monocytic/phagocytic cells that are attached to the beads. Following this monocyte-depletion step, a volume containing a total of $5\times10^8$ CD3$^+$ T-cells is taken and set-up with $1.5\times10^9$ DYNABEADS® M-450 CD3/CD28 T to initiate the XCELLERATE™ process (approx. 3:1 beads to T-cells). The mixture of cells and DYNABEADS® M-450 CD3/CD28 T are then incubated at 37° C., 5% $CO_2$ for approximately 8 days to generate XCELLERATED T-cells for a first infusion. The remaining monocyte-depleted PBMC are cryopreserved until a second or further cell product expansion (approximately 21 days later) at which time they are thawed, washed and then a volume containing a total of $5\times10^8$ CD3$^+$ T-cells is taken and set-up with $1.5\times10^9$ DYNABEADS® M-450 CD3/CD28 T to initiate the XCELLERATE Process for a second infusion. During the incubation period of ≈8 days at 37° C., 5% $CO_2$, the CD3$^+$ T-cells activate and expand. The anti-CD3 mAb used is BC3 (XR-CD3; Fred Hutchinson Cancer Research Center, Seattle, Wash.), and the anti-CD28 mAb (B-T3, XR-CD28) is obtained from Diaclone, Besancon, France.

Figure 5A:
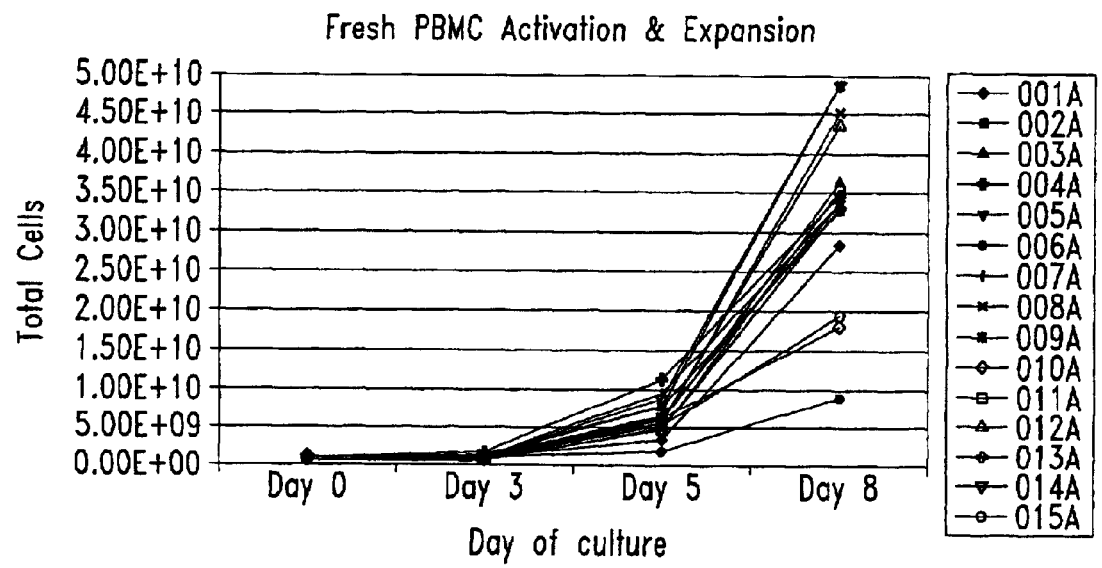
FIGS. 5A–5B are plots depicting T-cell activation and expansion with XCELLERATE I™ PBMC (5A) or PBMC having been frozen and thawed (5B) to initiate the XCELLERATE I™ process.
Figure 5B:
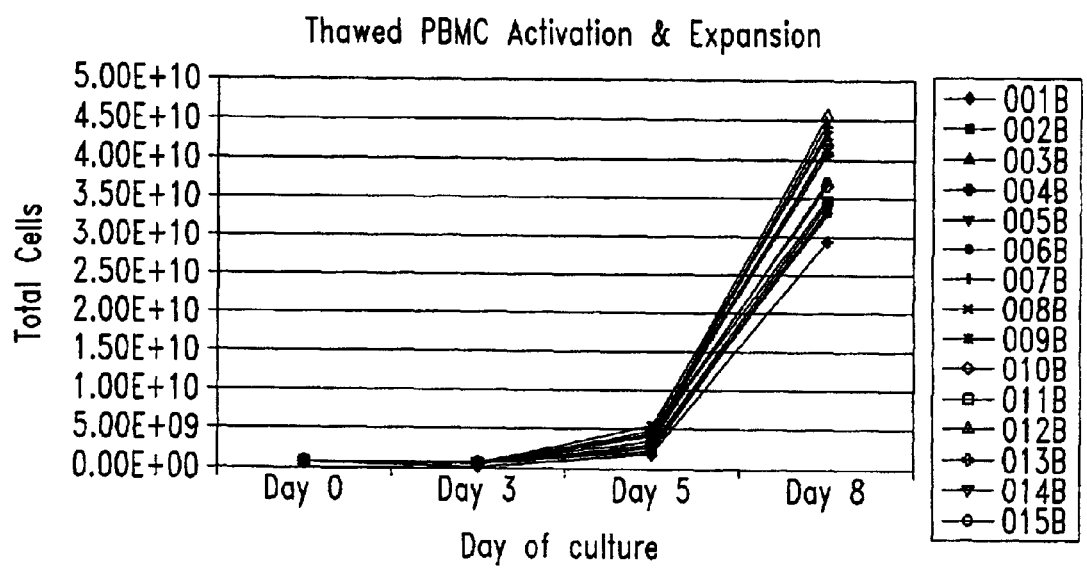

With a modified process referred to as XCELLERATE II™ the process described above was utilized with some modifications in which no separate monocyte depletion step was utilized and in certain processes the cells were frozen prior to initial contact with beads and further concentration and stimulation were performed. (See FIGS. 5A and 5B). In one version of this process T-cells were obtained from the circulating blood of a donor or patient by apheresis. Components of an apheresis product typically include lymphocytes, monocytes, granulocytes, B cells, other nucleated cells (white blood cells), red blood cells, and platelets. A typical apheresis product contains $1$–$2\times10^{10}$ nucleated cells. The cells are washed with calcium-free, magnesium-free phosphate buffered saline to remove plasma proteins and platelets. The washing step was performed by centrifuging the cells and removing the supernatant fluid, which is then replaced by PBS. The process was accomplished using a semi-automated "flow through" centrifuge (COBE 2991 System, Baxter). The cells are maintained in a closed system as they are processed.

The cells may be further processed by depleting the non-binding cells, including monocytes, (enriched for activated cells) and then continuing with the stimulation. Alternatively, the washed cells can be frozen, stored, and processed later, which is demonstrated herein to increase robustness of proliferation as well as depleting granulocytes. In one example, to freeze the cells, a 35 ml suspension of cells is placed in a 250 ml Cryocyte freezing bag along with 35 ml of the freezing solution. The 35 ml cell suspension typically contains $3.5\times10^9$ to $5.0\times10^9$ cells in PBS. An equal volume of freezing solution (20% DMSO and 8% human serum albumin in PBS) is added. The cells are at a final concentration of $50\times10^6$ cells/ml. The Cryocyte bag may contain volumes in the range of 30–70 ml, and the cell concentration can range from 10 to $200\times10^6$ cells/ml. Once the Cryocyte bag is filled with cells and freezing solution, the bag is placed in a controlled rate freezer and the cells are frozen at 1° C./minute down to −80° C. The frozen cells are then placed in a liquid nitrogen storage system until needed.

The cells are removed from the liquid nitrogen storage system and are thawed at 37° C. To remove DMSO, the thawed cells are then washed with calcium-free, magnesium-free PBS on the COBE 2991 System. The washed cells are then passed through an 80 micron mesh filter.

The thawed cells, approximately $0.5\times10^9$ CD3$^+$ cells, are placed in a plastic 1L Lifecell bag that contains 100 ml of calcium-free, magnesium-free PBS. The PBS contains 1%–5% human serum. $1.5\times10^9$ 3×28 beads (DYNABEADS® M-450 CD3/CD28 T) are also placed in the bag with the cells (3:1 DYNABEADS M-450 CD3/CD28 T:CD3$^+$ T-cells). The beads and cells are mixed at room temperature at ~1 RPM (end-over-end rotation) for about 30 minutes. The bag containing the beads and cells is placed on the MaxSep Magnetic Separator (Nexell Therapeutics, Irvine, CAb. Between the bag and the MaxSep, a plastic spacer (approximately 6 mm thick) is placed. (To increase the magnetic strength the spacer is removed.) The beads and any cells attached to beads are retained on the magnet while the PBS and unbound cells are pumped away.

The 3×28 beads and concentrated cells bound to the beads are rinsed with cell culture media (1 liter containing X-Vivo 15, BioWhittaker; with 50 ml heat inactivated pooled human serum, 20 ml 1M Hepes, 10 ml 200 mM L-glutamine with or without about 100,000 I.U. IL-2) into a 3L Lifecell culture bag. After transferring the 3×28 beads and positively selected cells into the Lifecell bag, culture media is added until the bag contains 1000 ml. The bag containing the cells is placed in an incubator (37° C. and 5% $CO_2$) and cells are allowed to expand.

Cells were split 1 to 4 on each of days 3 and 5. T-cell activation and proliferation were measured by harvesting cells after 3 days and 8 days in culture. Activation of T-cells was assessed by measuring cell size, the level of cell surface marker expression, particularly the expression of CD25 and CD154 on day 3 of culture. On day 8 cells were allowed to flow under gravity (approx. 150 ml/min) over the MaxSep magnet to remove the magnetic particles and the cells are washed and concentrated using the COBE device noted above and resuspended in a balanced electrolyte solution suitable for intravenous administration, such as Plasma-Lyte A® (Baxter-Healthcare).

As described within the specification XCELLERATE I™ refers to conditions similar to that above, except that stimulation and concentration were not performed and monocyte depletion was performed prior to stimulation.

Both XCELLERATE I™ and II™ processes were performed and T-cell proliferation was measured after 8 days in culture. The yield of expanded T-cells was greater when $CD3^+$ cells were concentrated prior to cell culture. (See Table 1). In addition, the cell population had greater than 90% $CD3^+$ cells.

TABLE 1

T-Cell Yield Expansion at Day 8

| Experiment | No $CD3^+$ Concentration (XCELLERATE I ™) | $CD3^+$ Concentration (XCELLERATE II ™) |
|---|---|---|
| NDa079 | $33 \times 10^9$ | $36 \times 10^9$ |
| NDa081 | $38 \times 10^9$ | $42 \times 10^9$ |
| NDa082 | $28 \times 10^9$ | $38 \times 10^9$ |
| Average | $33 \pm 5 \times 10^9$ | $39 \pm 3 \times 10^9$ |

Figure 2:
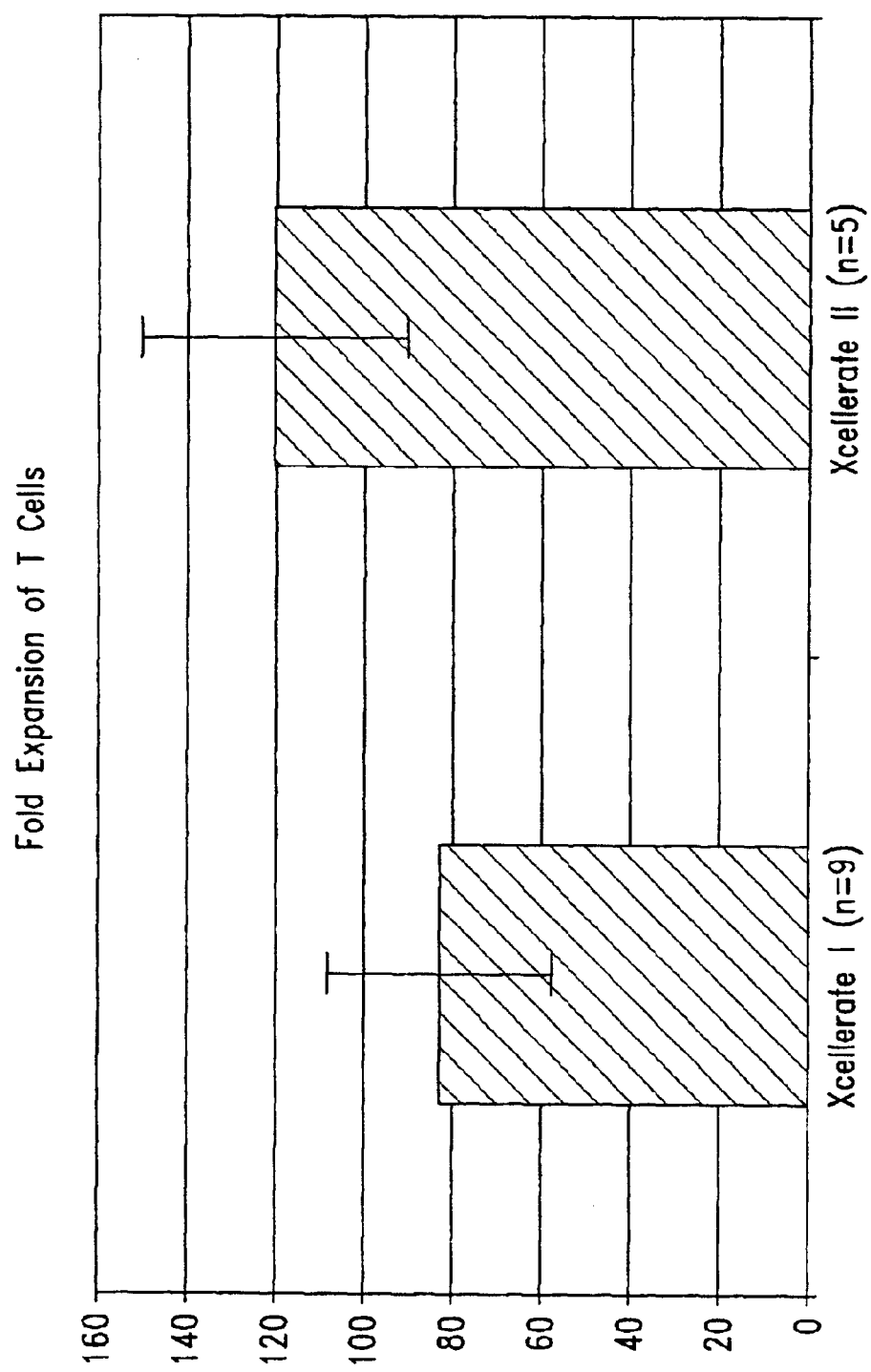
FIG. 2 is a plot comparing fold expansion of activated and expanded T-cells measured at day 8 with (XCELLERATE II™) or without (XCELLERATE I™) magnetic concentration and stimulation.

Further experiments were performed in this regard and depict total number of expanded cells as well as the fold expansion of nine batches of cells stimulated without $CD3^+$ concentration and five batches of cells stimulated with $CD3^+$ concentration. (See FIGS. 1 and 2).

Figure 3:
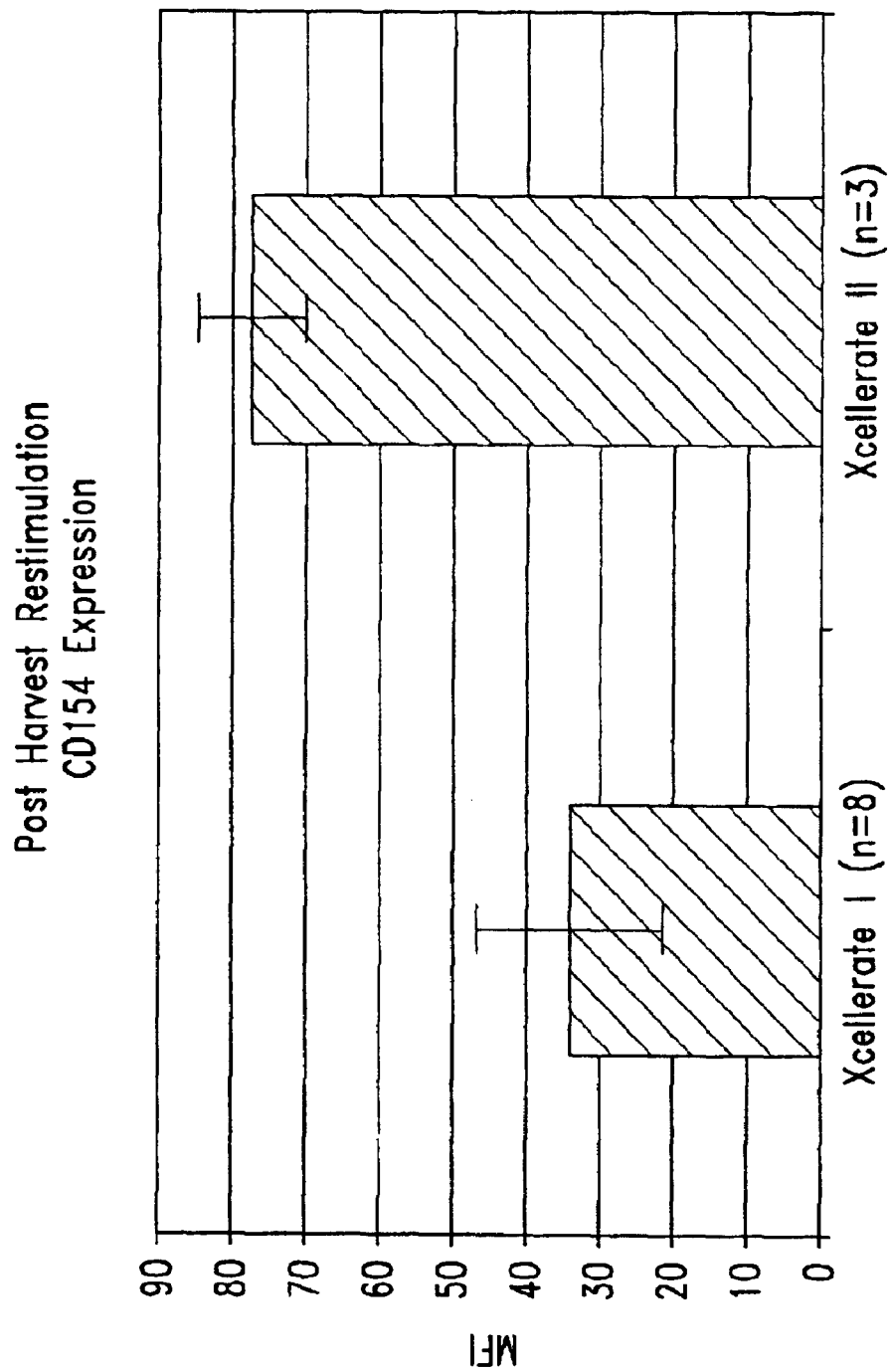
FIG. 3 is a plot representing flow cytometry analysis of CD154 expression comparing restimulation of T-cells previously cultured for 8 days after magnetic concentration and stimulation (XCELLERATE II™) or without magnetic concentration and stimulation (XCELLERATE I™).
Figure 4:
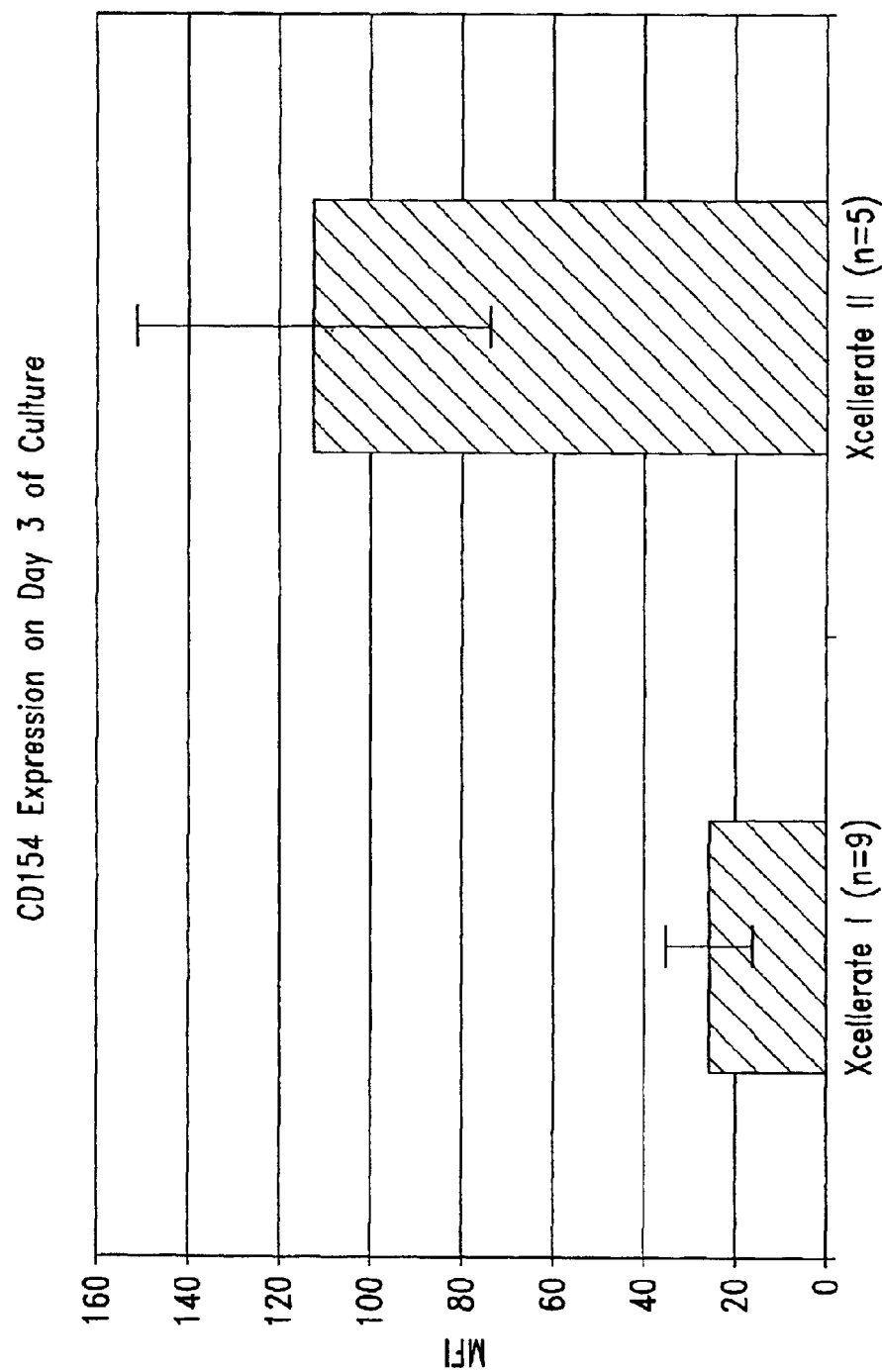
FIG. 4 is a plot representing flow cytometry analysis of CD154 expression following 3 days in culture comparing magnetic concentration and stimulation (XCELLERATE II™) with cells activated without magnetic concentration and stimulation (XCELLERATE I™).

Concentration of the cells by application of a magnetic force prior to culture effectively increases the purity of the $CD3^+$ cells as well as increasing CD154 levels. (Table 2, FIGS. 3 and 4 depict CD154 levels graphically). Furthermore, comparison of T-cell proliferation where populations of T-cells were exposed to magnets of differing strengths showed that exposure to a stronger magnet resulted in greater yield of $CD3^+$ cells. (Table 2.)

TABLE 2

Comparison of T-Cell Proliferation and Cell Surface Markers after Concentration Using Weak and Strong Magnets

| Experiment | Magnet | Day | CD3% | Size (FSC) | CD25 (MFI) | CD154 (MFI) | CD3# × $10^9$ |
|---|---|---|---|---|---|---|---|
| NDa087 | | | | | | | |
| Pre-Selection | | 0 | 47% | 318 | 8 | 4 | 0.5 |
| Post-Selection | Weak | 0 | 56% | | | | 0.37 |
| Post-Selection | Strong | 0 | 61% | | | | 0.35 |
| No Selection | None | 3 | | 533 | 758 | 19 | |
| Post-Selection | Weak | 3 | 90% | 570 | 846 | 41 | |
| Post-Selection | Strong | 3 | 92% | 558 | 1006 | 45 | |
| Post-Culture | None | | | | | | |
| Post-Culture | Weak | 8 | 92% | 412 | 110 | 9 | 17.7 |
| | Strong | 8 | 93% | 413 | 89 | 7 | 37.8 |
| NDa089 | | | | | | | |
| Pre-Selection | | 0 | 44% | 312 | 6 | 4 | 0.5 |
| Post-Selection | Weak | 0 | 46% | | | | 0.39 |
| Post-Selection | Strong | 0 | 55% | | | | 0.3 |
| Post-Selection | Weak | 3 | 83% | 589 | 685 | 67 | |
| Post-Selection | Strong | 3 | 83% | 600 | 720 | 115 | |
| Post-Culture | Weak | 8 | 89% | 409 | 58 | 18 | 25.3 |
| | Strong | 8 | 87% | 371 | 65 | 13 | 42.1 |

| Experiment | Magnet | CD25 on Day 0 (MFI) | CD25 on Day 3 (MFI) | CD154 on Day 0 (MFI) | CD154 on Day 3 (MFI) | CD3 Cell # on Day 8 × $10^9$ |
|---|---|---|---|---|---|---|
| NDa087 | | | | | | |
| No Selection | None | 8 | 758 | 4 | 19 | 31 |
| Selection | Weak | 8 | 846 | 4 | 41 | 18 |
| Selection | Strong | 8 | 1006 | 4 | 45 | 38 |
| NDa089 | | | | | | |
| No Selection | None | 6 | 309 | 4 | 12 | 26 |
| Selection | Weak | 6 | 685 | 4 | 67 | 25 |
| Selection | Strong | 6 | 720 | 4 | 115 | 42 |

Five additional experiments were performed comparing the process of XCELLERATE I™ to that of XCELLERATE II™. For the cells activated and culture-expanded according to the two processes, cell activation markers (cell size, CD25 expression, and CD154 expression) on days 3 and 8 of culture are shown below in Table 3 and in FIGS. 6–7.

TABLE 3

Cell Activation Markers on Day 3

| Experiment Number (Donor) | Process | Cell Size (FSC) Day 0 | Cell Size (FSC) Day 3 | CD25 (MFI) Day 0 | CD25 (MFI) Day 3 | CD154 (MFI) Day 0 | CD154 (MFI) Day 3 |
|---|---|---|---|---|---|---|---|
| NDa104 (PC071) | XCELLERATE I | 282 | 526 | 7 | 625 | 5 | 50 |
|  | XCELLERATE II | 315 | 531 | 7 | 750 | 5 | 162 |
| NDa107 (PC074) | XCELLERATE I | 243 | 578 | 5 | 287 | 4 | 23 |
|  | XCELLERATE II | 272 | 587 | 6 | 311 | 5 | 120 |
| NDa110 (PC076) | XCELLERATE I | 262 | 588 | 6 | 497 | 4 | 59 |
|  | XCELLERATE II | 284 | 615 | 6 | 580 | 5 | 197 |
| NDa113 (PC060) | XCELLERATE I | 271 | 662 | 5 | 726 | 4 | 54 |
|  | XCELLERATE II | 291 | 660 | 6 | 741 | 5 | 177 |
| NDa115 (PC073) | XCELLERATE I | 253 | 560 | 6 | 202 | 6 | 25 |
|  | XCELLERATE II | 252 | 582 | 6 | 448 | 6 | 83 |
| Average ± Std Dev | XCELLERATE I | 262 ± 15 | 583 ± 50 | 6 ± 1 | 467 ± 221 | 5 ± 1 | 42 ± 17 |
|  | XCELLERATE II | 283 ± 23 | 595 ± 47 | 6 ± 1 | 566 ± 189 | 5 ± 1 | 148 ± 17 |

All cultures in Table 3 were initiated with cells that were frozen/thawed.

Figure 6A:
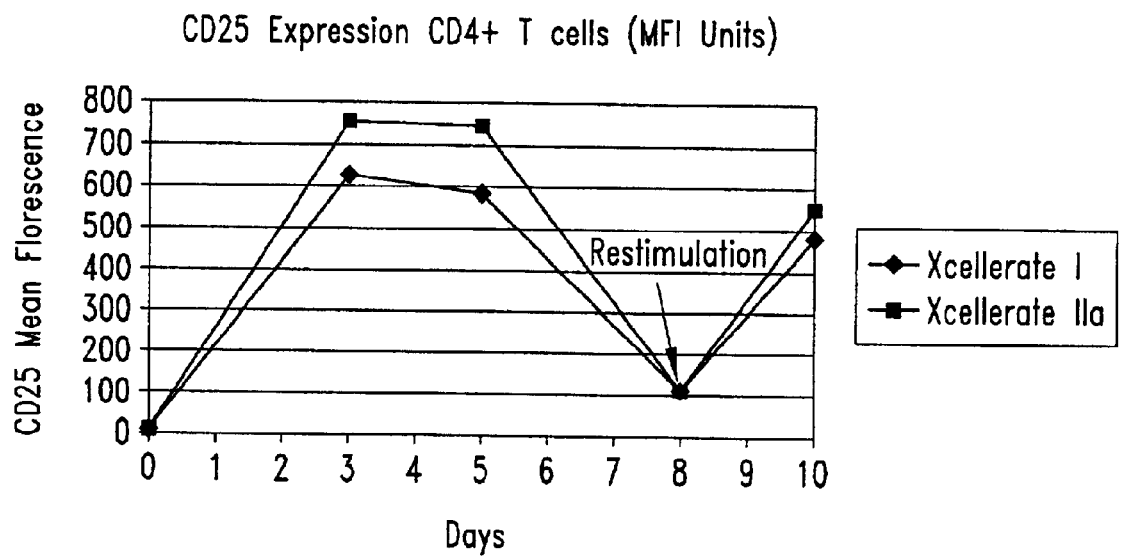
FIGS. 6A–6B are plots depicting time course analysis of CD25 expression following activation of T-cells in one donor sample (PC071) during the XCELLERATE I or II™ process. Restimulation was performed at the 8 day mark to simulate in vivo activation.
Figure 6B:
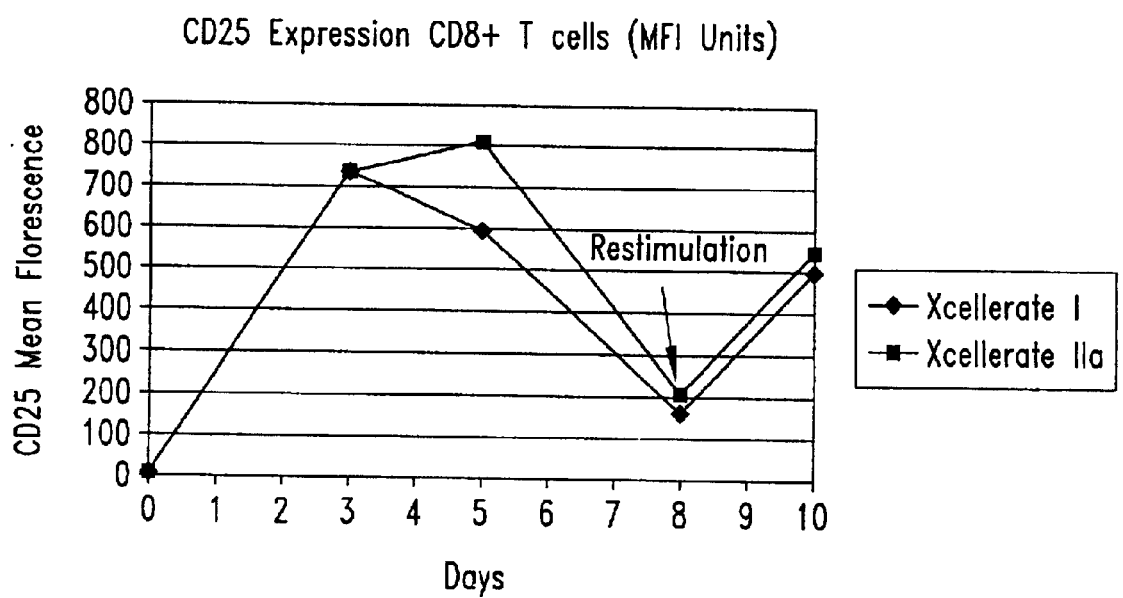
Figure 7A:
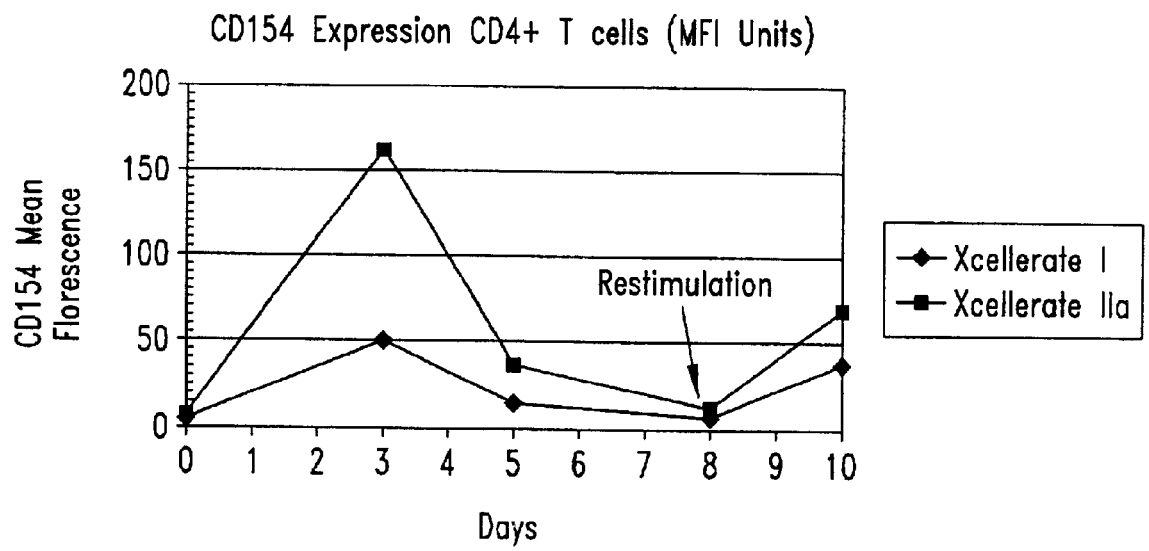
FIGS. 7A–7B are plots depicting time course analysis of CD154 expression following activation of T-cells in one donor sample (PC071) during the XCELLERATE I or II™ process. Restimulation was performed at the 8 day mark to simulate in vivo activation.
Figure 7B:
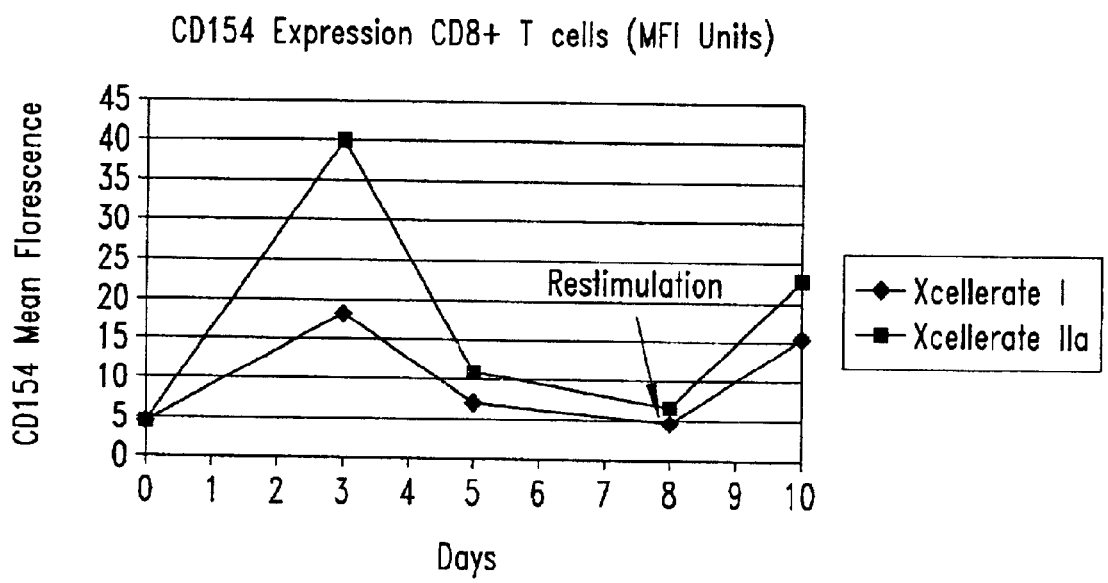

The data in Table 3 and FIGS. 6–7 show that the XCELLERATE II™ process generated cells whose cell size and CD25 expression activation markers on day 3 were on average similar, but typically higher and continued to be higher following stimulation. However, the CD154 activation marker on day 3 for T-cells from the XCELLERATE II™ process was much greater than for those of T-cells from the XCELLERATE I™ process. Further, as demonstrated above, the XCELLERATE II™ process generated CD25 and CD154 levels that were consistently higher per donor than other methods.

The expression of CD154 on Day 3 of the XCELLERATE II™ process is actually much higher than for XCELLERATE I™. This observation suggests that the T-cells are in a higher state of activation during the XCELLERATE II™ process than in the XCELLERATE I™ process. It is predicted that this may translate into a more effective product when administered in vivo.

$CD3^+$ Cell Purity, CD4 Cell/CD8 cell ratio, and cell viability on Day 3 of culture were also determined for five patient samples. The phenotype and viability of cells used subjected to the XCELLERATE I™ process and the XCELLERATE II™ process are shown below in Table 4 as measured by Flow Cytometry or Trypan blue staining.

TABLE 4

| NDa # | Day 0 $CD3^+$ Cell Purity (%)* | Day 0 Cell Viability (%) | Day 0 CD4:CD8 ratio$^\psi$ | Day 3 $CD3^+$ Cell Purity (%) | Day 3 Cell Viability (%) | Day 3 CD4:CD8 ratio |
|---|---|---|---|---|---|---|
| 103 XCELLERATE I | 70 | 92 | 1.91 | 79 | 82 | 1.3 |
| 103 XCELLERATE II | 85 | 99 | 2.3 | 91 | 95 | 2.4 |
| 104 XCELLERATE I | 67 | 95 | 3.2 | 84 | 78 | 2.7 |
| 104 XCELLERATE II | 110 | 99 | 3.7 | 93 | 87 | 2.9 |
| 107 XCELLERATE I | 69 | 99 | 2.3 | 85 | 82 | 2.3 |
| 107 XCELLERATE II | 119 | 99 | 2.7 | 95 | 92 | 2.8 |

TABLE 4-continued

| NDa # | Day 0 CD3+ Cell Purity (%)* | Day 0 Cell Viability (%) | Day 0 CD4:CD8 ratio$^\Psi$ | Day 3 CD3+ Cell Purity (%) | Day 3 Cell Viability (%) | Day 3 CD4:CD8 ratio |
|---|---|---|---|---|---|---|
| 110 XCELLERATE I | 63 | 99 | 2.9 | 91 | 82 | 2.6 |
| 110 XCELLERATE II | 83 | 99 | 3.9 | 93 | 92 | 4.5 |
| 115 XCELLERATE I | 60 | 99 | 1.9 | 92 | 91 | 2.7 |
| 115 XCELLERATE II | 72 | 99 | 2.2 | 96 | 94 | 2.8 |

\* = Purity of CD3+ T-cells on day 0 after monocyte-depletion in the XCELLERATE I process or after magnetic concentration in the XCELLERATE II process
$\Psi$ = ratio of CD4+:CD8+ T-cells on day 0 after monocyte-depletion in the XCELLERATE I process or after magnetic concentration in the XCELLERATE II process Example II Efficiency of CD3+ T-Cell Enrichment, Monocyte-Depletion and Granulocyte-Depletion For this study, upon receipt at the Xcyte Therapies Development laboratory, the incoming PBMC apheresis product was washed, split and:

1. For the XCELLERATE I process, a monocyte-depletion step was carried out and the CD14+ monocyte-depleted PBMC were cryopreserved and stored in the vapor phase of a LN$_2$ freezer (as noted in Example I). On the day of set-up of the XCELLERATE I process, the CD14+ monocyte-depleted PBMC were thawed and the XCELLERATE process initiated with DYNABEADS M-450 CD3/CD28 T as detailed in Example I. The average cellular composition and the average efficiency of CD3+ T-cell enrichment, CD14+ monocyte-depletion and granulocyte-depletion for the N=5 donors in these initial steps is shown in Table 5.1 and the data for each individual donor is shown in Table 5.2.

2. For the XCELLERATE II process, the PBMC apheresis product cells cryopreserved and stored in the vapor phase of a LN$_2$ freezer. On the day of set-up of the XCELLERATE II process, the cryopreserved PBMC apheresis product cells were thawed and the CD3+ T-cells magnetically concentrated and the XCELLERATE II process initiated with DYNABEADS M-450 CD3/CD28 T as detailed in Example I. The average cellular composition and the average efficiency of CD3+ T-cell enrichment, CD14+ monocyte-depletion and granulocyte-depletion for the N=5 donors in these initial steps is shown in Table 5.1 and the data for each individual donor is shown in Table 5.2.

As demonstrated in Tables 5.1 and 5.2, the combination of freeze/thawing of the PBMC apheresis product followed by magnetic concentration of CD3+ T-cells direct from the thawed PBMC apheresis product in the XCELLERATE II process configuration results in efficient elimination of CD14+ monocytes and granulocytes (Table 5.1 and Table 5.2). The efficiency of the elimination of the CD14+ monocytes and the granulocytes in the XCELLERATE II process is as good as that of the XCELLERATE I process with the benefit that it eliminates the need for a separate depletion step using the additional "uncoated" DYNABEADS M-450 T reagent and consistently leads to a higher CD4/CD8 ratio.

TABLE 5.1

Average (N = 5) efficiency of CD3+ T-cell enrichment, CD14+ monocyte-depletion and granulocyte-depletion in the Initial Steps of the XCELLERATE I and the XCELLERATE II Process Configurations

| Cell Preparation | Average ± Std. Dev Cellular Composition (%) | | | |
|---|---|---|---|---|
| | CD3+ | CD14+ | Granulocytes | CD4/CD8* |
| Incoming PBMC apheresis product XCELLERATE I | 49 ± 6 | 16 ± 3 | 8 ± 7 | 2.2 ± 0.3 |
| Monocyte-depleted PBMC | 51 ± 6 | 5.5 ± 3 | 5.7 ± 5 | 2.4 ± 0.6 |
| Freeze/thawed Monocyte-depleted PBMC XCELLERATE II | 64 ± 4 | 6 ± 3 | 0.4 ± 0.5 | 2.4 ± 0.6 |
| Freeze-thawed PBMC apheresis product | 56 ± 5 | 11 ± 2 | 0.4 ± 0.5 | 2.4 ± 0.8 |
| Post-CD3+ magnetic concentration | 92 ± 22 | 2.4 ± 3.7 | 0 ± 0 | 2.86 ± 0.86 |

Cellular compositions were determined by flow cytometry according to standard protocols

TABLE 5.2

Comparison of the efficiency of CD3+ T-cell enrichment, CD14+
monocyte-depletion and granulocyte-depletion in the initial steps
of the XCELLERATE I and the XCELLERATE II process configurations

| Experiment Number (Donor) | Cell Preparation | Cellular Composition (%) | | | |
|---|---|---|---|---|---|
| | | CD3+ | CD14+ | Granulocytes | CD4/CD8* |
| NDa104 (PC071) | Incoming PBMC apheresis product<br>XCELLERATE I | 43% | 11% | 14% | 2.2 |
| | Monocyte-depleted PBMC | 54% | 5% | 12.5% | 3.2 |
| | Freeze/thawed Monocyte-depleted PBMC<br>XCELLERATE II | 67% | 4% | 0% | 3.2 |
| | Freeze-thawed PBMC apheresis product | 64% | 7% | 0% | 3.1 |
| | Post-CD3− magnetic concentration | 110% | 1% | 0% | 3.7 |
| NDa107 (PC074) | Incoming PBMC apheresis product<br>XCELLERATE I | 51% | 16% | 1% | 2.1 |
| | Monocyte-depleted PBMC | 64% | 5% | 1% | 2.3 |
| | Freeze/thawed Monocyte-depleted PBMC<br>XCELLERATE II | 69% | 3% | 0% | 2.3 |
| | Freeze-thawed PBMC apheresis product | 55% | 11% | 0% | 2.0 |
| | Post- CD3− magnetic concentration | 120% | 0% | 0% | 2.7 |
| NDa110 (PC076) | Incoming<br>XCELLERATE I | 44% | 18% | 15% | 2.5 |
| | Monocyte-depleted PBMC | 63% | 3.5% | 10% | 2.9 |
| | Freeze/thawed Monocyte-depleted PBMC<br>XCELLERATE II | 63% | 7% | 0% | 2.9 |
| | Freeze-thawed PBMC apheresis product | 55% | 13% | 0% | 3.2 |
| | Post- CD3− magnetic concentration | 83% | 1% | 0% | 3.8 |
| NDa113 (PC060) | Incoming PBMC apheresis product<br>XCELLERATE I | 47% | 17% | 6% | 2.3 |
| | Monocyte-depleted PBMC | 61% | 4% | 3% | 1.8 |
| | Freeze/thawed Monocyte-depleted PBMC<br>XCELLERATE II | 63% | 4% | 1% | 1.8 |
| | Freeze-thawed PBMC apheresis product | 51% | 13% | 1% | 1.5 |
| | Post- CD3+ magnetic concentration | 76% | 1% | 0% | 1.9 |
| NDa115 (PC073) | Incoming PBMC apheresis product<br>XCELLERATE I | 59% | 17% | 2% | 1.7 |
| | Monocyte-depleted PBMC | 60% | 10% | 2% | 1.8 |
| | Freeze/thawed Monocyte-depleted PBMC<br>XCELLERATE II | 60% | 11% | 1% | 1.9 |
| | Freeze-thawed PBMC apheresis product | 53% | 12% | 1% | 2.0 |
| | Post- CD3+ magnetic concentration | 72% | 9% | 0% | 2.2 |

Cellular compositions were determined by flow cytometry according to standard protocols In addition to the simplification and streamlining of the process by elimination of the CD14+ monocyte-depletion step and the associated reagents, the magnetic concentration step in the XCELLERATE II™ process also provides a higher purity of CD3+ T-cells and a higher ratio of CD3+ CD4+:CD3+ CD8+ T-cells at the initiation of T-cell activation (Table 5.1 and Table 5.2).

Yield, Purity, Viability and Composition of Activated CD3+ T-cells Pre-harvest on Day 8 of the XCELLERATE I™ process and the XCELLERATE II™ process were also compared.

As shown in Table 5.3, the average yield, purity and viability of the CD3+ T-cells prior to harvest on day 8 are typically improved for the XCELLERATE II™ compared to the XCELLERATE I™ process.

TABLE 5.3

Yield, purity, viability and composition ot activated
CD3+ T-cells pre- harvest on day 8 of the XCELLERATE I
process and the XCELLERATE II process

| | | Pre-harvest CD3+ T-cell Product Properties | | | |
|---|---|---|---|---|---|
| Experiment Number (Donor) | XCELLERATE Process Configuration | # CD3+ T-cells | Purity CD3+ T-cells (%) | Viability (%) | CD4/CD8 Ratio* |
| NDa104 | XCELLERATE I | $65 \times 10^9$ | 95 | 97 | 1.2 |
| (PC071) | XCELLERATE II | $50 \times 10^9$ | 97 | 97 | 1.7 |
| NDa107 | XCELLERATE I | $57 \times 10^9$ | 98 | 98 | 0.8 |
| (PC074) | XCELLERATE II | $52 \times 10^9$ | 98 | 98 | 1.5 |
| NDa110 | XCELLERATE I | $41 \times 10^9$ | 96 | 96 | 1.6 |
| (PC076) | XCELLERATE II | $41 \times 10^9$ | 99 | 99 | 2.4 |
| NDa113 | XCELLERATE I | $41 \times 10^9$ | 96 | 96 | 1.3 |
| (PC060) | XCELLERATE II | $43 \times 10^9$ | 98 | 98 | 2.0 |
| NDa115 | XCELLERATE I | $31 \times 10^9$ | 96 | 96 | 1.3 |
| (PC073) | XCELLERATE II | $48 \times 10^9$ | 97 | 97 | 1.4 |
| Average ± Std Dev | XCELLERATE I | 47 ± 14 | 96 ± 2 | 97 ± 1 | 1.2 ± 0.3 |
| | XCELLERATE II | 45 ± 6 | 98 ± 1 | 98 ± 1 | 1.8 ± 0.4 |

* = Ratio of CD3+ CD4+:CD3− CD8+ T-cells

Also, as shown in Table 5.3, the XCELLERATE II™ process maintains a higher ratio of CD3+ CD4+:CD3+CD8+ T-cells throughout the process. This may be due to preferential concentration of CD3+ CD4+ cells during the magnetic concentration step (Tables 5.1 and 5.2).

"Incoming" refers to fresh, washed incoming apheresis cells. The starting cells listed in Table 5.2 for the XCELLERATE I™ process were apheresed cells that had been washed, monocyte depleted, and/or frozen/thawed. The starting cells listed in Table 5.2 for the XCELLERATE II™ process were apheresis cells that had been washed and frozen/thawed.

*=Ratio of CD3+ CD4+:CD3+ CD8+ T-cells

Table 5.3 shows that the XCELLERATE II™ process resulted in a cell product that was more pure (in terms of % CD3+ cells) than the cell product from the XCELLERATE I™ process. That is, the product cells from the XCELLERATE II™ process had an average (±std dev) CD3+ cell purity of 96%±1% while the cells from the XCELLERATE I™ process had an average purity of 93%±2%.

Also, as shown in Table 5.3, the XCELLERATE II™ process maintained a higher ratio of CD4/CD8 cells. The incoming cells had an average CD4/CD8 cell ratio of 2.2 and the product cells from the XCELLERATE II™ process had a CD4/CD8 ratio of 1.8, while the product cells from the XCELLERATE I™ process had a CD4/CD8 ratio of 1.2.

The data of Table 5.3 also shows that the XCELLERATE II™ process resulted in product cells with an average viability of 98% while the XCELLERATE I™ process resulted in product cells with an average viability of 97%.

Example III

Monocyte Depletion

Monocytes (CD14+ phagocytic cells) are removed from T-cell preparations via magnetic depletion using a variety of "irrelevant" (i.e., non-antibody coated or non-target antibody coated) Dynal beads. Depletion was performed by pre-incubating either whole blood after separation in ficol or aphereseed peripheral blood with Dynal Sheep anti-mouse M-450 beads, or Dynal human serum albumin-coated beads (M-450), or with Dynal Epoxy (M-450) beads at roughly a 2:1 bead to cell ratio. The cells and beads were incubated for periods of 1–2 hours at 22–37 degrees C., followed by magnetic removal of cells that had attached to beads or that had engulfed beads. The remaining cells were placed into culture alongside un-manipulated cells. Cells were characterized by flow cytometry for cell phenotype before and after depletion.

Example IV

Flow Cytometry Settings

A Becton Dickinson FACSCALIBUR cytometer was used for all the data collected and presented. Any flow cytometer capable of performing 3-color analysis could be used by an experienced operator to acquire identical data. For example, a FACSCAN, Vantage Cell Sorter, or other BD product would work to collect similar data. Also, Coulter products, such as the Coulter Epic Sorter would work as well.

The instrument setting given below can be used as a general guideline for instrument conformation to gather data as was done in these studies. These settings were used for the Examples provided herein; however, modifications to these settings can and should be made by an experienced instrument handler to adjust appropriately for compensation and detector voltages. Also, the use of different detection antibodies with different fluorescent tags requires unique adjustment to any particular instrument to give optimal signal separation (voltage) with minimal "bleeding-over" into other channels (e.g., compensation). A skilled flow operator, well-versed in using compensation controls, isotype controls, and with a general understanding of T-cell biology should be able to reproduce any of the data presented below.

Further it should be noted that various settings, particularly voltage settings, may vary, depending upon the efficiency of the instrument laser. For example, older lasers may require more voltage to generate a signal comparable to a newer laser. However, the data obtained, whether with more or less voltage, should reflect similar patterns in biology.

Settings used on the FACSCALIBUR™ (Becton Dickinson):

| Detector/Amps: | | | | |
|---|---|---|---|---|
| Parameter | Detector | Voltage | Amp/Gain | Mode |
| P1 | FSC | EOO | 1.30 | Lin |
| P2 | SSC | 370 | 1.00 | Lin |
| P3 | FL1 | 610 | 1.00 | Log |
| P4 | FL2 | 550 | 1.00 | Log |
| P5 | FL3 | 520 | 1.00 | Log |

Although the parameter voltages are generally constant, P3, P4, and P5 may be adjusted slightly up or down in order to achieve maximum signal separation, while maintaining a negative control signal value in or near the first decade (0–10) in signal strength in the log mode.
Threshold:
Primary parameter: FSC (forward scatter)
Value: 52
Secondary parameter: none
Compensation:
FL1-4.0% FL2
FL2-21.4% FL1
FL2-2.6% FL3
FL3-15.2% FL2

While the settings provided approximate the settings used to collect most of the data presented below, the settings may be altered and roughly equivalent data on stimulated T-cells should be generated. The general acceptable ranges for compensation at the voltages listed above are as shown below:

| FL1–FL2 | 0.4–4% |
|---|---|
| FL2–FL1 | 18–27% |
| FL2–FL3 | 2–8% |
| FL3–FL2 | 10–16% |

The determination of the particular compensation or voltage values has to be made by an experienced flow cytometer operator with the following goals:

1) Voltage: Maximization of signal separation between positive and negative signals (e.g., surface antigen marker negative vs. low levels surface antigen vs. high levels surface antigen).

2) Compensation: Minimization of interchannel interference (bleed-over) by use of compensation controls.

As voltage settings change, so do compensation settings.

Example V

Cell Proliferation and Viability Assays

Cell proliferation and viability was measured by standard Trypan Blue staining and cell counting using a hemocytometer. See FIGS. 5A–5B.

Example VI

Activation Marker Assays

CD154 is expressed on activated T-cells in a temporal manner and has been shown to be a key element in T-cells interactions via CD40 on APCs. Blocking the interaction of these two receptors can effectively alter, and even shut-off, an immune response. Aliquots of T-cells that were stimulated by concentration with 3x28 paramagnetic beads were removed from cell culture at days 3, 5, and 8 and analyzed for the level of CD154 expression. The level of CD154 expression was compared with T-cells that were depleted of monocytes but were not incubated with 3x28 paramagnetic beads (that is, the T-cells were not magnetically concentrated at culture initiation). Significant activation of the T-cells stimulated by magnetic concentration with anti-CD3 and anti-CD28 beads was shown by a three-fold increase in the level of CD154 expression on the third day of culture compared with cells that were not similarly stimulated at culture initiation. (See FIGS. 4 and 7). CD25 levels measured in a similar manner (FIG. 6) show a trend toward higher activation.

In general, marker expression was monitored over various times. In this regard cells are labeled with anti-human CD4 (Immunotech, Fullerton, Calif.), FITC coupled anti-human CD11a (Pharmingen), FITC coupled anti-human CD26 (Pharmingen), FITC coupled anti-human CD49d (Coulter), FITC coupled anti-human CD54 (Pharmingen and Becton Dickinson), FITC coupled anti-human CD95 (Pharmingen), FITC coupled anti-human CD134 (Pharmingen), FITC coupled anti-human CD25 Ab (Becton Dickinson, Fullerton, Calif.), FITC coupled anti-human CD69 Ab (Becton Dickinson), FITC or PE coupled anti-human CD154 Ab (Becton Dickinson), or FITC or PE coupled IgG1 isotype control Ab. Cells, $2 \times 10^5$ are labeled for 20 minutes at 4° C. with 2 μl of each antibody in a final volume of 30 μl, washed and resuspended in 1% parformaldehyde (Sigma, St. Louis, Mo.).

Comparison of cell surface marker molecule expression levels may be carried out by a variety of methods and thus absolute values may differ. However, when comparing two values the relative fold values may be readily calculated. For example, CD154 expression levels on T-cells generated by different "activation" methods can be measured with relative accuracy by flow cytometric means. Using a reagent, such as Becton Dickinson's anti-CD154-PE conjugate (catlogue # 340477), one can stain T-cells in resting or activated states and gauge expression levels for this marker (or others by means well known to experienced flow cytometer operators). Described herein are methods which provide for increased expression of CD154 on T-cells, both CD4+ and CD8+. By simultaneously stimulating and concentrating T-cells at the initiation of culture, as described herein, expression levels can be driven up beyond values obtained by standard 3x28 activation, on the order of a 20% to over a 100% increase in levels, as measured by mean fluorescent intensity (MFI) using flow cytometry (BD FACSCalibur and antibody described above). For example, an unstimulated CD4+ T-cell would be negative for CD154 and would therefore yield MFI values between 1–10. Upon activation by XCELLERATE I™, at 3 days post-activation, MFI values for CD154 on CD4+ T-cells might be in the 20–40 range, while the XCELLERATE II™ process might yield CD154 MFI values of 60–200. While these are not absolute values in terms of the number of CD154 molecules expressed on T-cells, there are sufficient to determine relative levels of increased expression. Accordingly, it can be demonstrated that an approximate 1.1 to 20 fold increase in CD154 levels between 1–4 days, post-activation can be demonstrated with the XCELLERATE II™ process as compared to the XCELLERATE I™ process.

Example VII

Cytokine Assays

Cells are prepared as described above. Supernatants from cells stimulated for various times are subjected to an IL-2, IL-4, INF-gamma or TNF-α ELISA according to the manufacturer's instructions (Biosource International, Sunnyvale, Calif.).

In an alternative assay, IL-2 is measured by intracellular staining of CD4 T-cells using flow cytometry. For intracellular labeling of IL-2 or IFN-γ, cells are first incubated with 1 μg/ml Monensin (Calbiochem) for 4 hours prior to assay. The cells are subsequently stained for surface proteins as described above, fixed and permeabilized using Becton Dickinson intracellular staining-kit, labeled with PE-coupled anti-human IL-2 Ab and FITC coupled anti-human IFN-γ or the corresponding control Abs as described by the manufacturer. Data acquisition and flow cytometric analysis is performed on a Becton Dickinson FACSCalibur flow cytometer using Cellquest software following the manufacturer's protocol (Becton Dickinson).

IFN-gamma concentrations were about 2, 3, 4, and in some cases 5 fold higher at day 3 when using the XCELLERATE II™ methodology as opposed to XCELLERATE I™ (data not shown). Further, TNF-alpha levels were also markedly higher (between 1.5 to 3 fold higher) up to day 5 following stimulation (data not shown) as compared with XCELLERATE I™.

Example VIII

Phenotypical Cell Analysis After Restimulation

For restimulation analysis about 5×10$^6$ cells are taken from the culture at the day of termination. In several examples, the date of termination is day 8 of culture. The cells are placed into 5 mL of X-vivo 15 media with serum and with or without IL-2 as indicated above, in one well of a six well plate. About 5×10$^6$ Dynabeads M-450 CD3/CD28 T beads to the well containing the cells and the cells and beads are placed in a 37° C., 5% CO$_2$ incubator. After two days, the samples are removed and tested for viability and analyzed by FACS to determine cell size, and cell marker and/or cytokine expression levels, such as CD25 expression levels, CD154 expression levels. Table 6 demonstrates these results below for five patient samples subject to the XCELLERATE I™ and the XCELLERATE II™ process.

Example IX

Alternative Cell Collection and Culture Protocols XCELLERATE™

Cells isolated from human blood are grown in X-vivo media (Biowhittaker Inc., Walkersville, Md.) and depending on use supplemented with or without 20 U/ml IL-2 (Boehringer Mannheim, Indianapolis, Ind.) and supplemented with 5% human serum (Biowhittaker), 2 mM Glutamine (Life Technologies, Rockville, Md.) and 20 mM HEPES (Life Technology). Jurkat E6-1 cells (ATCC, Manassas, Va.) are grown in RPMI 1640 (Life Technologies) supplemented with 10% FBS (Biowhittaker), 2 mM glutamine (Life Technologies), 2 mM Penicillin (Life Technologies), and 2 mM Streptomycin (Life Technologies).

Buffy coats from healthy human volunteer donors are obtained (American Red Cross, Portland, Oreg.). Peripheral blood mononuclear cells (PBMC) are obtained using Lymphocyte Separation Media (ICN Pharmaceuticals, Costa Mesa, Calif.) according to the manufacturers' instructions.

Peripheral blood lymphocytes (PBL) are obtained from the PBMC fraction by incubation in culture flask (Costar, Pittsburgh, Pa.) with uncoated Dynabeads (Dynal, Oslo, Norway), 10$^8$ cells/ml, 2 beads/cell, 2 h at 37° C. Monocytes and macrophages can be removed by adherence to the culture flask. Alternatively, they can be removed by phagocytosing the paramagnetic beads and then depleting these cells by magnetic cell separation according to the manufacture's instruction (Dynal). CD4$^+$ cells are purified from the PBL fraction by incubation with 10 μg/ml of monoclonal antibodies against CD8 (clone G10-1), CD20 (clone IF5), CD14 (clone F13) and CD16 (Coulter), 10$^8$ cells/ml, 20 min at 4° C. After washing, cells are treated with sheep anti-mouse Ig-coupled Dynabeads (10$^6$ cells/ml, 6 beads/cell, 20 min at 4° C.) and then depleted twice via magnetic cell separation. The purity of CD4$^+$ cells are routinely 91–95% as measured by Flow cytometry.

TABLE 6

Results of the Re-stimulation Assay for XCELLERATED T-cells Produced Using the XCELLERATE I ™ and the XCELLERATE II ™ Processes

| Experiment Number (Donor) | Process Configuration | Cell Size (FSC) | | CD25 (MFI) | | CD154 (MFI) | |
|---|---|---|---|---|---|---|---|
| | | T = 0 | T = 48 hr | T = 0 | T = 48 hr | T = 0 | T = 48 hr |
| NDa104 (PC071) | XCELLERATE I | 393 | 607 | 104 | 478 | 6 | 37 |
| | XCELLERATE II | 404 | 659 | 115 | 544 | 12 | 70 |
| NDa107 (PC074) | XCELLERATE I | 386 | 596 | 59 | 585 | 6 | 121 |
| | XCELLERATE II | 380 | 607 | 62 | 721 | 10 | 109 |
| NDa110 (PC076) | XCELLERATE I | 425 | 501 | 111 | 600 | 10 | 39 |
| | XCELLERATE II | 390 | 445 | 97 | 434 | 15 | 36 |
| NDa113 (PC060) | XCELLERATE I | 399 | 630 | 66 | 659 | 8 | 32 |
| | XCELLERATE II | 411 | 633 | 113 | 816 | 12 | 145 |
| NDa115 (PC073) | XCELLERATE I | 433 | 514 | 105 | 247 | 13 | 10 |
| | XCELLERATE II | 408 | 569 | 81 | 369 | 20 | 36 |
| Average ± Std Dev (n = 5) | XCELLERATE I | 407 | 570 ± 58 | 89± 21 | 514 ± 163 | 9± 3 | 48± 43 |
| | XCELLERATE II | 399 ± 13 | 583 ± 84 | 94± 22 | 577 ± 189 | 14± 4 | 79± 48 |

Dendritic cells are generated by first adhering PBMC to a culture flask (Costar), $10^8$ cells/ml, 2 h at 37° C. (without Dynabeads). After extensive washing, adherent cells are cultured for 7 days in media containing 500 U/ml GM-CSF (Boehringer Mannheim) and 12.5 U/ml IL-4 (Boehringer Mannheim). The resulting cell population is weakly adherent and expresses surface markers characteristic of dendritic cells (e.g., expresses HLA-DR, CD86, CD83, CD11c and lacks expression of CD4). (All antibodies obtained from Becton Dickinson, San Jose, Calif.).

Other techniques can utilize human peripheral blood lymphocytes containing T-cells that are incubated in tissue culture plates and/or tissue culture flasks (Baxter bags), or other common culture vessels in media, which could be composed of RPMI, X-Vivo 15, or some other T-cell culture media. Although not required for the activation and growth of T-cells, glutamine and HEPES are added to the culture media. Fetal bovine serum (10% final), human A/B serum (5%), or autologous human serum (5%) is added to culture media. The percentage of serum may vary without greatly affecting T-cell biology or culture outcome. In some instances, recombinant human IL-2 is added to cultures. In some instances, phagocytic CD14+ cells and other phagocytic cells are remove by magnetic depletion as described, infra. Beads having co-immobilized upon their surface anti-CD3 and anti-CD28 (3×28 beads) are added at a 3:1 bead-:cell ratio. In some instances, 3×28 beads are added at a 1:1 bead:cell ratio. In other instances, the 3×28 beads are added sequentially over the first 5 days of culture with final ratios of 1:1 at day 1, 1:5 at days 3 and 5. Cultures are maintained at 37 degrees C. at 5–7% $CO_2$. Cells are removed at several timepoints over a 14 day period to determine cell density (cell number), cell size, and cell surface phenotype as measured via flow cytometric analysis of a variety of surface antigens. Supernatants are also collected from cultures to determine cytokine secretion profiles, including, but not limited to: IL-2, IL-4, IFN-γ, TNF-α. As activated cells grow and divide, cultures are maintained at 0.2–2×$10^6$ CD3+ T-cells/ml. When T-cell density exceeds roughly 1.5×$10^6$/ml, cultures are split and fed with fresh media so as to give a cell density in the 0.2–1.4×$10^6$/ml range. At roughly 2 hours to about 14 days following initial stimulation, when activated T-cells are shown to be entering a more quiescent phase (e.g., CD25 levels diminishing, cell size as determined by forward scatter is diminishing, rate of cell division may be reduced), cells are either infused into the subject or re-stimulated with one of the following stimuli:
1) No stimulus
2) Phytohemagglutinin (PHA) 2 μg/ml
3) (3×28 beads) at a 1:1 bead/cell ratio Cells are again analyzed over time for cell phenotype and activation/functional state. Supernatants are again collected for secreted cytokine analysis.

Cells were stimulated by three different methodologies 1) Dynabeads (M-450) covalently coupled to anti-CD3 (OKT-3) and anti-CD28 (9.3) antibodies (3×28 beads) according to the manufacturer's instructions (Dynal), 3 beads/cell, 2) Ionomycin (Calbiochem, La Jolla, Calif.) (100 ng/ml) and phorbol 12-myristate-13-acetate (PMA) (Calbiochem) (10 ng/ml), 3) allogeneic dendritic cells (25,000 dendritic cells/200,000 CD4 cells). All cells are stimulated at a concentration of $10^6$ cell/ml. Proliferation assays are conducted in quadruplicate in 96 well flat-bottom plates. Cells are stimulated at $10^6$ cells/ml in a final volume of 200 μl. Proliferation is measured by MTT assay (MTT assay kit, Chemicon International Inc., Temecula, Calif.) at day 3 (stimulation method 1 and 2) or at day 6 (stimulation method 3), and results are presented as mean value of quadruplicates. PBL cultures or purified CD4+ cell cultures are stimulated with 3×28 beads, ionomycin/PMA, or allogenic dendritic cells.

Figure 8A:
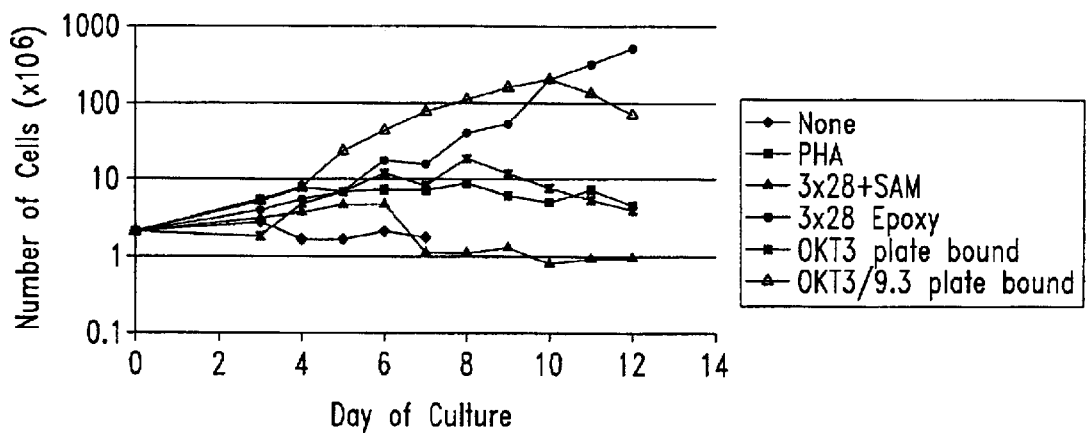
FIGS. 8A and 8B are plots illustrating growth of human peripheral blood T-cells following stimulation with anti-CD3 and anti-CD28 co-immobilized beads utilizing process set forth in Example IX.
Figure 8B:
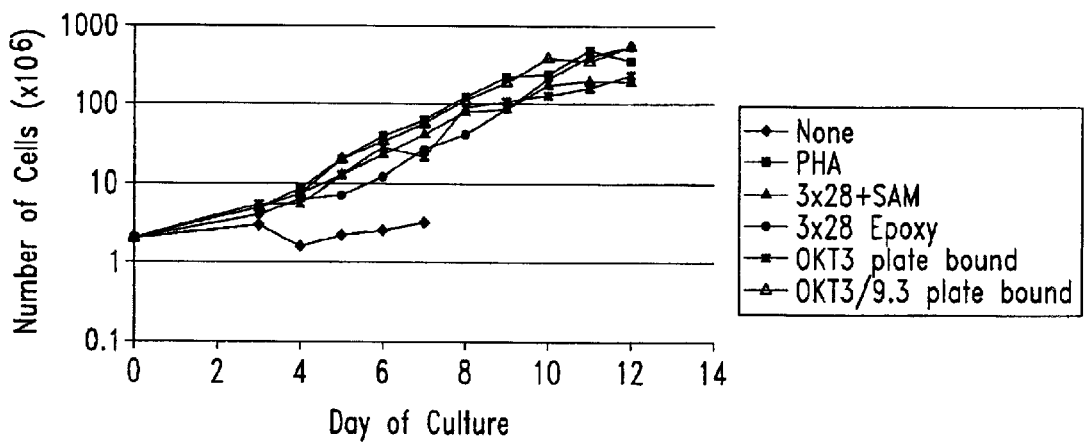
Figure 9:
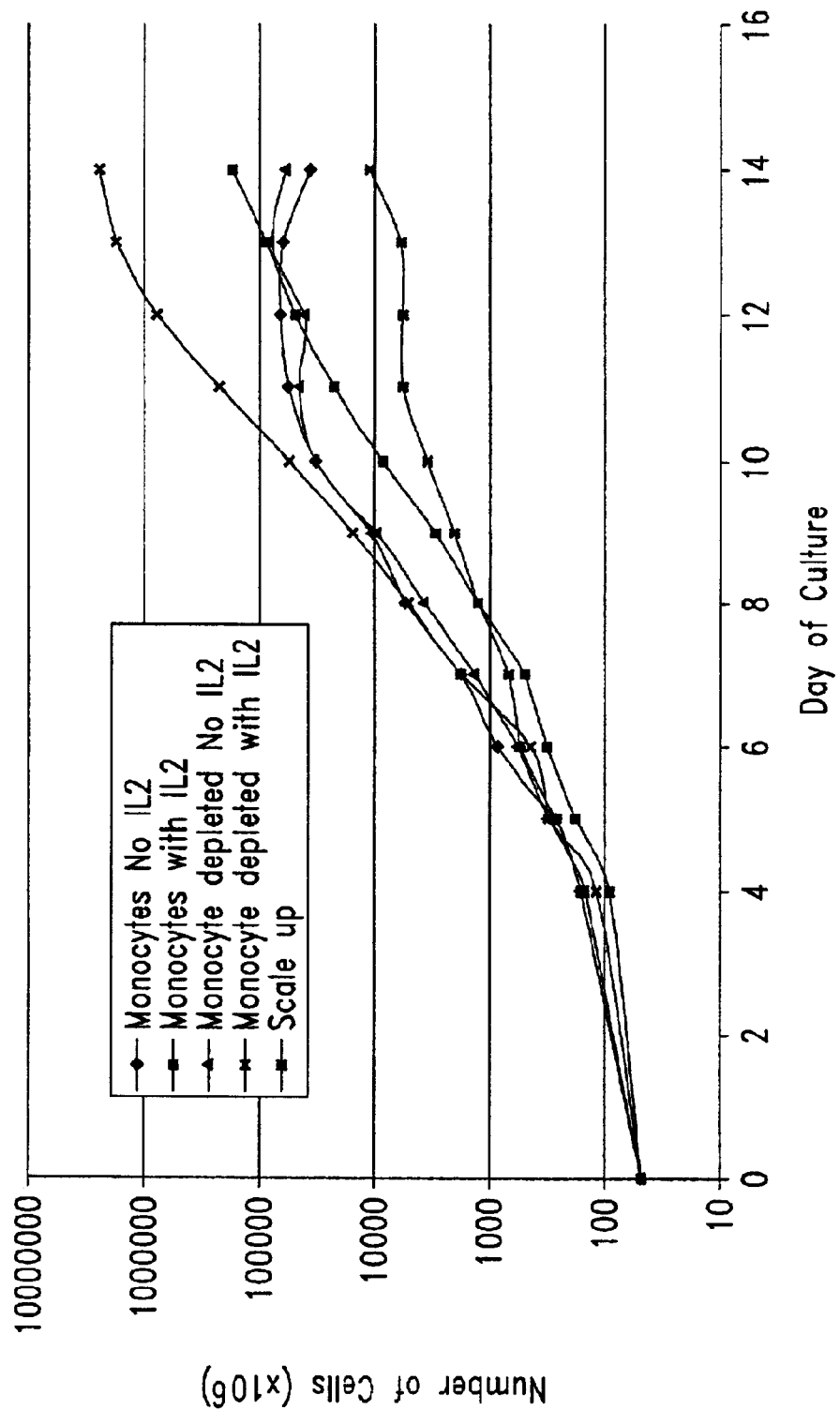
FIG. 9 is a plot illustrating growth of human peripheral blood T-cells following stimulation with anti-CD3 and anti-CD28 co-immobilized beads +/– recombinant human IL-2 at 10 u/ml and +/– monocyte depletion. All cells were cultured in Baxter Lifecell Flasks (300 ml). Scale up refers to a 300 ml flask culture (No IL-2/Monocyte depleted) that was expanded up to a Baxter Lifecell 3 Liter flask.

As demonstrated by FIGS. 8A–8B, cell numbers (Coulter counter) increase dramatically following stimulation with PHA, 3×28 beads (anti-CD3 and anti-CD28 co-immobilized on beads) attached to the beads via sheep anti-mouse (SAM), 3×28 beads with the antibodies covalently attached to the beads, or antibodies singly or dually immobilized on a plate. FIG. 9 also demonstrates increases in cell numbers following stimulation with covalently immobilized anti-CD3 and anti-CD28 on beads+/−monocyte depletion and +/−20 units of IL-2.

Example X

Monocyte Depletion Via Magnetic Depletion

Monocytes (CD14+ phagocytic cells) are removed from T-cell preparations via magnetic depletion using a variety of "irrelevant" (i.e., non-antibody coated or non-target antibody coated) Dynal beads. Depletion was performed by pre-incubating ficolled whole blood, or apheresed peripheral blood with roughly 2:1 bead to cell ratio of Dynal Sheep anti-mouse M-450 beads, or Dynal human serum albumin-coated beads (M-450), or with Dynal Epoxy (M-450) beads for periods of 1–2 hours at 22–37 degrees C., followed by magnetic removal of cells which had attached to beads or engulfed beads. The remaining cells were placed into culture alongside un-manipulated cells. Cells were characterized by flow cytometry for cell phenotype before and after depletion. FIG. 9 demonstrates increased proliferation in the absence of monocytes.

Example XI

Pre-Activation and Post-Activation Kinetic Timecourse Studies

A series of experiments were performed in which human T-cells, isolated either from whole blood or from apheresed peripheral blood, were cultured under a variety of conditions. Those conditions include:
1) No stimulation
2) Stimulation with phytohemagglutinin (PHA) at 2 μg/ml.
3) Stimulation with 3×28 Dynabeads (beads having anti-CD3 and anti-C28 beads conjugated thereto) at 3:1 or 1:1 bead-to-T-cell ratio.
4) Stimulation or culture in the presence or absence of exogenously added recombinant human IL-2 at 10 U/ml (5 ng/ml).
5) Culture in the presence of monocytes (CD14+ phagocytic cells) or cultured following removal of aforementioned cells via magnetic depletion using a variety of "irrelevant" Dynabeads. Depletion was performed as illustrated in Example 2.

The following cell surface markers were analyzed by flow cytometry to determine cell phenotype and activation state: CD2, CD3, CD4, CD8, CD14, CD19, CD20, CD25, CD45RA, CD45RO, CD54, CD62L, CDw137 (41BB), CD154. Cell size is also examined, as determined by forward scatter profiles via flow cytometry.

Markers, such as CD2, CD3, CD4, CD8, CD14, CD19, CD20, CD45RA, and CD45RO are used to determine T, B, and monocyte lineages and subpopulations, while forward scatter, CD25, CD62L, CD54, CD137, CD154 are used to determine activation state and functional properties of cells.

Human peripheral blood lymphocytes containing T-cells were prepared as described in Example IX. Cells are analyzed over time for cell phenotype and activation/functional state. Supernatants are collected for secreted cytokine analysis. FIGS. 8 and 9 demonstrates general growth characteristics of human T-cells following activation with 3×28 beads+/−recombinant human IL-2 at 10 u/ml and +/−monocyte depletion. All cells were cultured in Baxter Lifecell Flasks (300 ml). The one plot labeled "Scale up" refers to a 300 ml flask culture (No IL-2/Monocyte depleted) that was expanded up to a Baxter Lifecell 3 liter flask. The graph demonstrates an approximate 2–4 log expansion of human T-cells under the various conditions.

Figure 10:
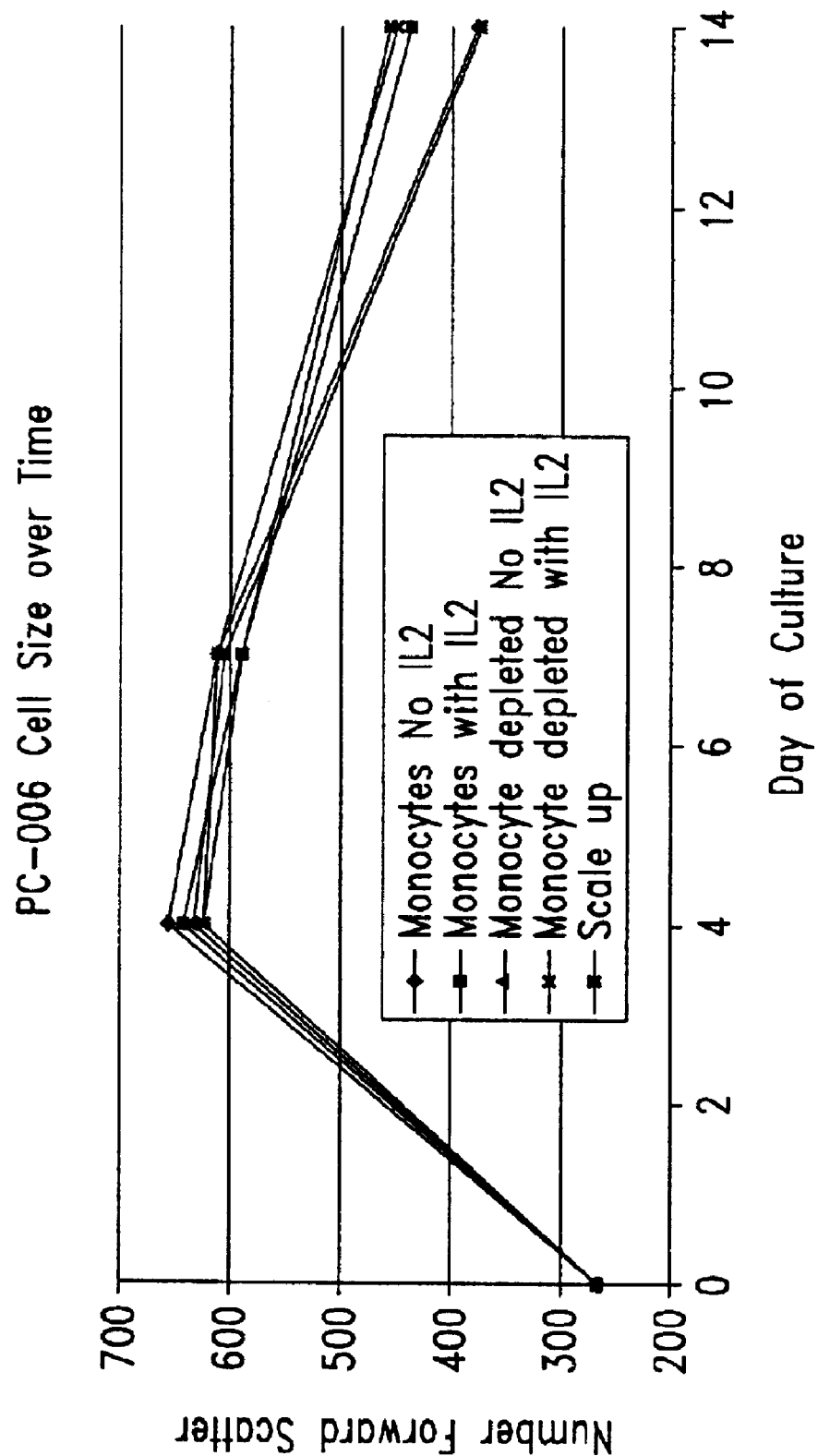
FIG. 10 is a plot demonstrating the kinetic analysis of cell size as determined by forward scatter flow cytometry profiles over time.

FIG. 10 shows the kinetic analysis of cell size as determined by forward scatter flow cytometry profiles over time. T-cell are seen to increase in size shortly after activation and subsequently decrease in size so that by day 14 they demonstrate smaller forward scatter profiles, indicating a more quiescent state.

Figure 11A:
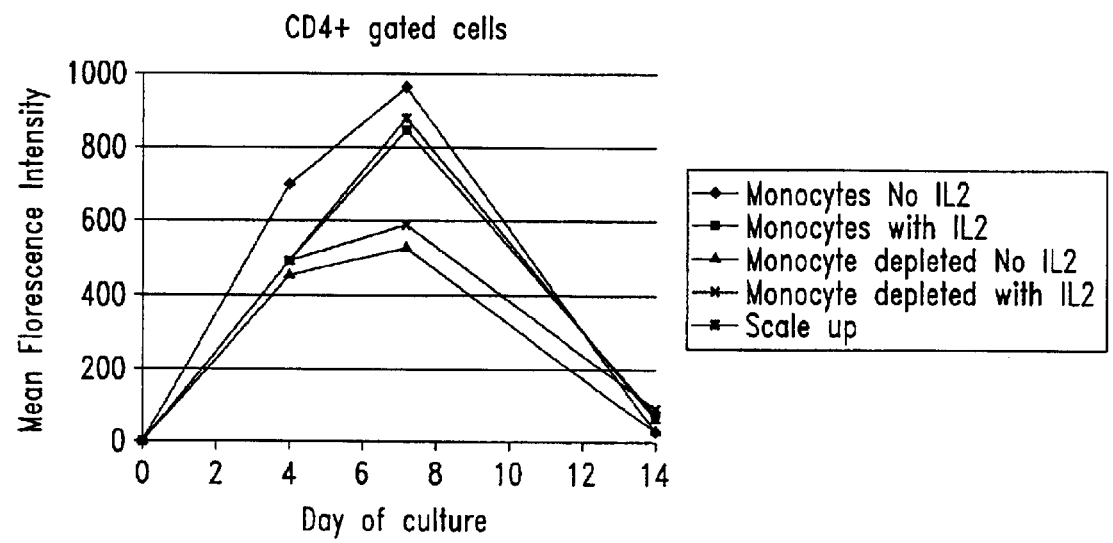
FIGS. 11A and 11B are plots representing CD25 expression over time following initial stimulation with anti-CD3 and anti-CD28 co-immobilized beads.
Figure 11B:
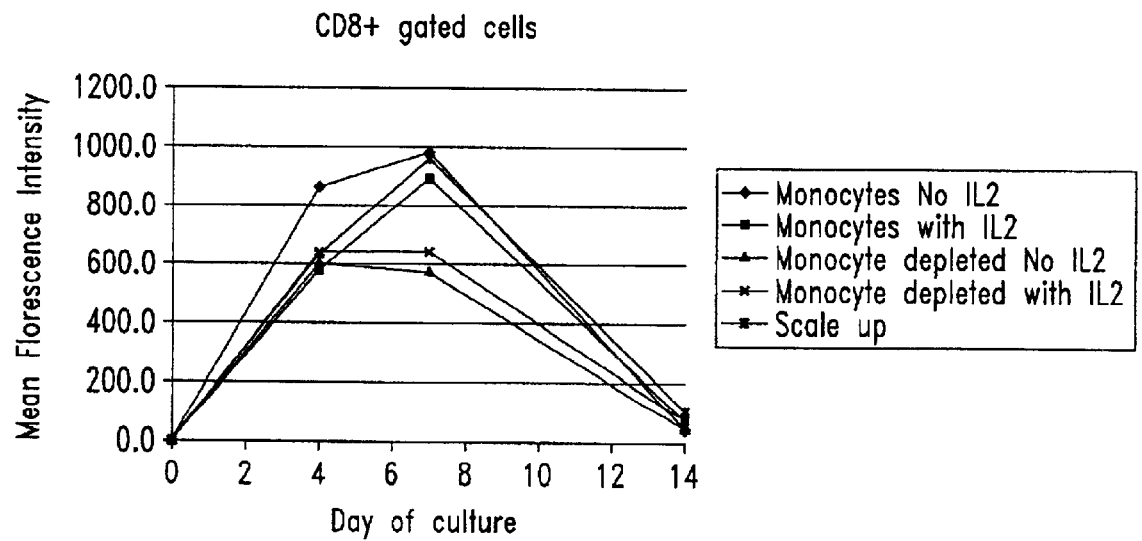

FIG. 11 shows IL-2 receptor (CD25) expression over time following 3×28 bead stimulation. Both $CD4^+$ and $CD8^+$ T-cells show an early increase in receptor level. By day 14, CD25 expression levels are greatly reduced on a majority of T-cells, indicating a more quiescent state.

Figure 12:
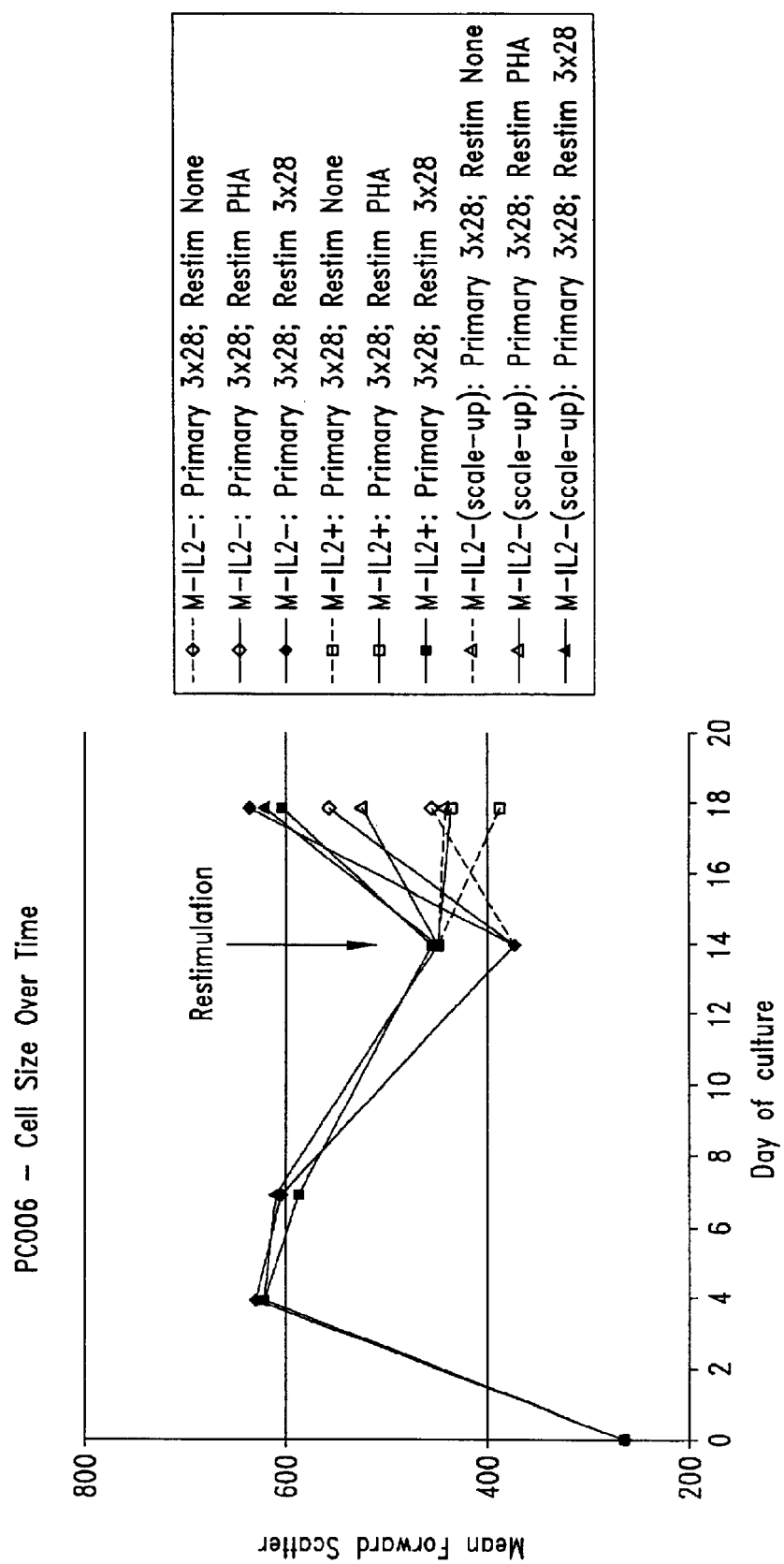
FIG. 12 is a plot illustrates changes in cell size as determined by forward scatter flow cytometry profiles over time following primary and secondary stimulation.
Figure 13A:
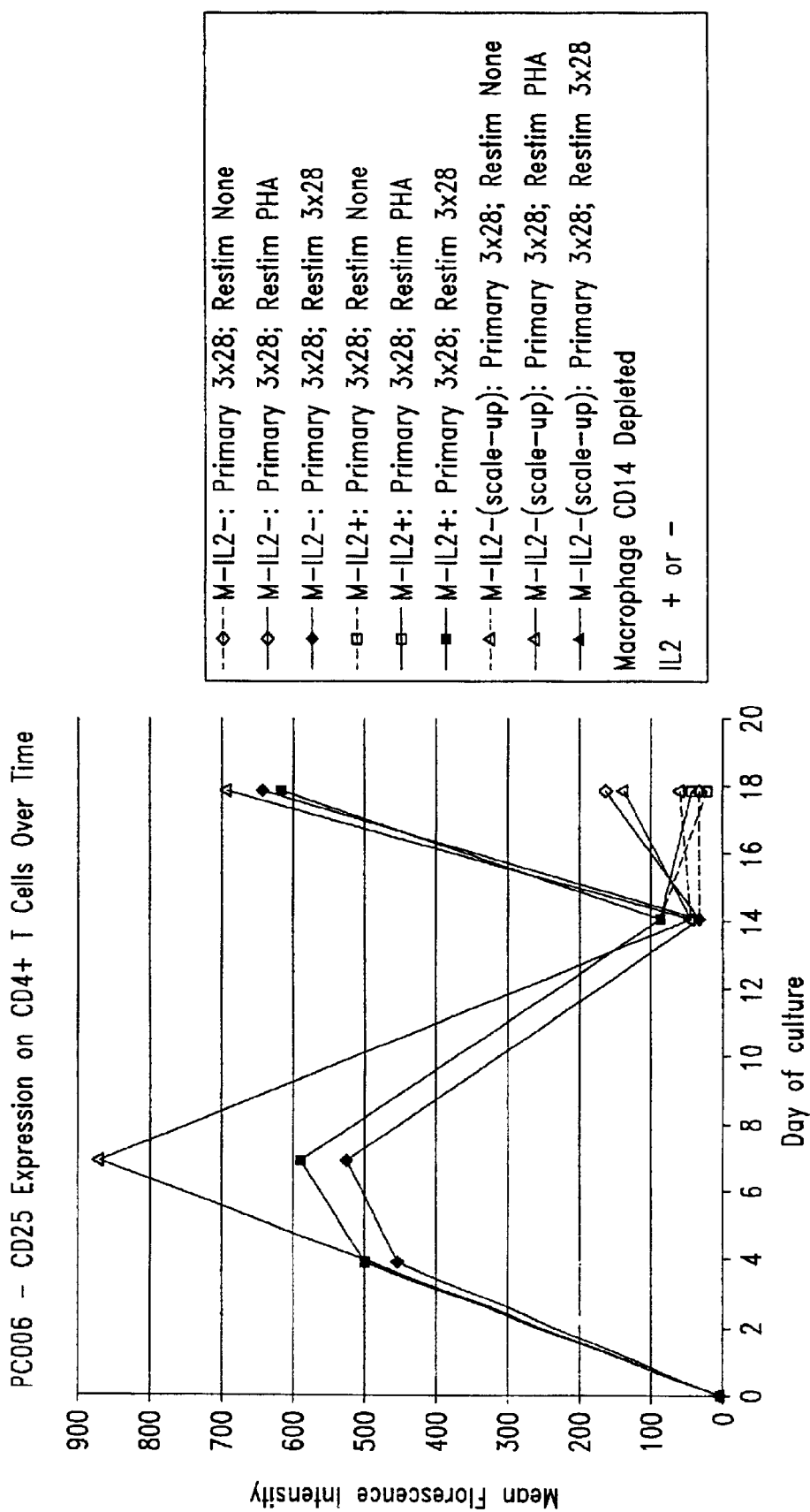
FIGS. 13A and 13B are plots representing CD25 expression over time following primary and secondary stimulation.
Figure 13B:
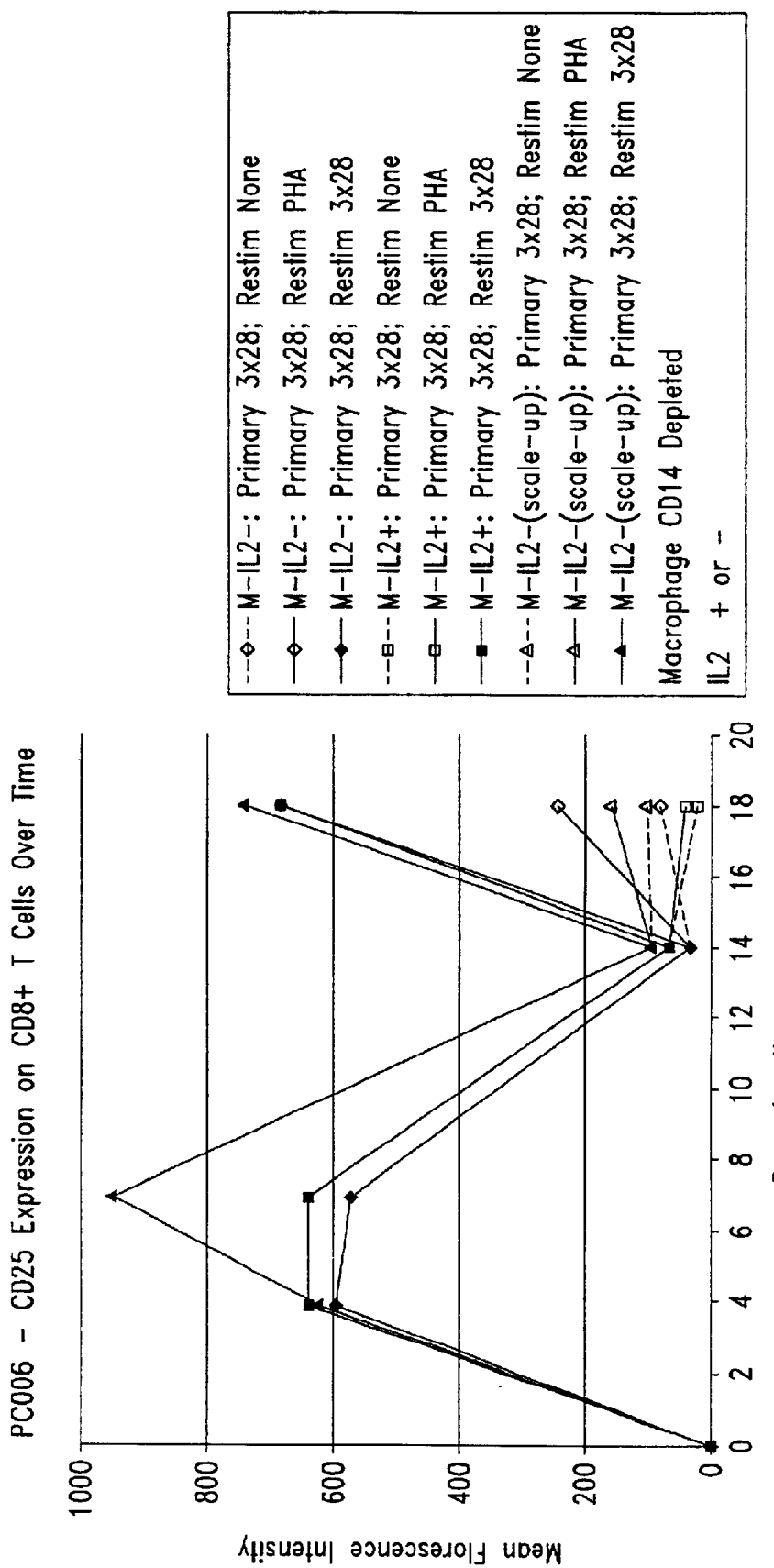
Figure 14A:
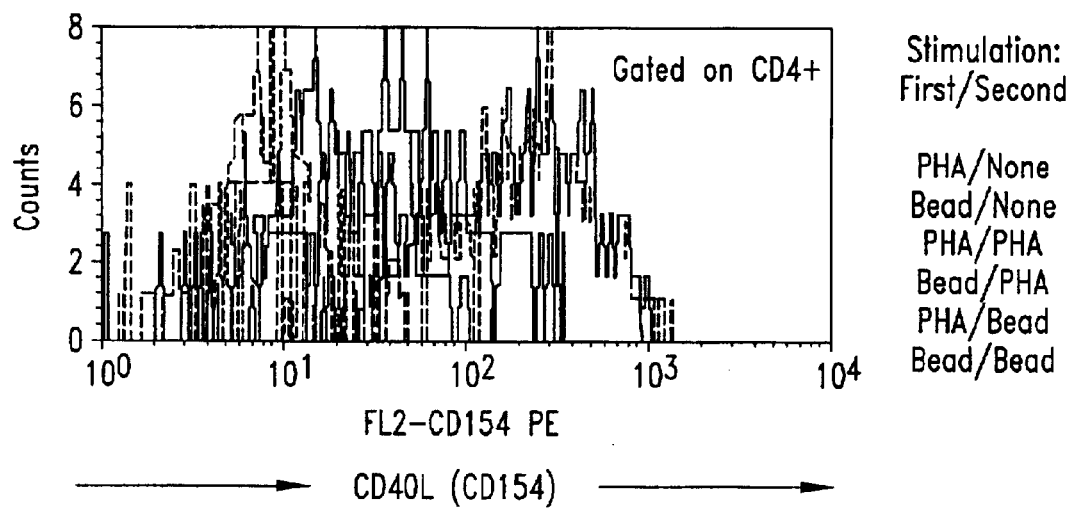
FIGS. 14A and 14B are flow cytometry data plots representing CD154 expression following secondary stimulation, wherein primary and secondary stimulation sources were varied.
Figure 14B:
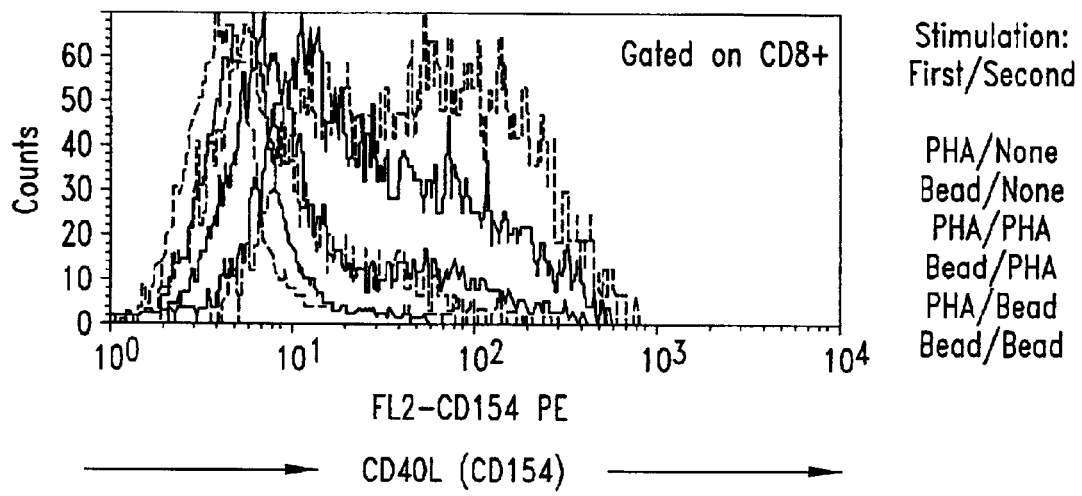
Figure 15:
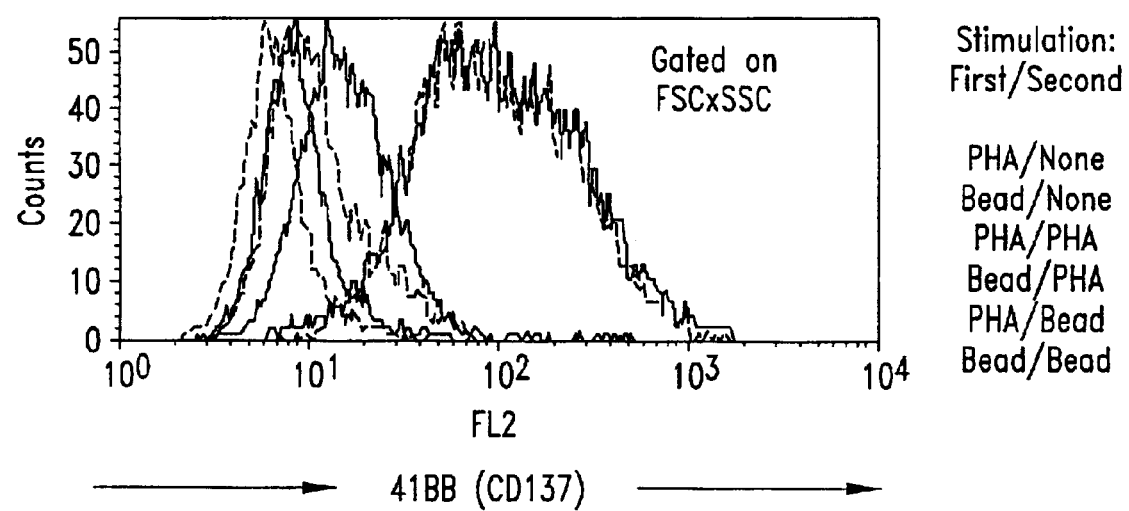
FIG. 15 is a flow cytometry data plot representing CD137 expression on all expanded T-cells in sample following secondary stimulation.
Figure 16A:
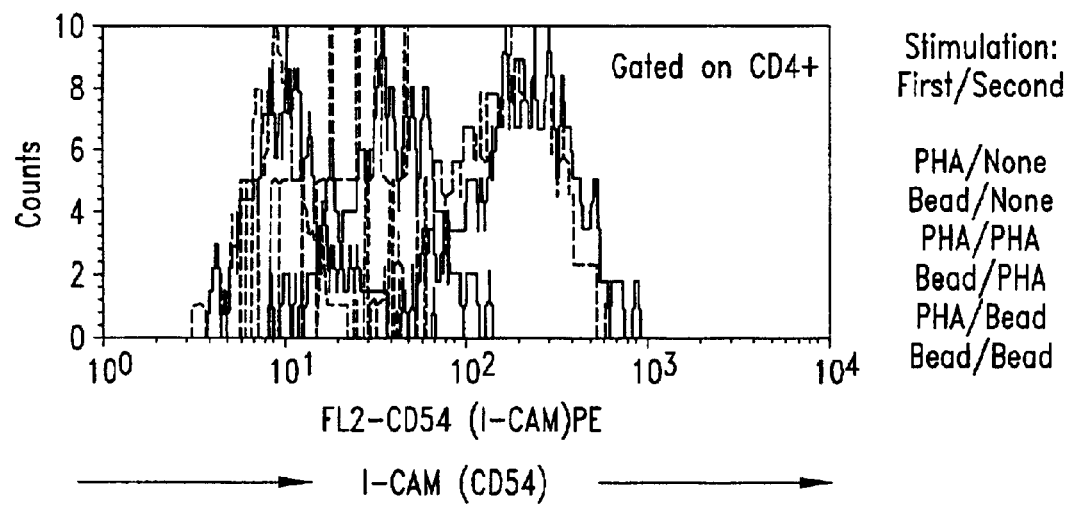
FIGS. 16A and 16B are flow cytometry data plots representing CD54 expression following secondary stimulation, wherein secondary stimulation sources were varied.
Figure 16B:
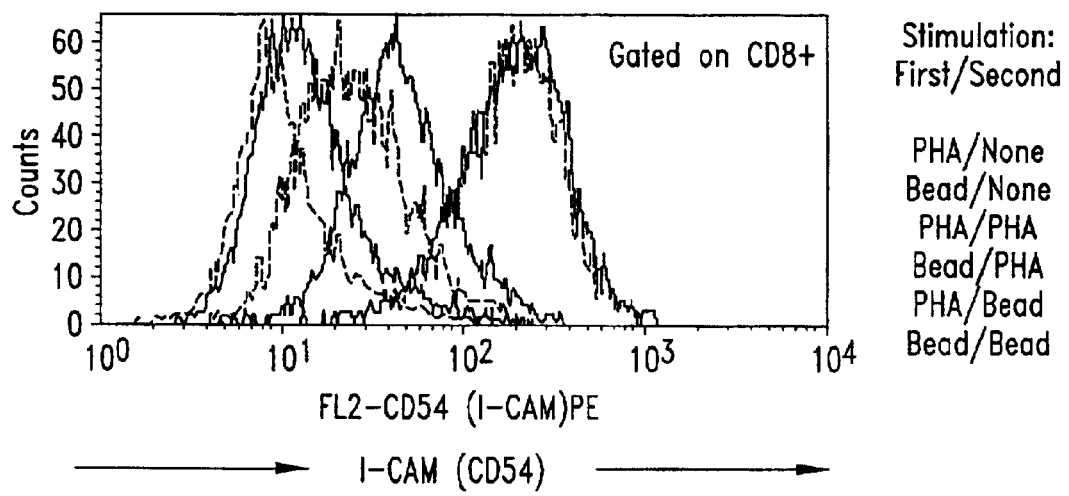
Figures 17A, 17B:
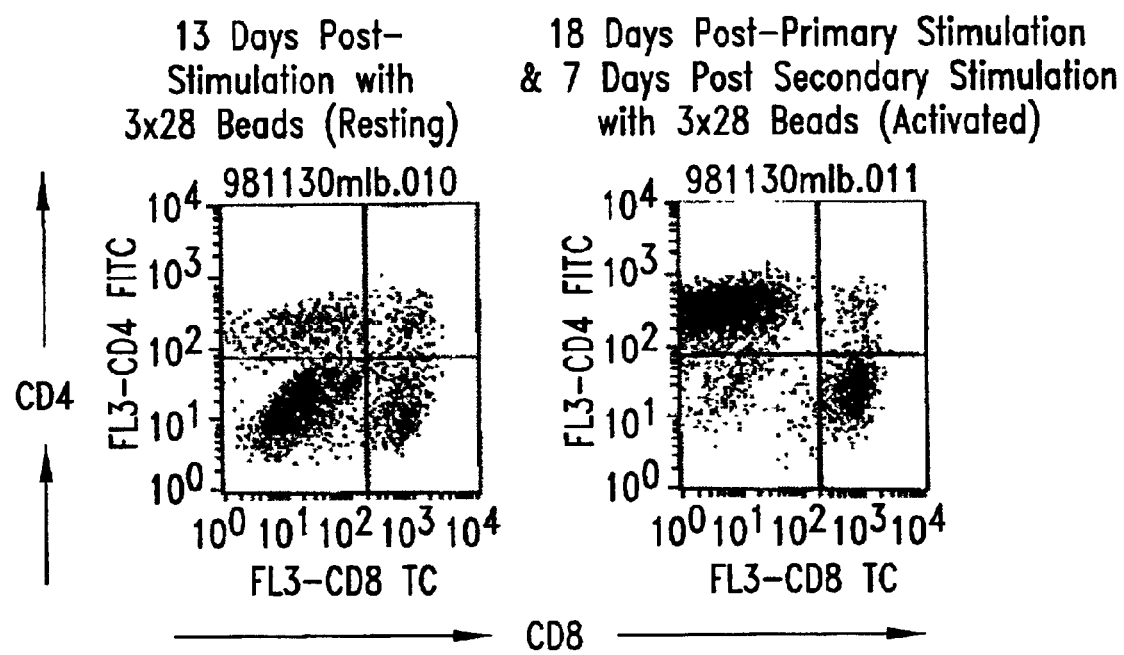
FIGS. 17A–17D are flow cytometry data plots representing cell phenotypes as well as CD154 and CD137 expression following secondary stimulation by anti-CD3 and anti-CD28 coupled beads of T-cells obtained from a patient with B-cell chronic lymphocytic leukemia.
Figure 17C:
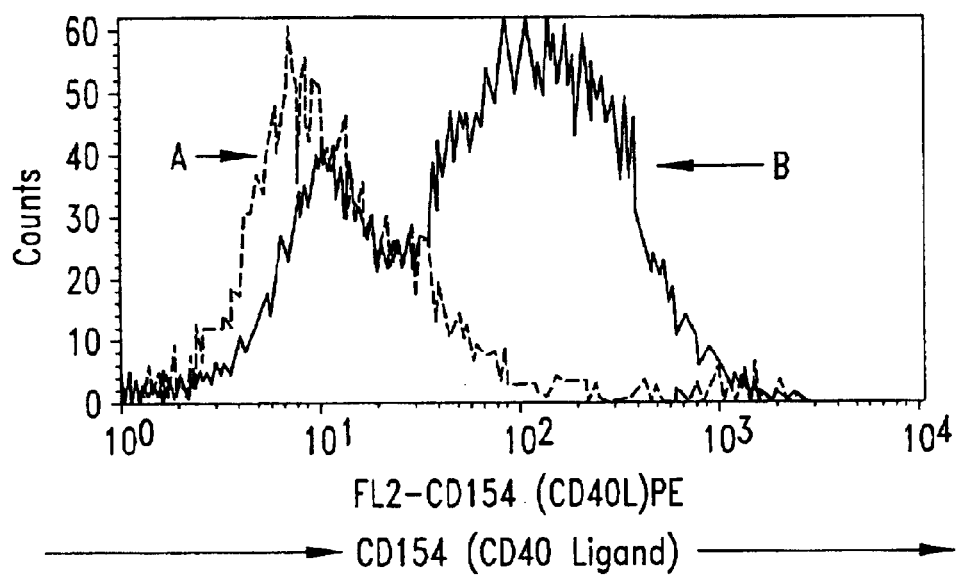
Figure 17D:
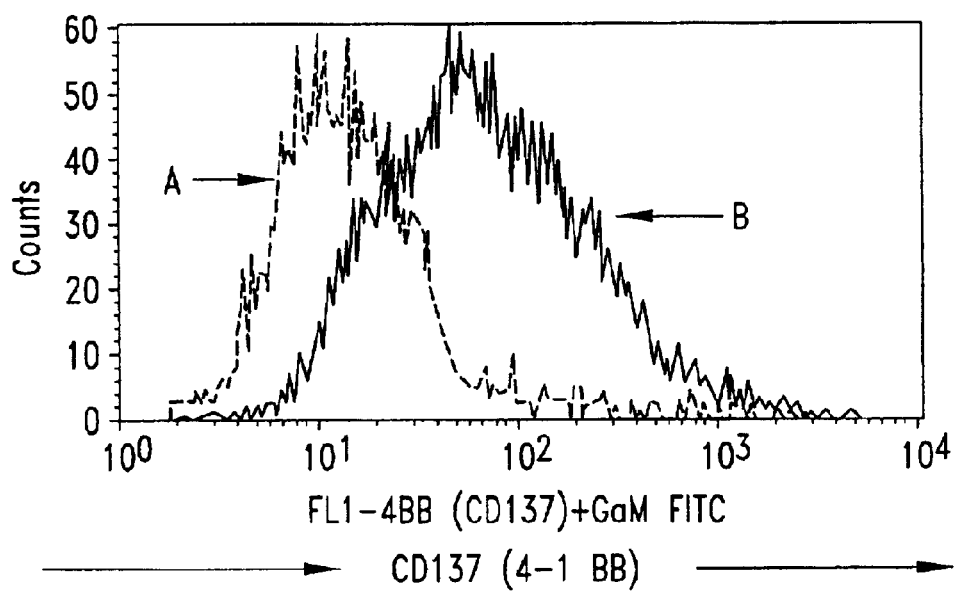
Figure 18A:
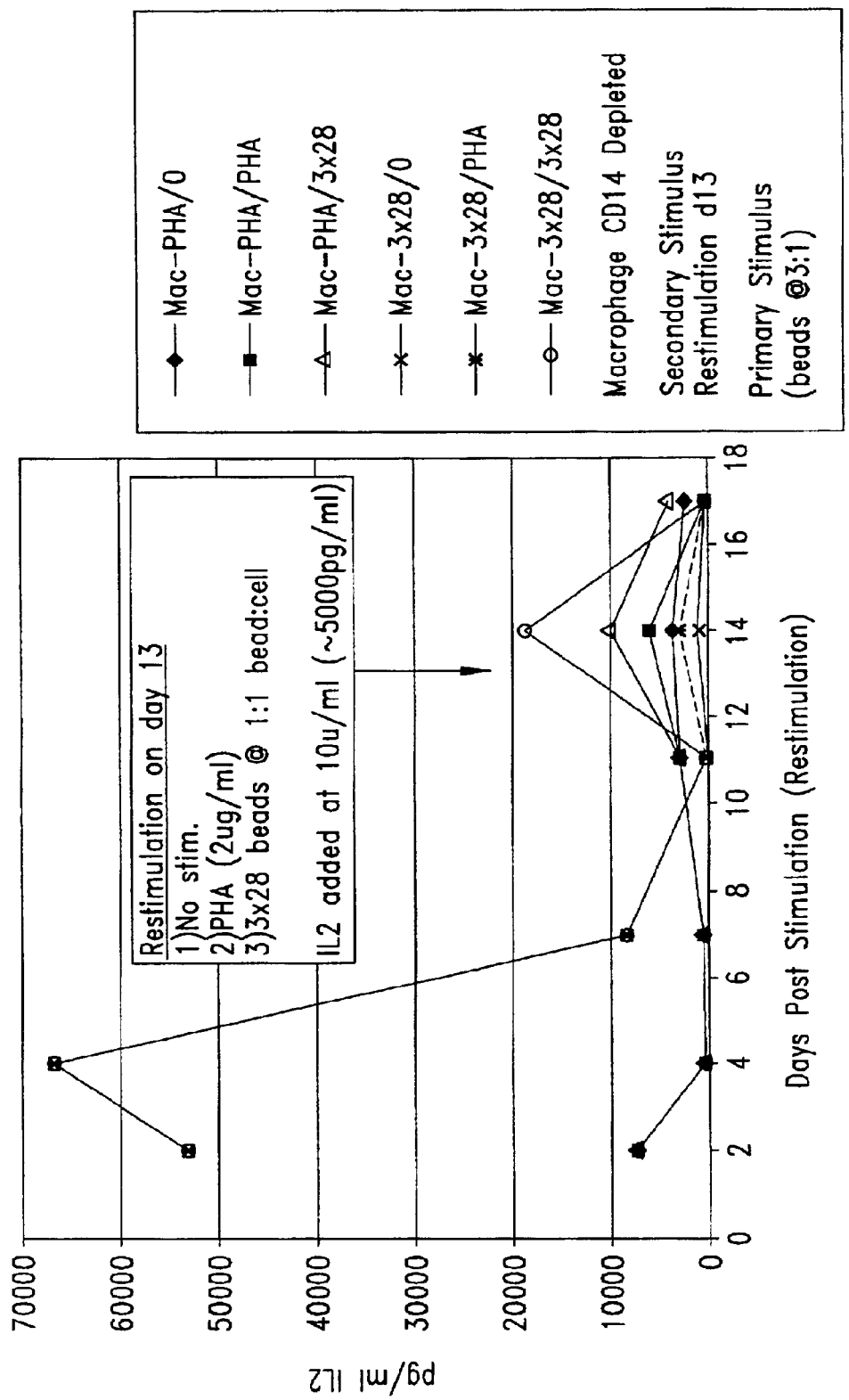
FIGS. 18A–18C are plots representing the expression over time of IL-2 (18A), Interferon gamma (IFN-γ) (18B), and IL-4 (18C) following primary and secondary stimulation of T-cells from normal donors.
Figure 18B:
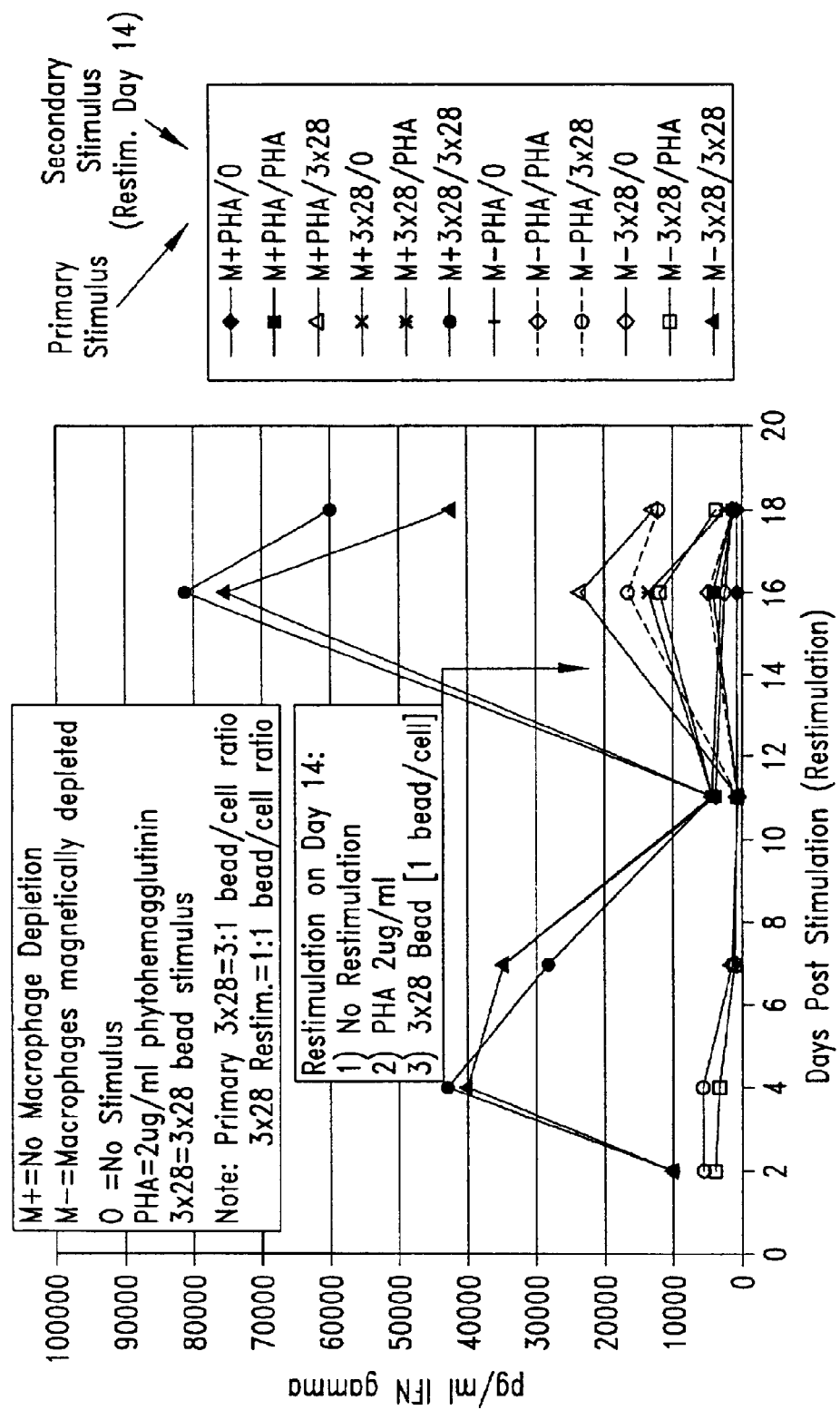
Figure 18C:
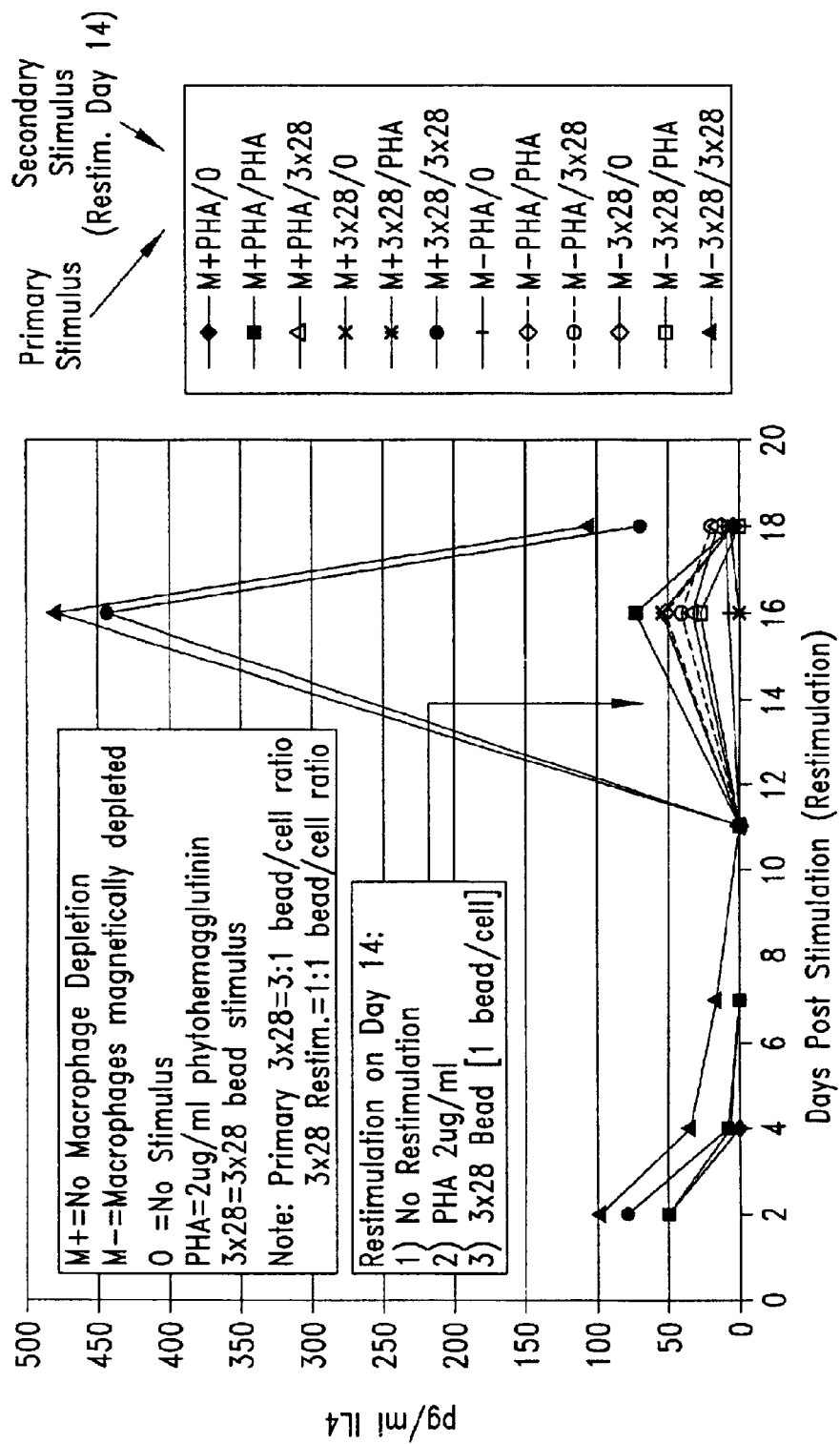
Figure 19A:
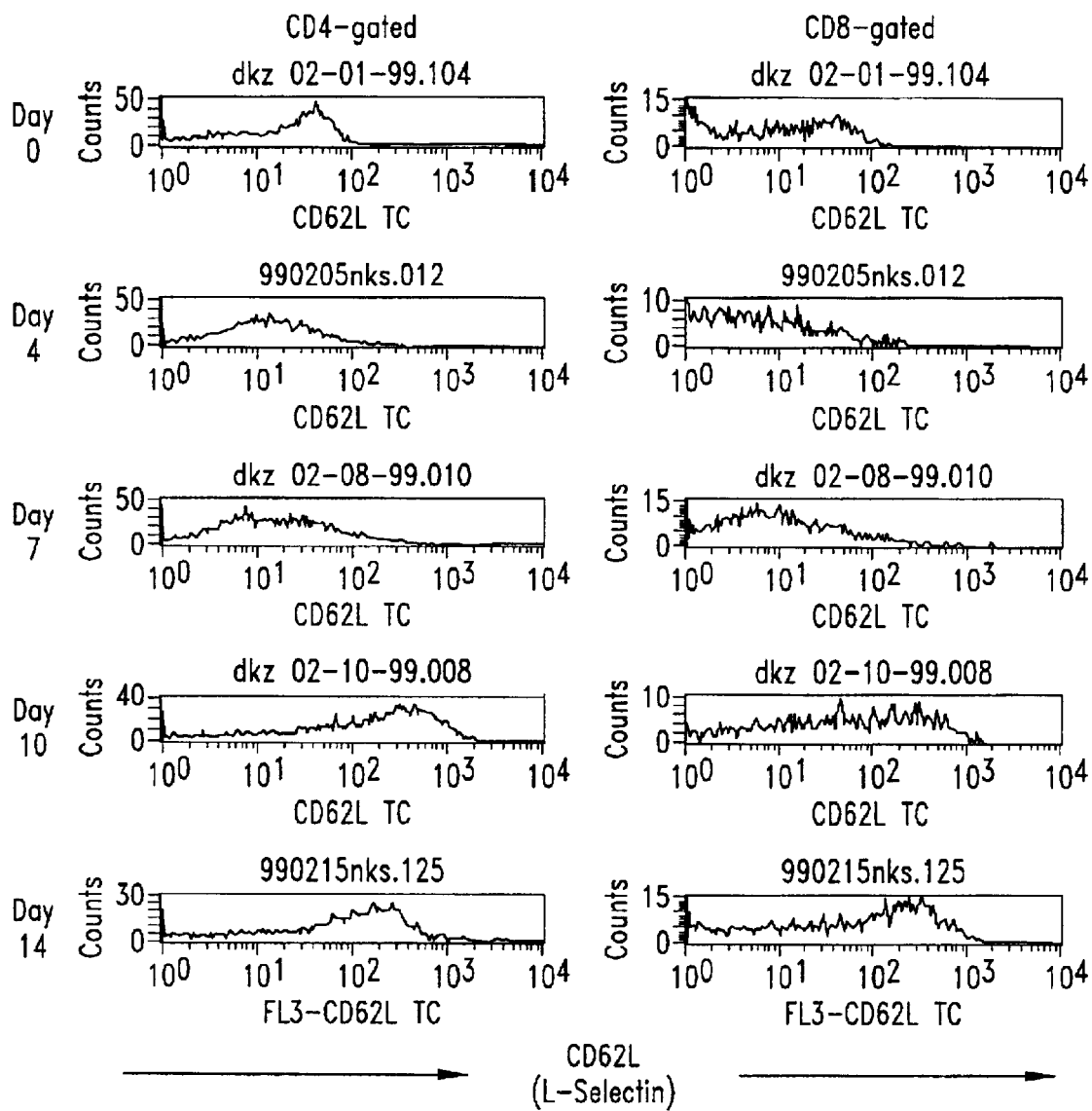
FIGS. 19A–19B are plots representing expression over time of CD62L following stimulation with anti-CD3 and anti-CD28 coupled beads.
Figure 19B:
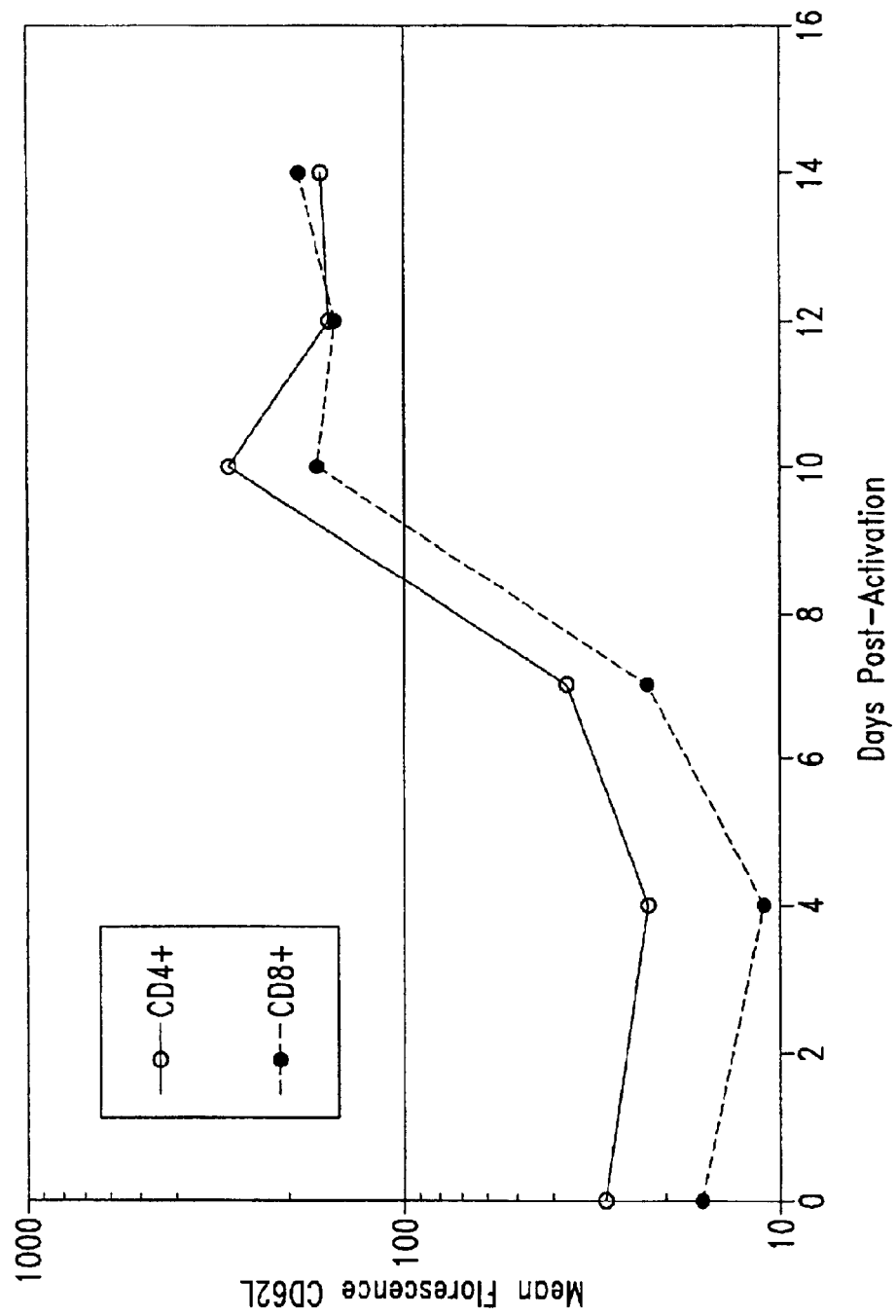
Figure 20:
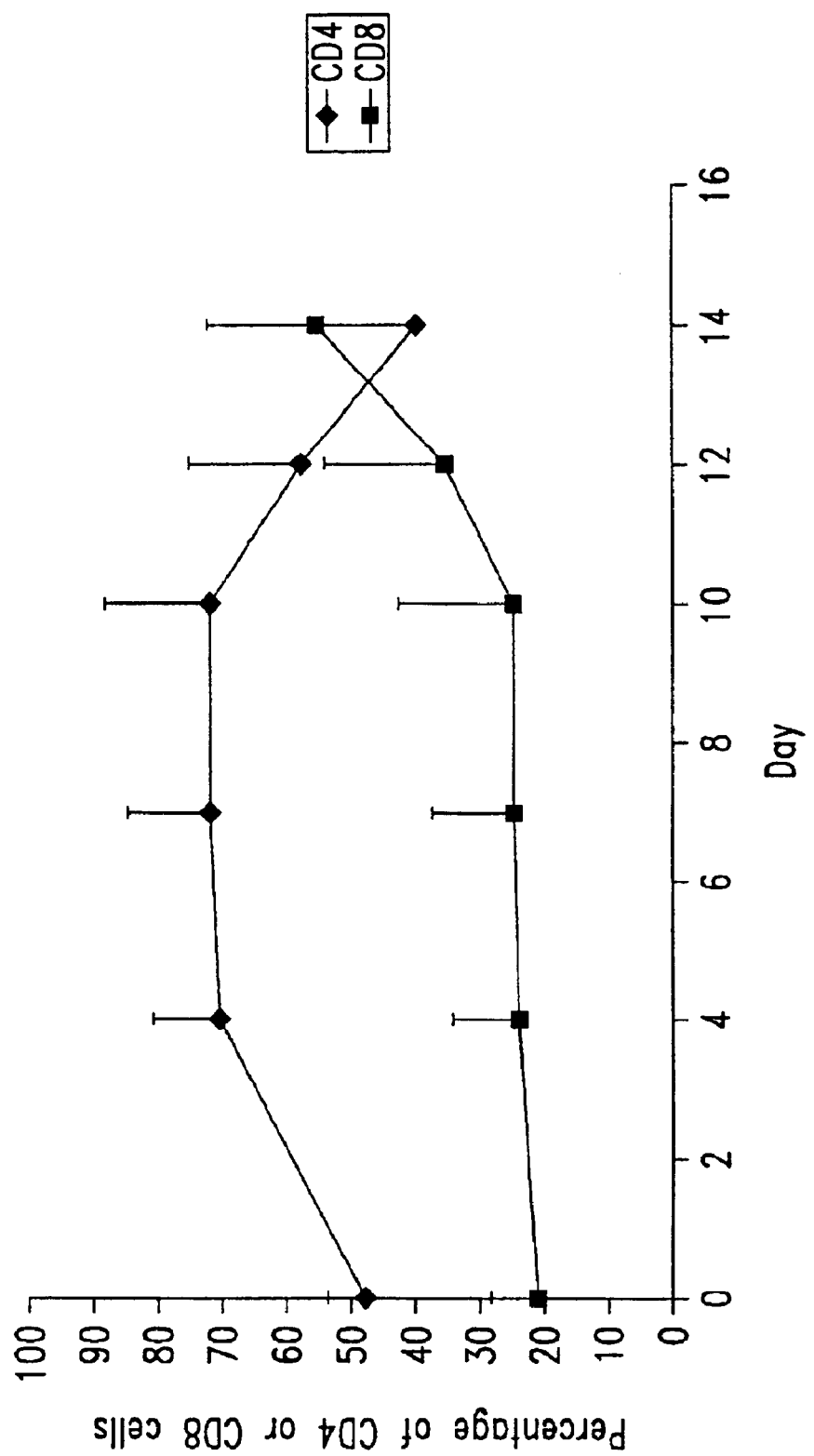
FIG. 20 is a plot depicting the percentage of CD4 or CD8 cells following stimulation with anti-CD3 and anti-CD28 co-immobilized beads.
Figure 21A:
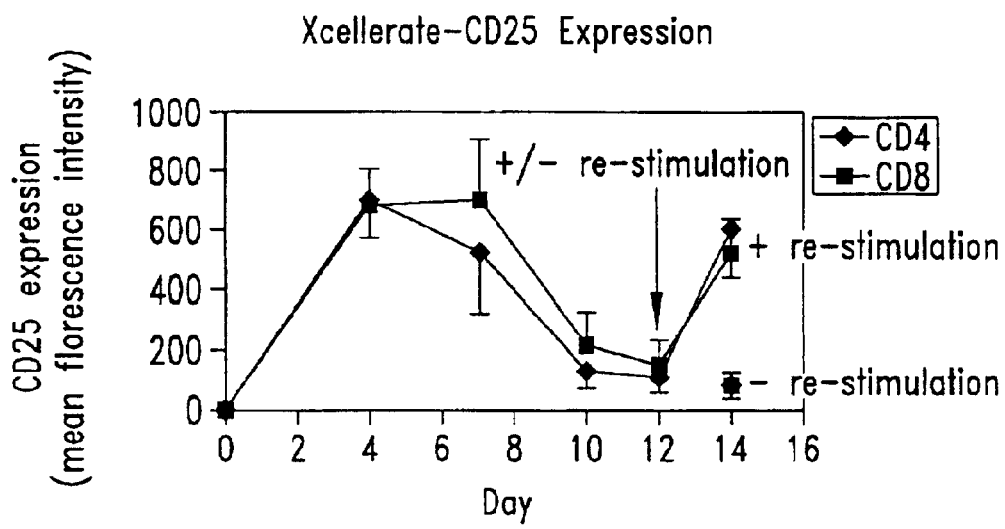
FIGS. 21A–21B are plots representing flow cytometry data as a function of mean fluorescence intensity of CD25 and CD154 expression, respectively following stimulation with anti-CD3 and anti-CD28 co-immobilized beads and +/− re-stimulation utilizing process in Example IX.
Figure 21B:
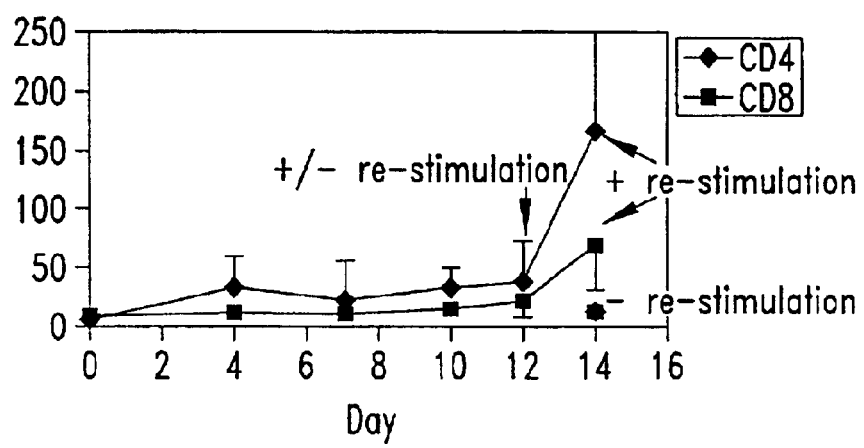
Figure 22A:
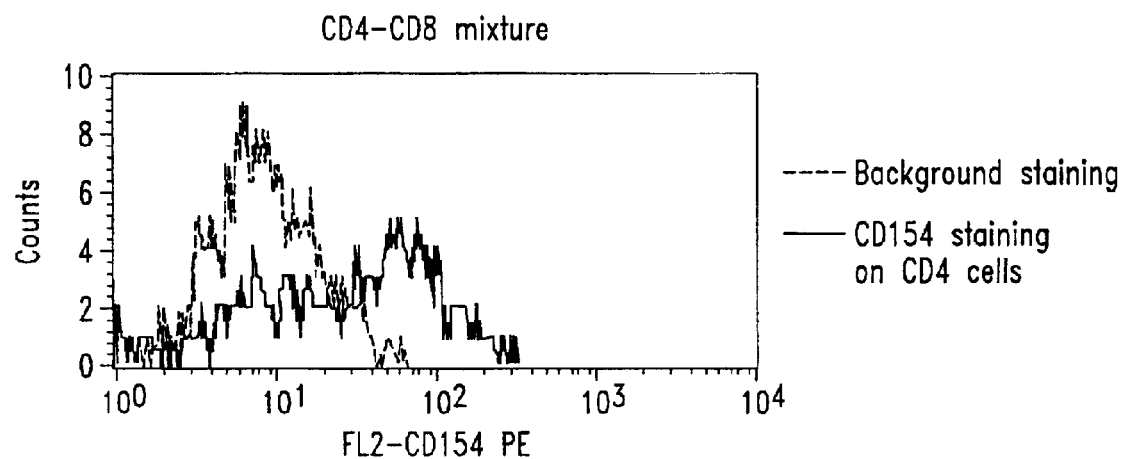
FIGS. 22A–22B are plots representing flow cytometry analyses of CD154 staining versus control staining (e.g., background) in cells with both CD4 and CD8 subpopulations (22A) or CD4-enriched populations (22B), prior to anti-CD3 and anti-CD28 co-immobilized bead stimulation.
Figure 22B:
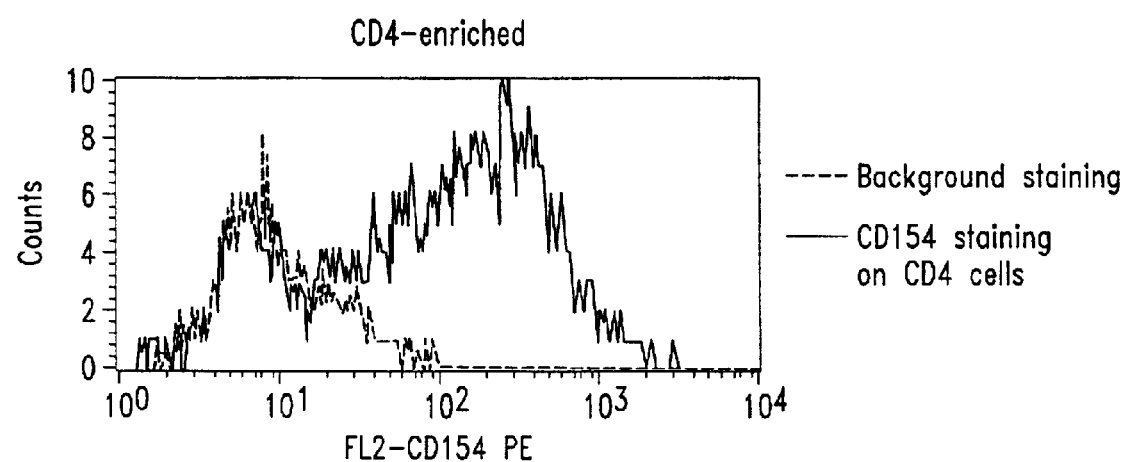
Figure 23A:
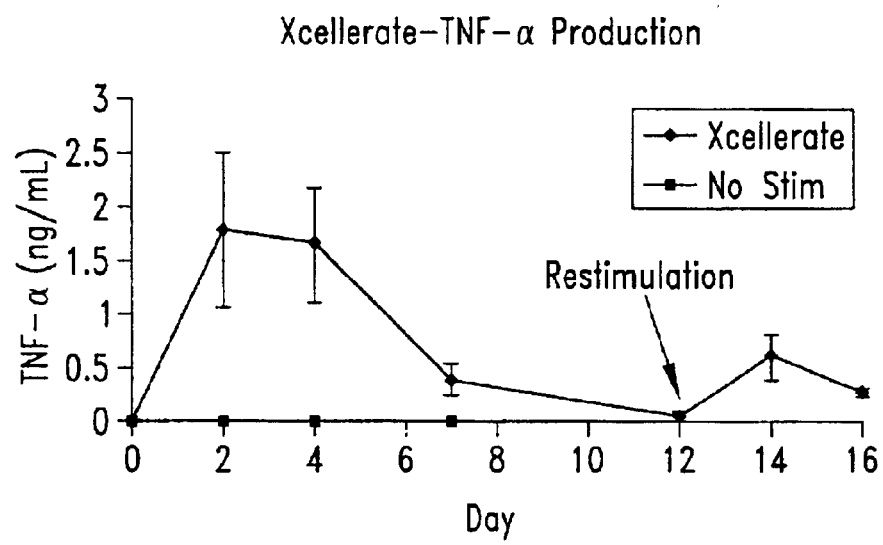
FIGS. 23A–23B are plots representing ELISA analysis of TNF-α (23A) and IFN-γ (23B) in media following stimulation of peripheral blood lymphocytes with anti-CD3 and anti-CD28 co-immobilized beads.
Figure 23B:
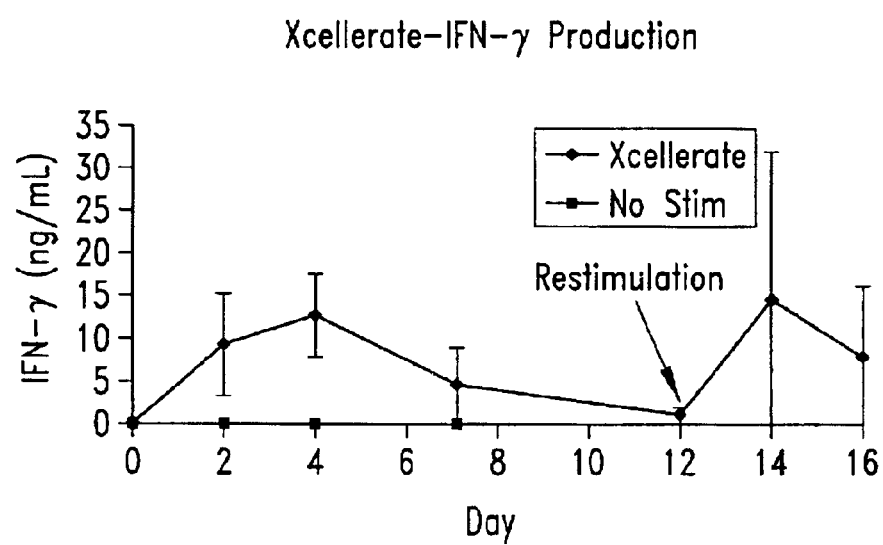
Figure 24A:
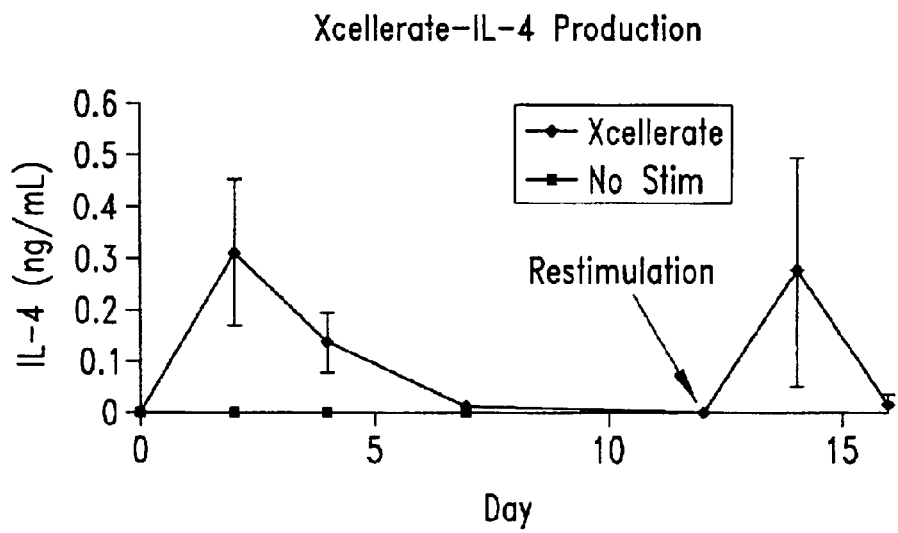
FIGS. 24A–24B are plots representing ELISA analysis of IL-4 (24A) and IL-2 (24B) in media following stimulation of peripheral blood lymphocytes with anti-CD3 and anti-CD28 co-immobilized beads.
Figure 24B:
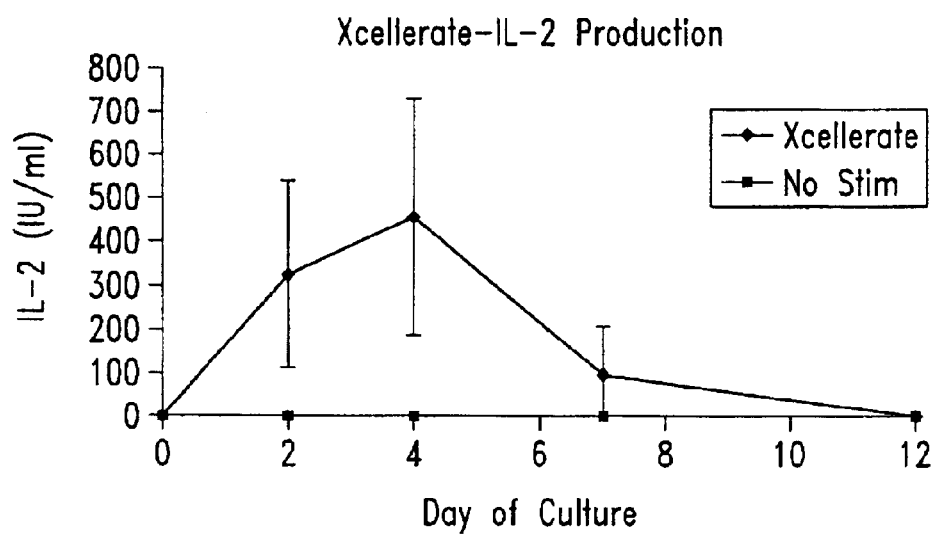
Figure 25:
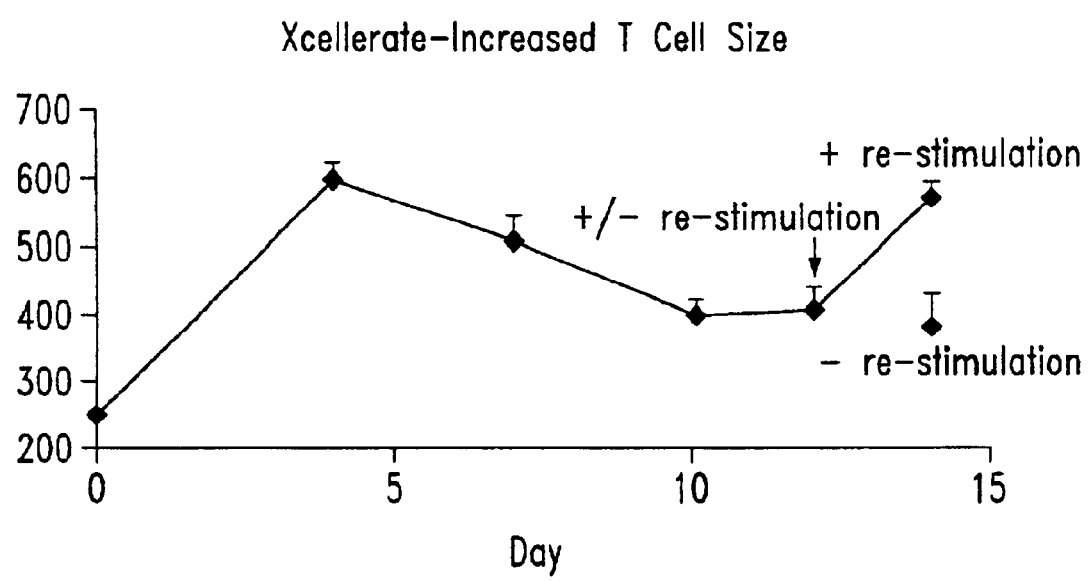
FIG. 25 is a plot depicting increase in T-cell size following stimulation of peripheral blood lymphocytes with anti-CD3 and anti-CD28 co-immobilized beads and using forward scatter analysis.
Figure 26A:
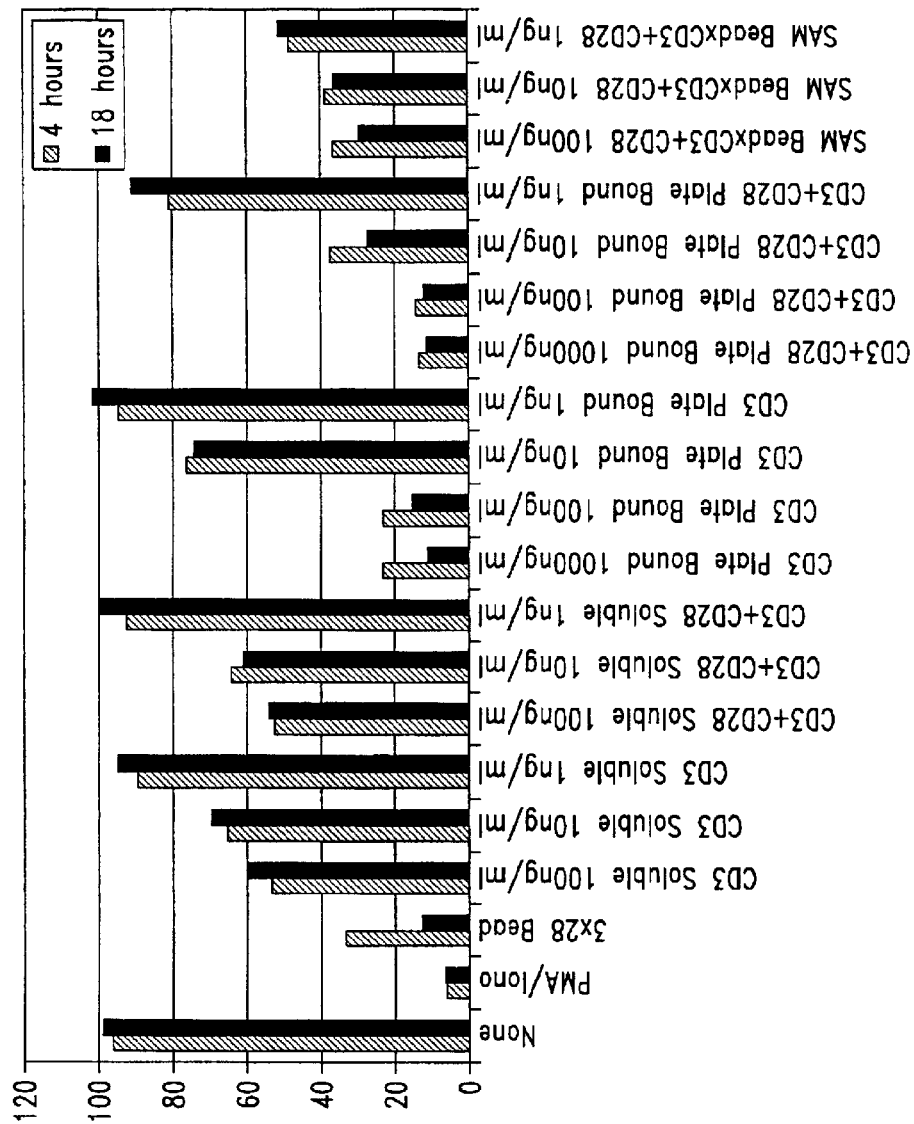
Figure 26B:
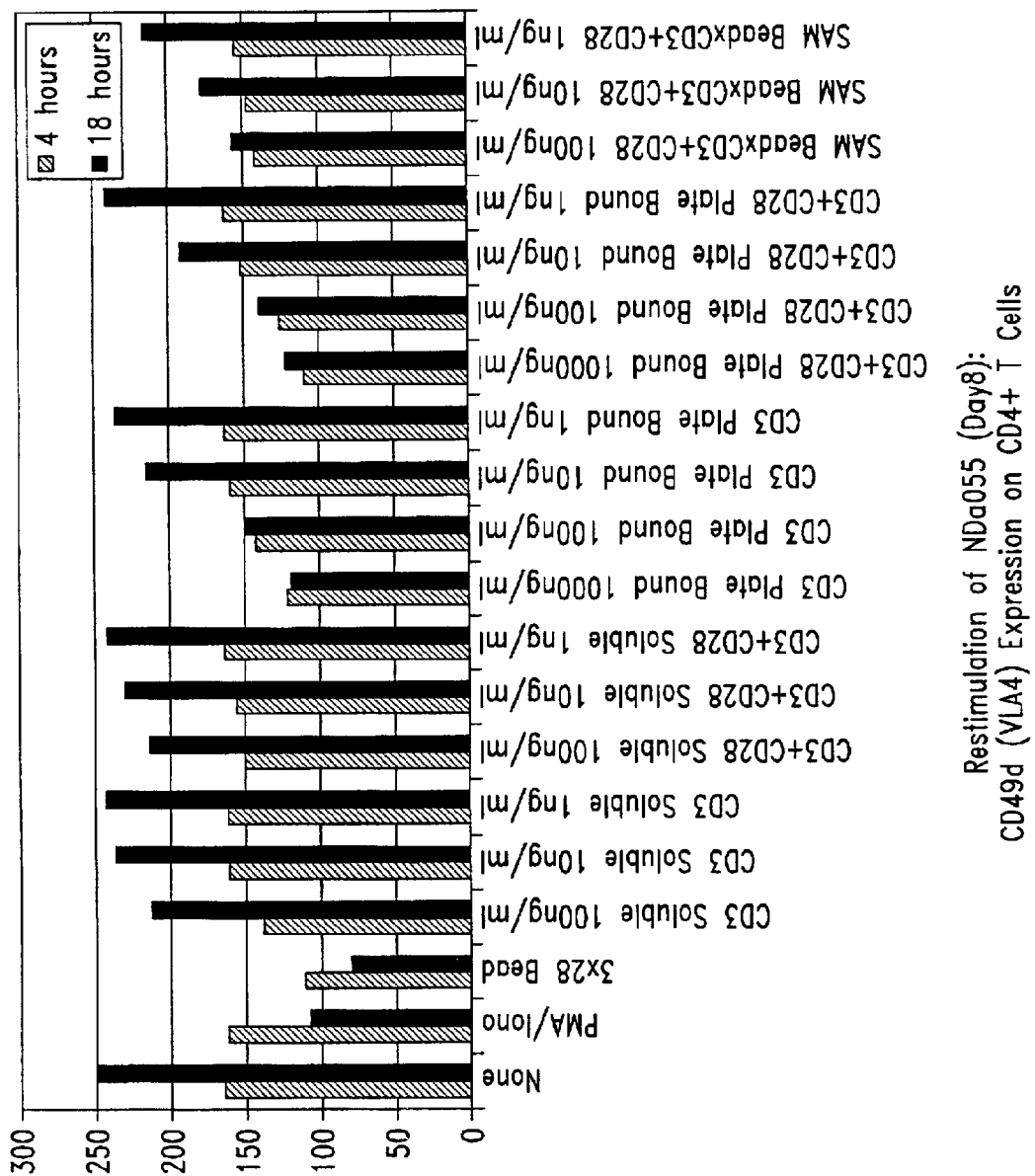
Figure 26C:
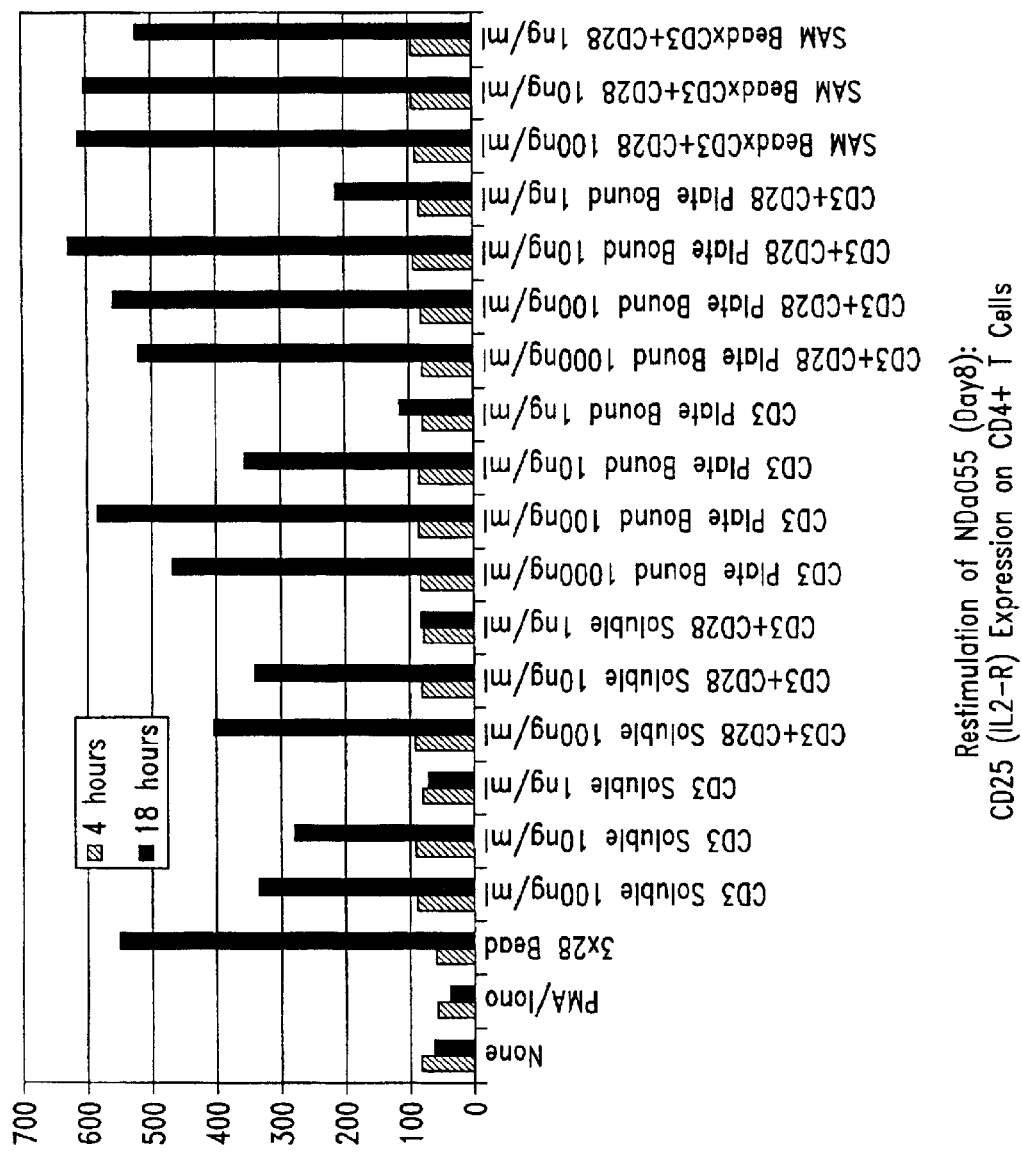
Figure 26D:
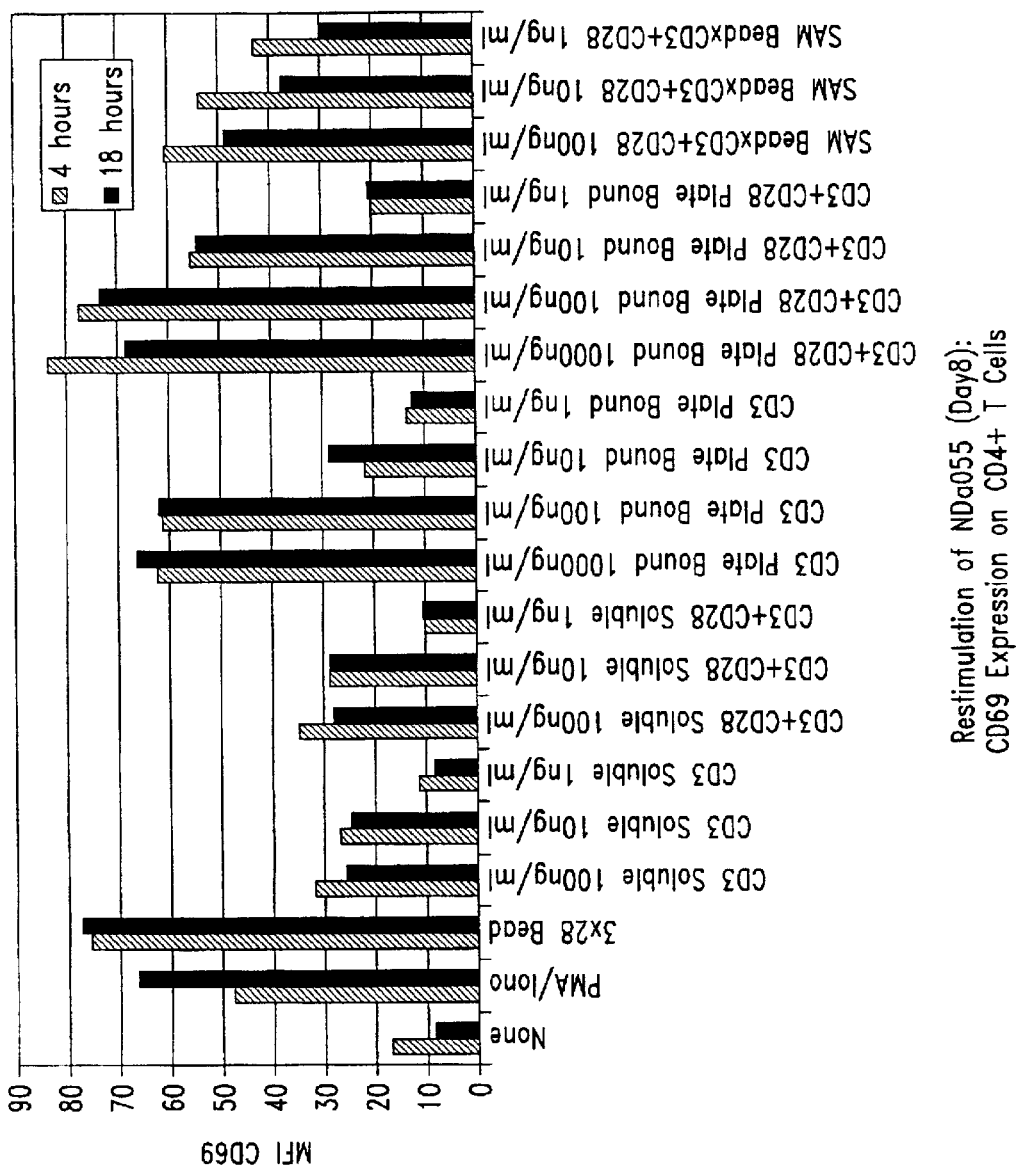
Figure 26E:
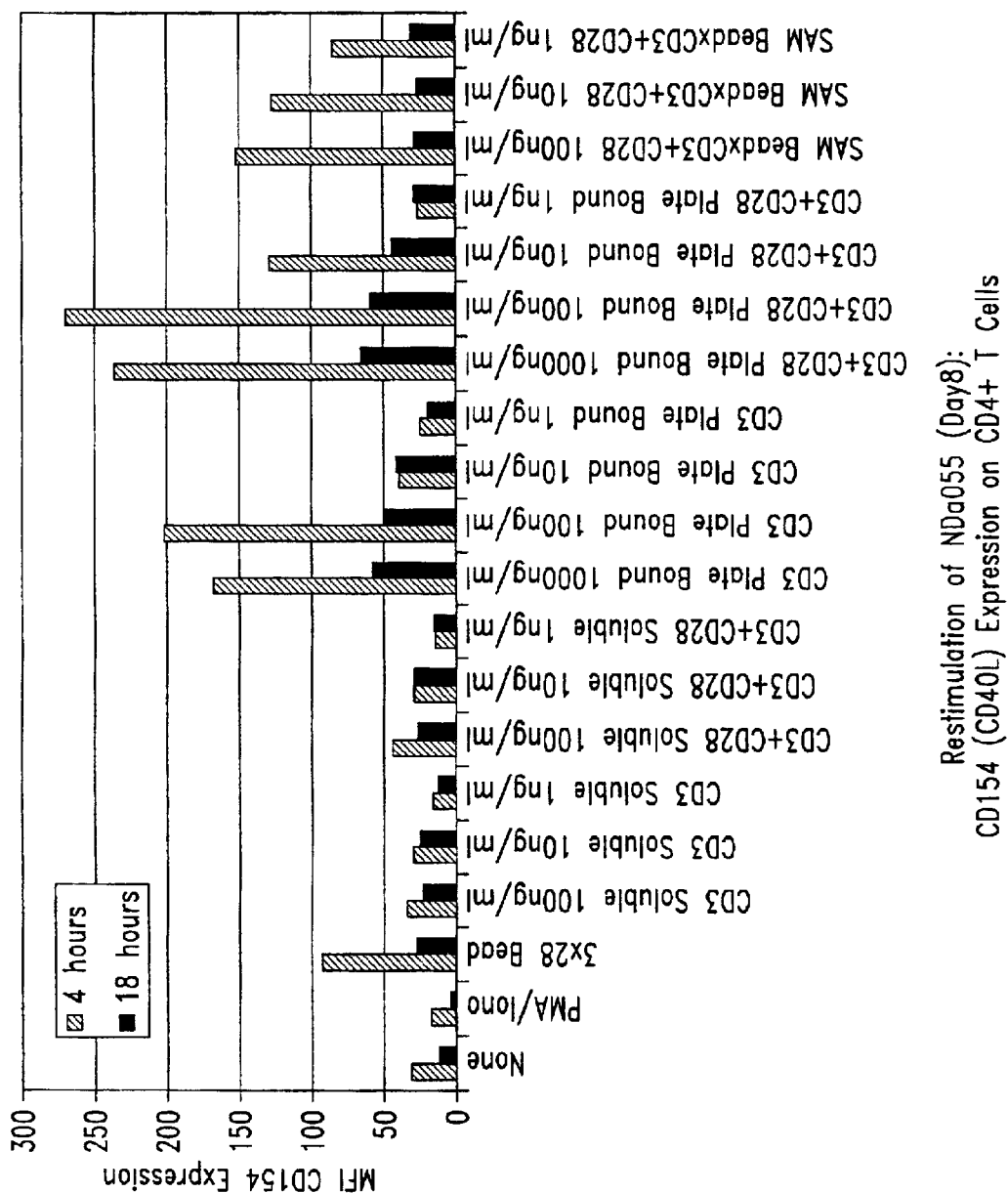
Figure 26F:
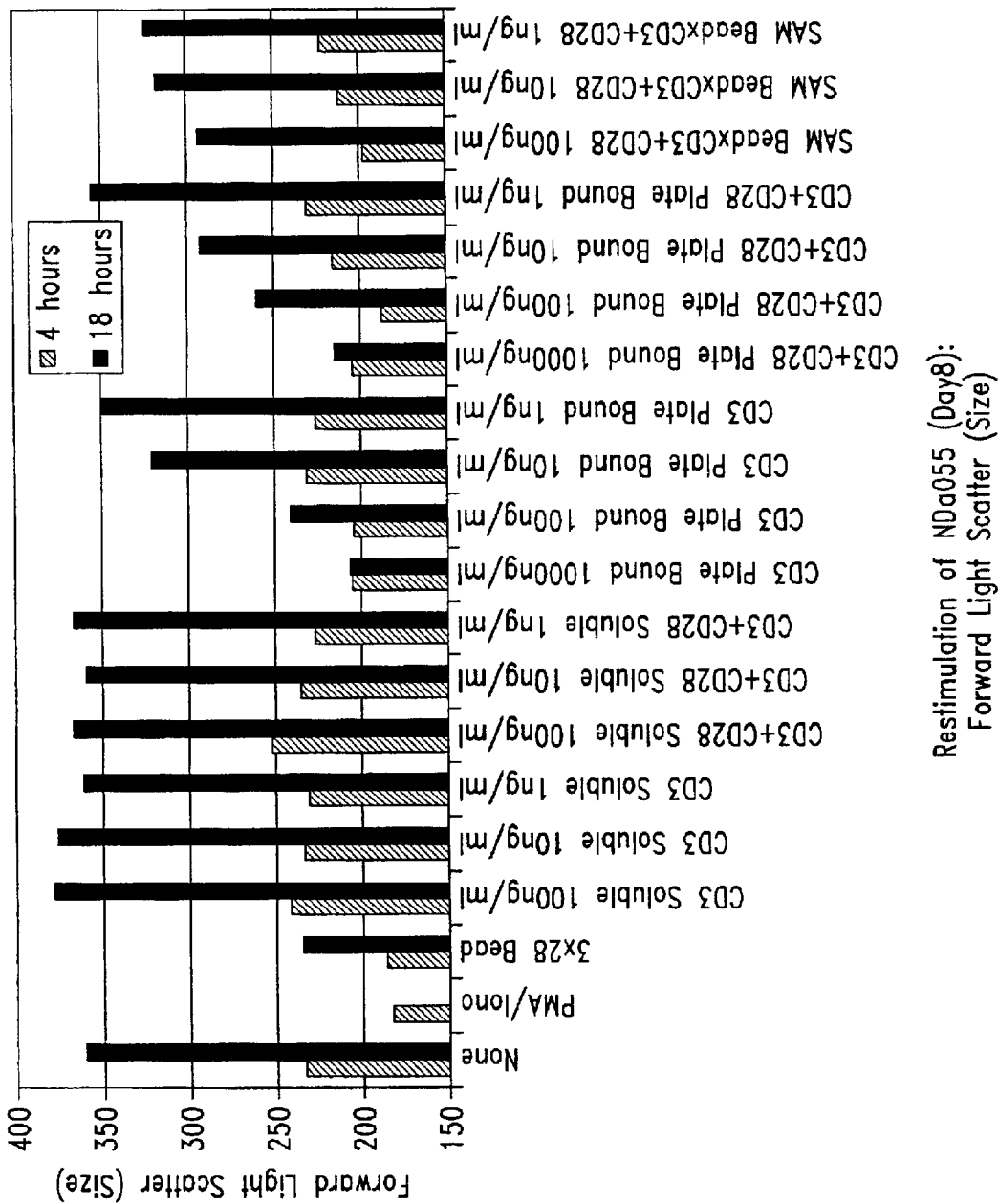
Figure 26H:
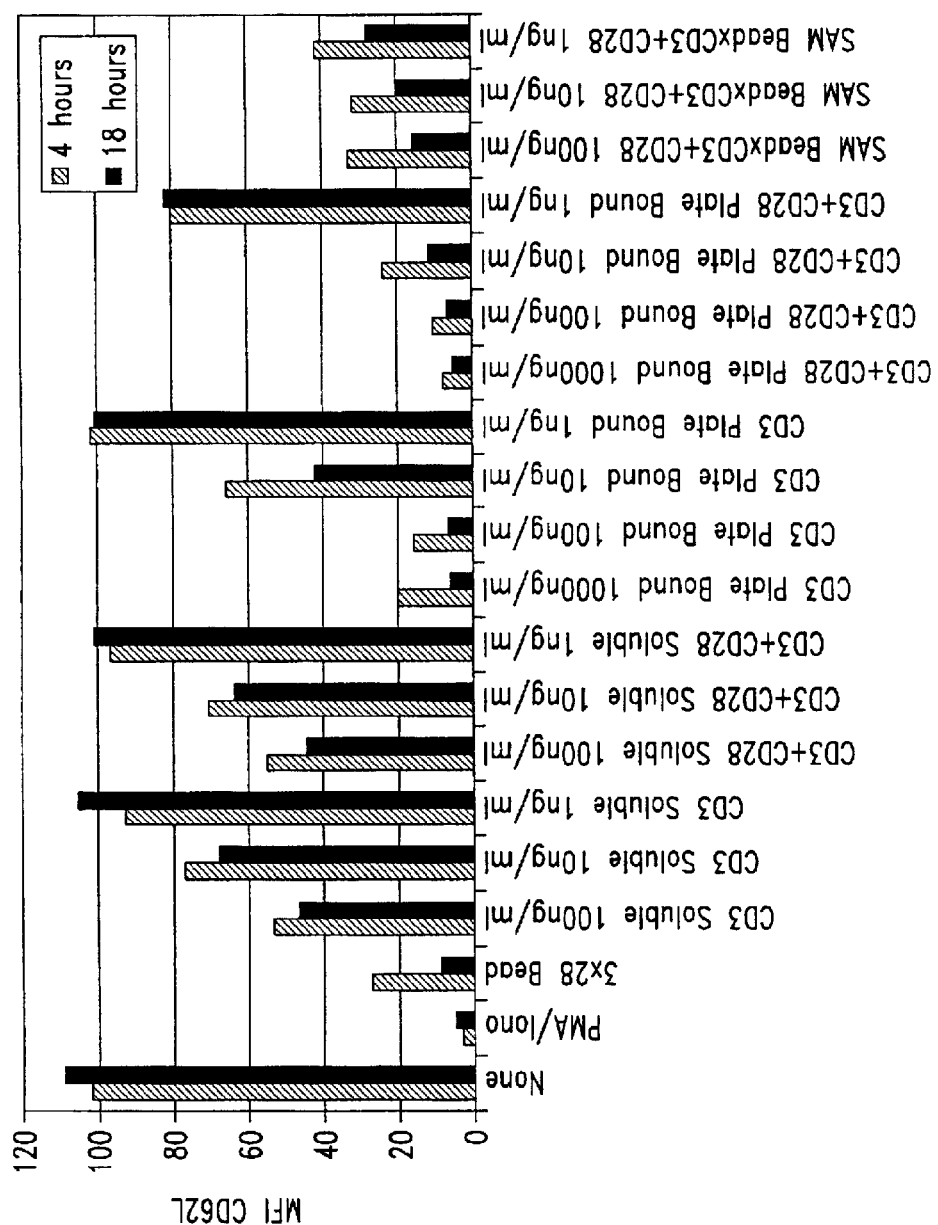
Figure 26I:
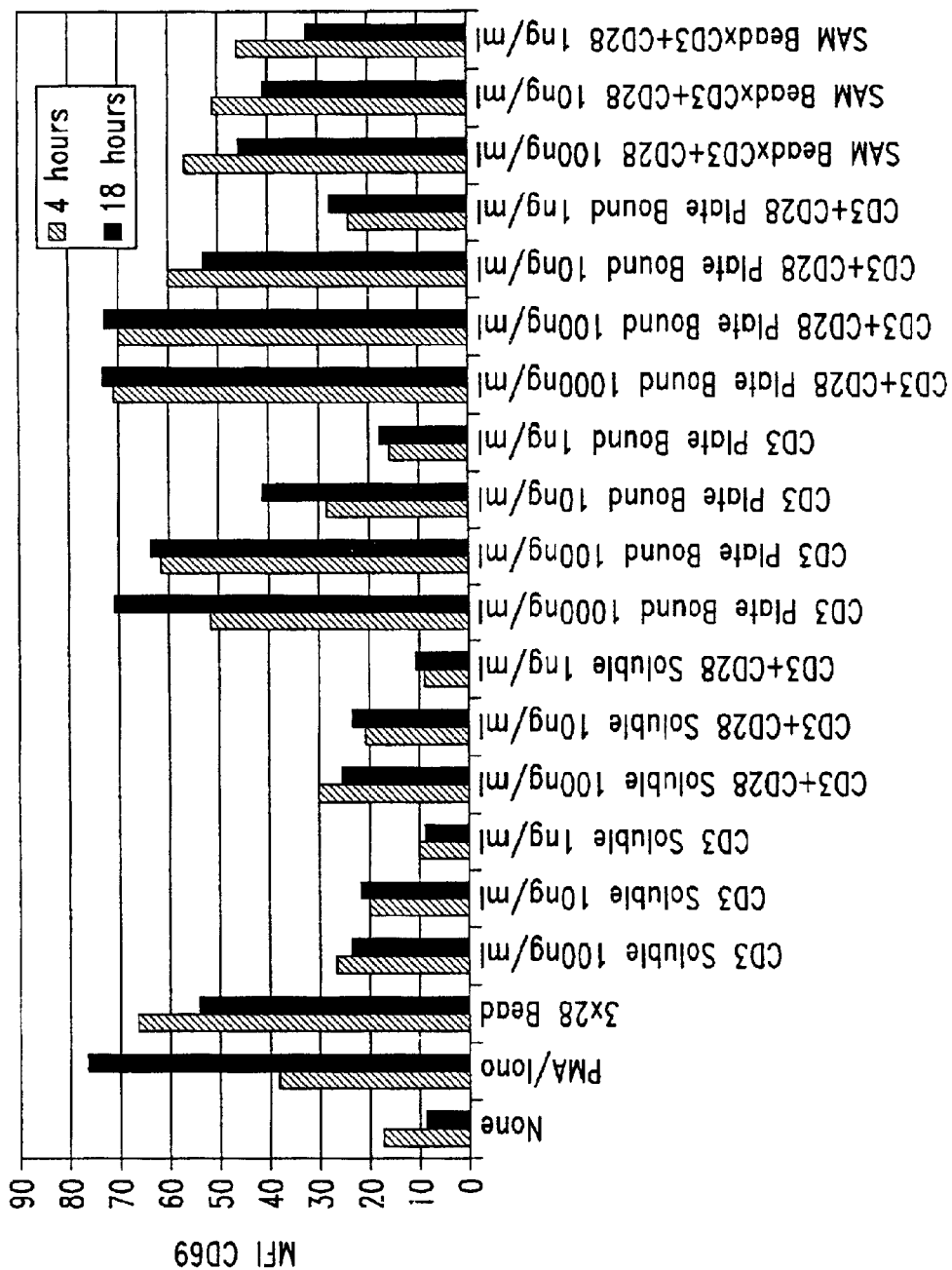
Figure 26J:
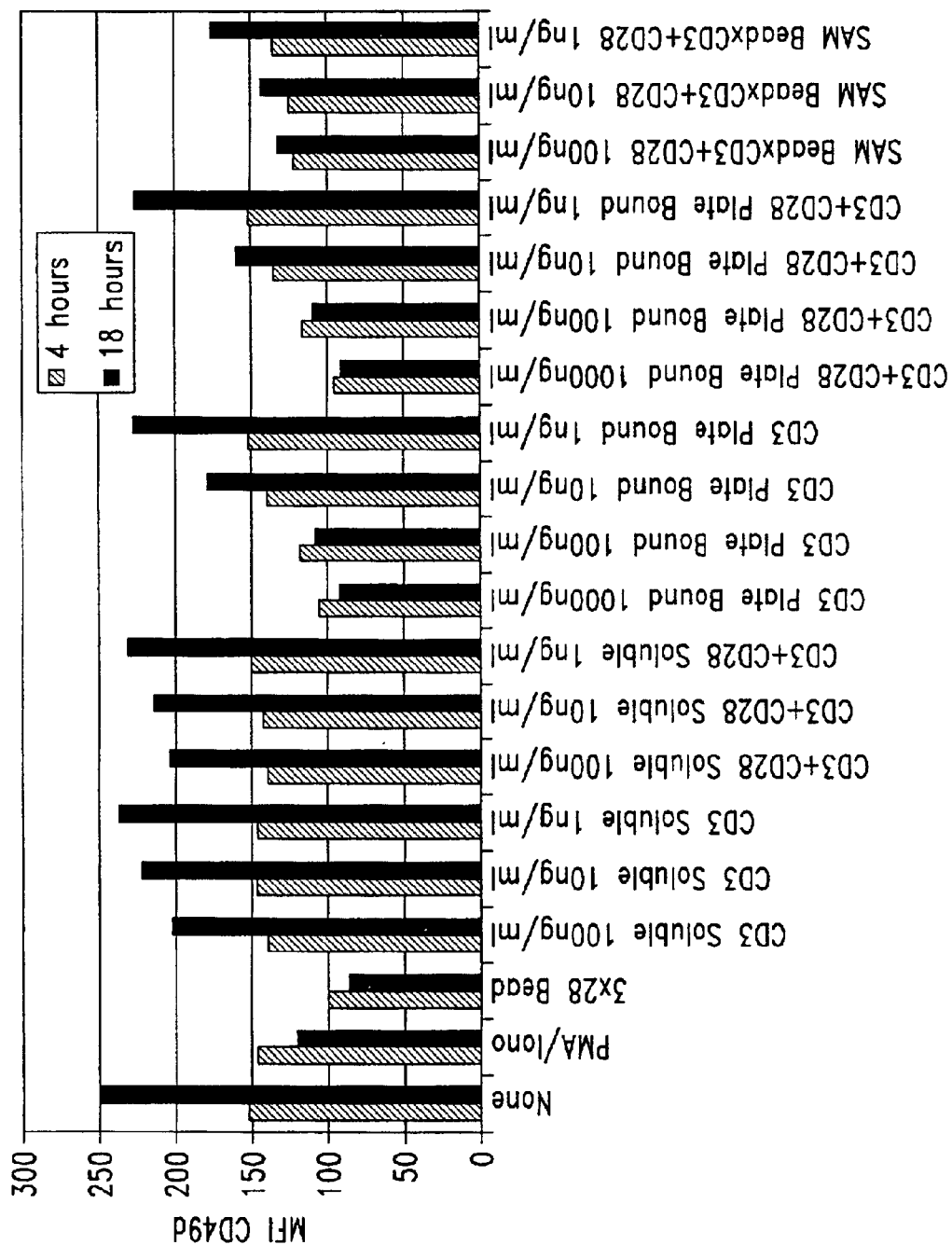
Figure 26K:
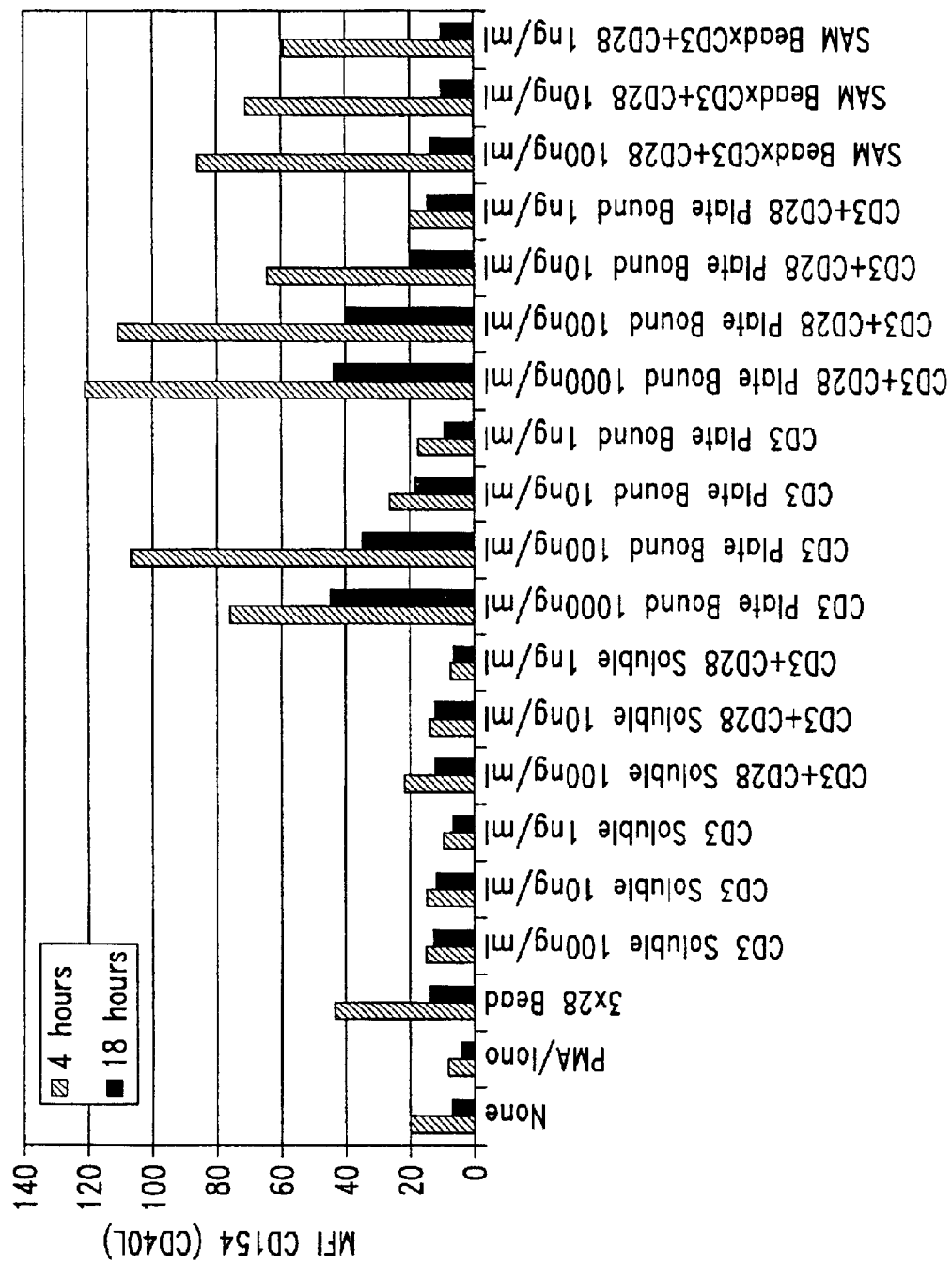
Figure 26L:
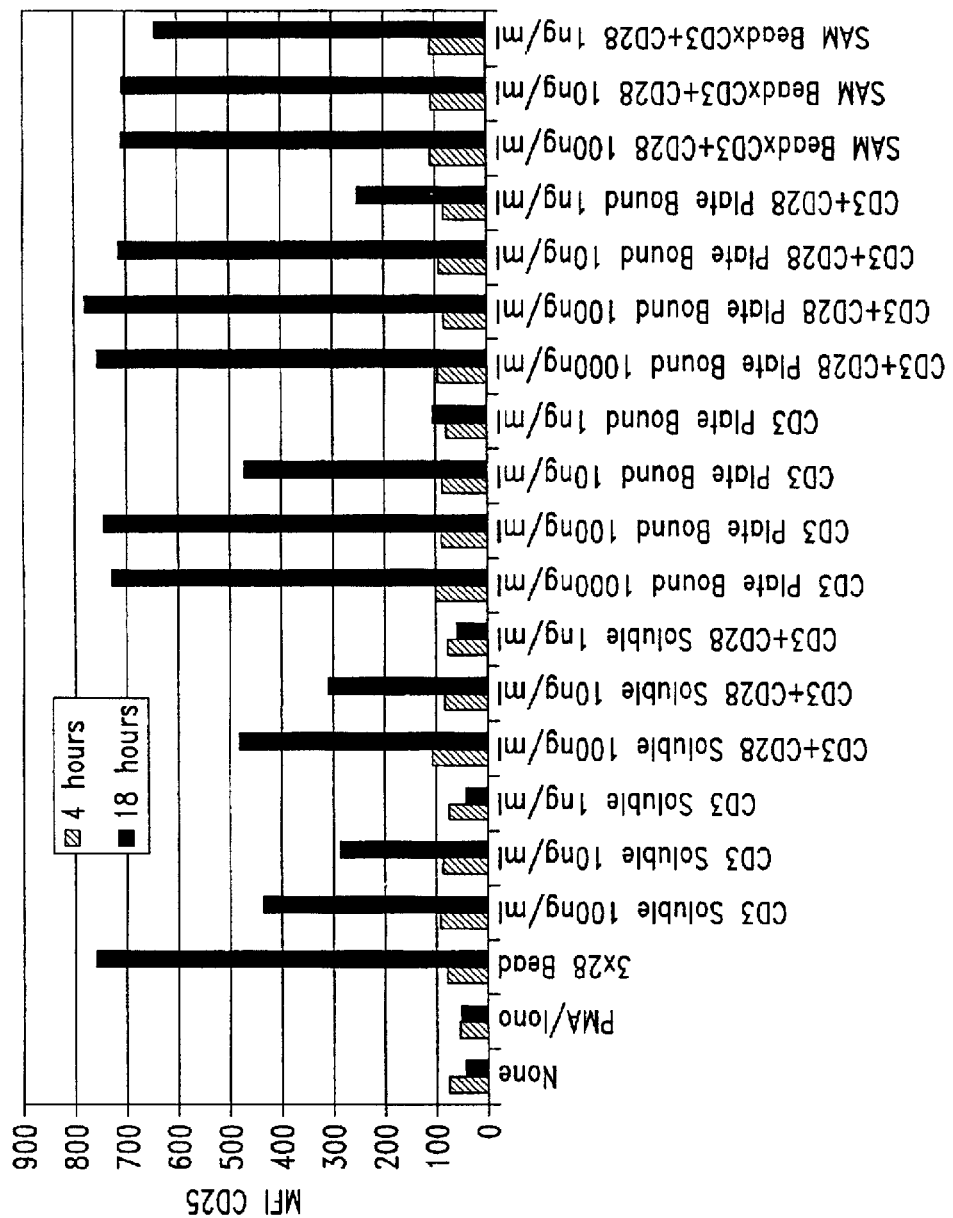

When 3×28-stimulated T-cells became more quiescent (low CD25, low forward scatter), they were re-stimulated as shown below:
1) No stimulation
2) PHA 2 ug/ml
3) 3×28 (Xcellerate) bead stimulation at 1 bead/$CD3^+$ T-cell A kinetic analysis of cell size (forward scatter), surface phenotype, activation marker expression, and cytokine secretion was then performed. FIG. 12 shows forward scatter (cell size) kinetics following primary and secondary stimulation. FIG. 13 shows CD25 (IL-2-Receptor) expression kinetics following primary and secondary stimulation. FIG. 16 shows CD54 (I-CAM) expression following secondary stimulation, on $CD4^+$ T-cells (A) and on $CD8^+$ T-cells (B), where the primary stimulation was either PHA or 3×28 beads, and re-stimulation was either: none, PHA, or 3×28 beads. Markers delineating between CD4 and CD8 positive cells were also used to determine their relative proportion during 3×28 antibody bead activation (FIGS. 19 and 22).

Example XII

Analysis of Cytokine Expression Patterns of Co-Stimulated T-Cells

The role of a variety of cytokines, including IL-2, IFN-γ, TNF-α, and IL-4 have been extensively studied as they relate to T-cell maintenance, expansion, and differentiation. Notably, IL-2 has been shown to be supportive of T-cell maintenance and expansion. IFN-γ has been implicated in driving T-cells to differentiate into $T_{H1}$-type immune responder, while IL-4 has been implicated for driving T-cells to $T_{H2}$-type responses. Cytokine release levels in primary human T-cells activated by either PHA or 3×28 beads were analyzed by stimulating T-cells as in Example IX, including kinetic studies of responses to primary stimulation and responses to a secondary stimulus. The data are shown in FIGS. 18A–C and FIGS. 23–24 demonstrate a unique feature of 3×28 bead stimulation. Between day 2 and day 4 following initial stimulation (day one was not assessed), extremely high levels of both IL-2 and IFN-γ were observed. A nearly 5-fold increase in absolute secreted IL-2 levels was seen for 3×28 bead-stimulated T-cells as compared to levels observed for cells stimulated with PHA. An approximate 7-fold increase in IFNγ levels was also observed in 3×28 stimulated T-cells as compared to their PHA counterparts. In the case of IL-4, the increase was not as dramatic for primary stimulation. Interestingly, and of possibly great significance, is that after cells became quiescent (no longer dividing or secreting the three cytokines mentioned above) following primary stimulation, they were re-stimulated with either 3×28 beads, PHA, or left unstimulated. T-cells which had received an initial activation/expansion signal through 3×28 beads secreted even higher levels of IFN-γ than observed following primary stimulation. In contrast, cells that were initially stimulated with PHA secreted IFN-γ levels much lower than seen for their 3×28 counterparts. Similar difference were also observed for IL-4 levels.

These data suggest that cells obtained following activation/expansion mediated through 3×28 beads are functionally different than those obtained from other means of expansion, such as PHA. The resultant cells appear to have an altered cytokine secretion response, one that promotes very high levels of both $T_{H1}$ and $T_2$ cytokines, with a possible favoring of the $T_{H1}$-type profile (IFN-γ). Secretion of such high levels of these cytokines in culture can have many effects, including: driving T-cells into a $T_{H1}$ differentiation pathway, which is one that favors anti-tumor and anti-viral responses; and also by altering the basic functionality of resultant T-cells (such as lowering threshold of activation and inhibiting programmed cell death pathways).

Example XIII

Analysis of CD54 Expression of Co-Stimulated T-Cells

FIG. 16 shows CD54 (I-CAM) expression following secondary stimulation, on $CD4^+$ T-cells (A) and on $CD8^+$ T-cells (B), where the primary stimulation was either PHA or 3×28 beads, and re-stimulation was either: none, PHA, or 3×28 beads.

Example XIV

Short Term Activation Marker Assays

Marker expression was monitored over various times following stimulation of T-cells as set forth in Example IX. In this regard cells are labeled with anti-human CD4 (Immunotech, Fullerton, Calif.), FITC-coupled anti-human CD11a (Pharmingen), FITC-coupled anti-human CD26 (Pharmingen), FITC-coupled anti-human CD49d (Coulter), FITC-coupled anti-human CD54 (Pharmingen and Becton Dickinson), FITC-coupled anti-human CD95 (Pharmingen), FITC-coupled anti-human CD134 (Pharmingen), FITC-coupled anti-human CD25 Ab (Becton Dickinson, Fullerton, Calif.), FITC-coupled anti-human CD69 Ab (Becton Dickinson), FITC- or PE-coupled anti-human CD154 Ab (Becton Dickinson), or FITC-or PE-coupled IgG1 isotype control Ab. Cells, $2 \times 10^5$ are labeled for 20 minutes at 4° C. with 2 μl of each antibody in a final volume of 30 μl, washed and resuspended in 1% paraformaldehyde (Sigma, St. Louis, Mo.). See FIGS. 21–22, and 26A–26L, as is demonstrated by these figures there appear significant differences over activation time as well as between $CD4^+$ and $CD8^+$ cells.

Example XV

T Cell Expansion Using Varying CD3:CD28 Ratios

Figure 27:
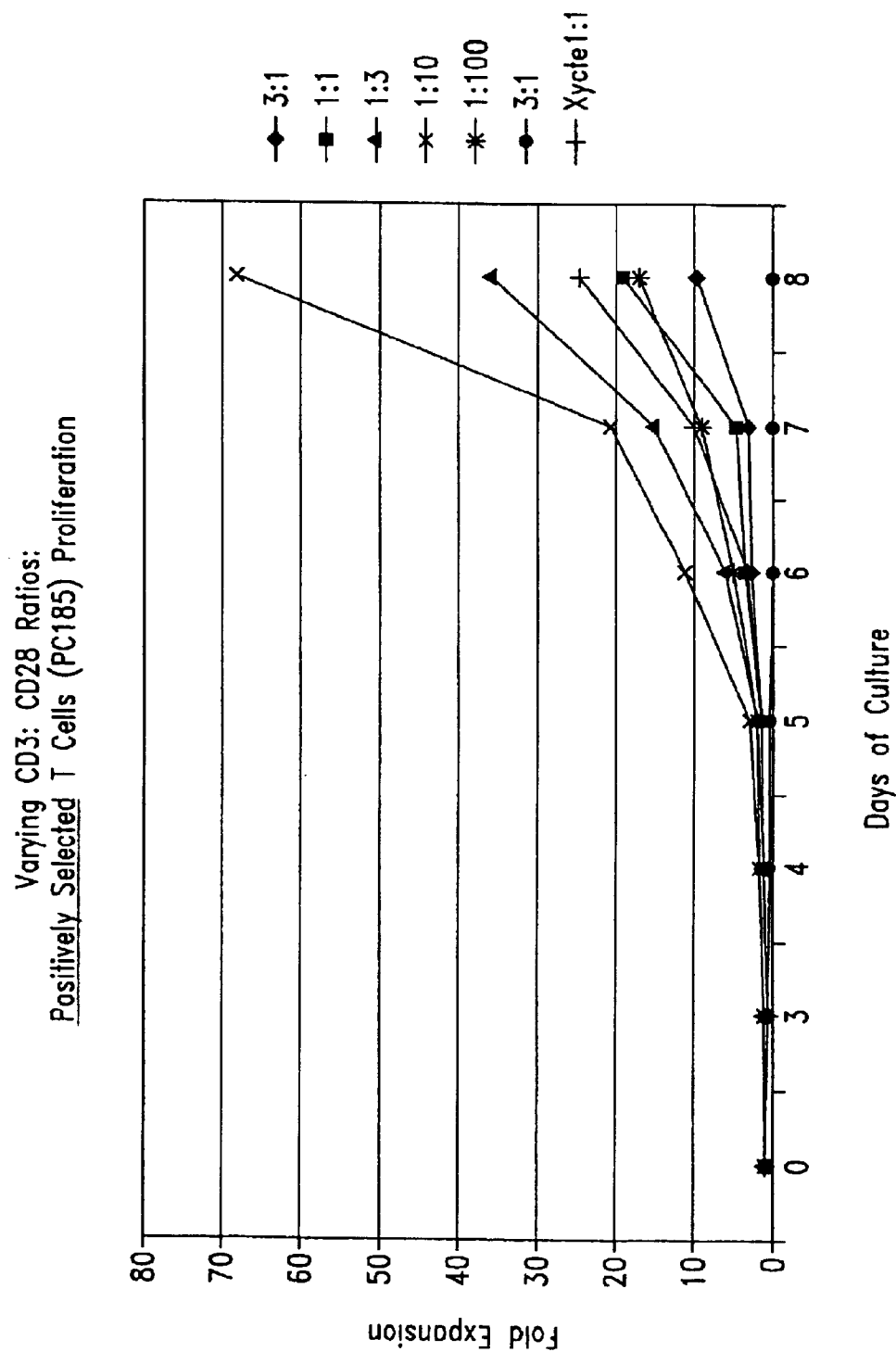
FIG. 27 is a graph depicting the fold increase of T-cells over time following stimulation with anti-CD3 and anti-CD28 co-immobilized beads with varying ratios of CD3:CD28.

T cell expansion was evaluated using varying concentrations of CD3:CD28 ratios on the 3×28 DYNABEADS® M-450. In the experiments described herein, the process referred to as XCELLERATE II™ was used, as described in Example I. As shown in FIG. 27, surprisingly, about a 68-fold expansion after 8 days of culture was observed with a CD3:CD28 ratio of 1:10 on the beads. A 35-fold expansion of T cells was seen after 8 days of culture with a CD3:CD28 ratio of 1:3 on the beads. At a 1:1 ratio, about a 24-fold expansion was seen.

Example XVI

T Cell Expansion Using Varying Bead:T-Cell Ratios for Positive Selection Followed by Varying Amounts of Sequential Addition of Beads This example describes modifications to the EXCELLERATE II™ process (see Example 1) to determine the most effective bead:T-cell ratios for positive selection and for optimal T cell expansion through the first 10 days of stimulation.

In the first experiment, comparisons were made of cells positively selected with a 1:1 ratio of 3×28 beads:cells and stimulated with varying ratios of sequentially added 3×28 beads in the first 10 days of stimulation. Cells were positively selected with 3×28 DYNABEADS® M-450 at bead:T-cell ratios of 3:1 and 1:1. For the 3:1 ratio, $20 \times 10^6$ cells (assuming 50–60% T cells) were isolated and resuspended in 1 ml PBS+5% human serum. $30 \times 10^6$ washed beads were added for a total volume of 2 mls. For the 1:1 ratio, $10 \times 10^6$ washed beads were added to the $10 \times 10^6$ total cells. The cells were cultured in T-25 flasks and on day 3, counted and split into 6-well plates in 5 ml volume. On day 5, all wells were split to $1.25 \times 10^6$ cells/well. On days 3, 4, and 6–9, all wells were split to $2.5 \times 10^6$ cells/well. 3×28 beads were then sequentially added to those cells positively selected at 1:1 ratio beads:cells. As summarized in Table 7, cell yields on day 10 were highest with sequential addition of beads on days 3, 4, and 5 at a final ratio of 0.2:1.

TABLE 7

Cell Yield on Day 10 Following Varying Sequential 3 × 28 Bead Addition

| Positive Selection Ratio (beads:cells) | Ratio of Sequentially Added Beads (beads:cells) | Cell Yield × $10^6$ on Day 10 |
| --- | --- | --- |
| 3:1 Selection | None | 4,300 |
| 1:1 Selection | None | 2,600 |
| 1:1 Selection | 0.33:1 on D1 & 2 | 6,700 |
| 1:1 Selection | 0.2:1 on D1 & 2 | 4,000 |
| 1:1 Selection | 0.2:1 on D1–5 | 9,600 |
| 1:1 Selection | 0.2:1 on D3–5 | 11,400 |

In a second experiment, positive selection times were varied from 0.5–1.0 hour amd the bead:cell ratios varied from 3:1 to 1:1. As summarized in Table 8, the highest cell yield at day 10 was obtained with a 1:1 bead:cell ratio selection for 60 minutes and sequential addition of beads at 0.2:1 ratio on days 3 and 5. It should be noted however, that selecting with a bead:cell ratio of 3:1 for 30 minutes gave the highest positive selection yields.

TABLE 8

Cell Yield on Day 10 Following Varying Positive Selection Ratios, Times, and Sequential 3 × 28 Bead Addition

| Positive Selection Bead:Cell Ratio | Positive Selection Time | Ratio of Sequentially Added Beads (Beads:Cells) | Cell Yield × $10^6$ on Day 10 |
| --- | --- | --- | --- |
| 3:1 | 30 minutes | 0.2:1 on D3 | 5,100 |
| 1:1 | 30 minutes | None | 3,300 |
| 1:1 | 30 minutes | 0.2:1 on D3 | 4,400 |
| 1:1 | 30 minutes | 0.2:1 on D3 & D5 | 5,700 |
| 1:1 | 30 minutes | 0.2:1 on D3, 4, & 5 | 6,700 |
| 1:1 | 60 minutes | None | 3,400 |
| 1:1 | 60 minutes | 0.2:1 on D3 | 4,800 |
| 1:1 | 60 minutes | 0.2:1 on D3 & D5 | 9,000 |
| 1:1 | 60 minutes | 0.2:1 on D3, 4, & 5 | 7,900 |

All of the above U.S. patents, U.S. patent application publications, U.S. patent applications, foreign patents, foreign patent applications and non-patent publications referred to in this specification and/or listed in the Application Data Sheet, including but not limited to U.S. patent application Ser. No. 09/960,264, filed Sep. 20, 2001; which is a continuation-in-part of U.S. application Ser. No. 09/794,230, filed Feb. 26, 2001; which claims the benefit of Provisional Application Nos. 60/184,788, filed Feb. 24, 2000, and 60/249,902, filed Nov. 17, 2000, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims. All of references, patents, patent applications, etc. cited above, are incorporated herein in their entirety. Further, all numerical ranges recited herein explicitly include all integer values within the range.

What is claimed is:

1. A method for stimulating a population of T-cells by cell surface moiety ligation, comprising:
   (i) providing a population of cells wherein at least a portion thereof comprises T-cells;
   (ii) contacting said population of cells with a surface, wherein said surface has attached thereto a first agent that ligates a TCR/CD3 complex of a T-cell, and the same or a second surface has attached thereto a second agent that ligates a CD28 accessory molecule of said T-cell, wherein the ratio of said first agent to said second agent is less than one and wherein said ligation by the first and second agent induces proliferation of said T-cell.

2. The method of claim 1, wherein at least one agent is an antibody or an antibody fragment.

3. The method of claim 1, wherein the first agent is an antibody or a fragment thereof, and the second agent is an antibody or a fragment thereof.

4. The method of claim 1, wherein the first agent is an anti-CD3 antibody, an anti-CD2 antibody, or an antibody fragment of an anti-CD3 or anti-CD2 antibody.

5. The method of claim 1, wherein the second agent is an anti-CD28 antibody or antibody fragment thereof.

6. The method of claim 1, wherein the first agent is an anti-CD3 antibody and the second agent is an anti-CD28 antibody.

7. The method of claim 6, wherein the anti-CD3 antibody and the anti-CD28 antibody are present at a ratio of about 1:30 to about 1:100.

8. The method of claim 6, wherein the anti-CD3 antibody and the anti-CD28 antibody are present at a ratio of about 1:30.

9. The method of claim 6, wherein the anti-CD3 antibody and the anti-CD28 antibody are present at a ratio of about 1:25.

10. The method of claim 6, wherein the anti-CD3 antibody and the anti-CD28 antibody are present at a ratio of about 1:20.

11. The method of claim 6, wherein the anti-CD3 antibody and the anti-CD28 antibody are present at a ratio of about 1:15.

12. The method of claim 6, wherein the anti-CD3 antibody and the anti-CD28 antibody are present at a ratio of about 1:10.

13. The method of claim 6, wherein the anti-CD3 antibody and the anti-CD28 antibody are present at a ratio of about 1:3.

14. The method of claim 1, wherein the first agent is an anti-CD3 antibody and the second agent is a ligand for CD28.

15. The method of claim 14, wherein the ligand is a natural ligand for CD28.

16. The method of claim 15, wherein the natural ligand is B7.

17. A method for stimulating a population of T-cells by cell surface moiety ligation, comprising:

(i) providing a population of cells wherein at least a portion thereof comprises T-cells;

(ii) contacting said population of cells with a surface, wherein said surface has attached thereto a first agent that ligates a TCR/CD3 complex of a T-cell, and the same or a second surface has attached thereto a second agent that ligates a CD28 accessory molecule of said T-cell, wherein the final ratio of said surface to said cells is greater than 1 on day 1 and wherein additional surface is added sequentially to the cells thereafter for up to 10 days at a final ratio of surface to cells of about 1:5, and wherein said ligation by the first and second agent induces proliferation of said T-cell.

18. The method of claim 17, wherein said final ratio is about 1:1 surface:cells on day 1 and wherein additional surface is added sequentially to the cells thereafter every day for up to 10 days at a final ratio of about 1:5.

19. The method of claim 17, wherein said final ratio is about 3:1 surface:cells on day 1 and at a final ratio of about 1:5 on days 3 and 5.

20. The method of claim 17, wherein said final ratio is about 2:1 surface:cells on day 1 and at a final ratio of about 1:5 on days 3 and 5.

21. The method of claim 21, wherein said final ratio is about 1:1 surface:cells on day 1 and at a final ratio of about 1:5 on days 3 and 5.

* * * * *

UNITED STATES PATENT AND TRADEMARK OFFICE
CERTIFICATE OF CORRECTION

PATENT NO.     : 6,867,041 B2
DATED          : March 15, 2005
INVENTOR(S)    : Ronald Berenson et al.

It is certified that error appears in the above-identified patent and that said Letters Patent is hereby corrected as shown below:

<u>Column 62,</u>
Line 23, "claim 21" should read as -- claim 17 --.

Signed and Sealed this

Thirtieth Day of August, 2005

JON W. DUDAS
*Director of the United States Patent and Trademark Office*